US005721119A

United States Patent [19]
Singh et al.

[11] Patent Number: 5,721,119
[45] Date of Patent: Feb. 24, 1998

[54] RYEGRASS POLLEN ALLERGEN

[75] Inventors: Mohan Bir Singh, Templestowe; Robert Bruce Knox, North Balwyn; Eng Kok Ong, Greensborough, all of Australia

[73] Assignee: University of Melbourne, Melbourne, Australia

[21] Appl. No.: 433,854

[22] Filed: May 2, 1995

Related U.S. Application Data

[62] Division of Ser. No. 195,947, Feb. 14, 1994, which is a continuation of Ser. No. 930,060, Aug. 14, 1992, abandoned, which is a continuation-in-part of Ser. No. 746,702, Aug. 16, 1991, abandoned, which is a continuation-in-part of Ser. No. 585,086, Oct. 6, 1990, abandoned.

[51] Int. Cl.$^6$ .......................... C12P 21/00; A61K 39/36; C07K 14/415
[52] U.S. Cl. .................. 435/69.3; 435/69.1; 435/172.3; 435/91.32; 536/23.1; 536/23.6; 536/24.1; 424/275.1; 424/93.2
[58] Field of Search .................... 435/69.1, 69.3, 435/172.3, 91.32; 536/23.1, 23.6, 24.1; 424/184.1, 275.1, 93.2

[56] References Cited

FOREIGN PATENT DOCUMENTS 8909260 10/1989 WIPO.

OTHER PUBLICATIONS

Klysner et al., Clin. Exp. Allergy 22:491–497, 1992.
Kumar et al., Proc. Natl. Acad. Sci. USA, 87:1337–1341 (Feb. 1990).
Paul et al., Fundamental Immunology, Second Edition, Raven Press, NY, 1989, pp. 867–888.
Klein et al., Immunology, The Science of Self-Nonself Discrimination, Max-Planck-Institut fur Biologie, Tubingen, Federal Republic of Germany, 1982.
Singh et al., Proc. Natl. Acad. Sci. USA, 88:1384–1388 (Feb. 1991).
Margalit et al., The Journal of Immunology, 138:2213–2229, No. 7 (Apr. 1987).
Hopp et al., Proc. Natl. Acad. Sci. USA, 78:3824–3828, No. 6 (Jun. 1981).
Ellis, Vaccines, W.B. Saunders Company, 1988, New Technologies for Making Vaccines pp. 568–575.
Cottam et al., Biochem. J., 234:305–310, 1986.
Walsh et al., Int. Arch Allergy Appl. Immunol., 90:78–83, 1989.
Van Ree et al., J. Allergy Clin. Immunol., 83:144–151, No. 1, 1989.
Perez et al., J. Biol. Chem., 265:16210–16215, No. 27, 1990.
Walsh et al., Int. Arch. Allergy Appl. Immunol., 91:419–425, 1990.
Griffith et al., Febs Letters, vol. 279, No. 1, 1991.
Silvanovich et al., J. Biol. Chem., 266:1204–1210, No. 2, 1991.
Mohapatra, Int. Arch. Allergy Appl. Immunol., 91:362–368.
Olsen et al., J. of Immunology, vol. 147, No. 1, 1991.
Friedhoff et al., J. Allergy Clin. Immunol., 80:646–655, 1987.
Friedhoff et al., J. Allergy Clin. Immunol., 78:1190–1201 (Part I), 1986.
Smart et al., Int. Arch. Allergy Appl. Immunol., 62:179–187, 1980.
Howlett et al., Clinical Allergy, 12:259–268, 1982.
Vithange et al., Histochemical Journal, 14:949–996, 1982.
Hill et al., Clin. Allergy, 12:83–89, 1982.
Mohapatra et al., Aerobiologia, 6:205–211, 1990.
Esch et al., Molec. Immunol., 26:557–561, 26:557–561.
Chakrabarty et al., Int. Archs. Allergy Appl. Immun., 66:142–157, 1981.
Standring et al., Int. Archs Allergy Appl. Immunol., 83:96–103, 1987.
Hatton et al., J. Allergy Immunology, 81(1):183, 1988.
Bose et al., Immunology, 59:309–315, 1986.
Cornford et al., Int. Arch. Allergy Appl. Immunol., 93:41, 1990.
Cottam et al., Immunology Letters, 17:345–350, 1988.
Kahn et al., Mol. Immunology, 23(12):1281–1288, 1986.
Lin et al., Int. Arch. Allergy Appl. Immunol., 87:294–300, 1988.
Lin et al., Int. Arch Allergy Appl. Immunol, 91:217–223, 1990.
Marsh et al., Immunology, 22:1013–1028, 1972.
Martin et al., Annols of Allergy Cann. Allergy, 54:99–104, 1985.
Mourad et al., Journal of Immunological Methods, 89:53–59, 1986.
Mourad et al., The Journal of Immunology, 141:3486–3491, 1988.
Mourad et al., Molecular Immunology, 26(11):1051–1057, 1989.
Singh et al., Mono. Allergy, 28:101–120, 1990.
Smart et al., Int. Archs. Allergy Appl. Immun., 72:243–248, 1983.
Strandring et al., Int. Arch. Allergy Appl. Immunol., 87:337–341, 1988.
Mercheri et al., Int. Archs. Allergy Appl. Immunol., 78:283–289, 1985.

(List continued on next page.)

Primary Examiner—Christine M. Nucker
Assistant Examiner—Laurie Scheiner
Attorney, Agent, or Firm—Christopher A. Klein

[57] ABSTRACT

The present invention provides nucleic acid sequences coding for two ryegrass pollen allergen Lol p Ib family members, purified Lol p Ib.1 and Lol p Ib.2 proteins and fragments thereof, methods of producing recombinant Lol p Ib.1 or Lol p Ib.2 or at least one fragment thereof or derivative or homologue thereof, and methods of using the nucleic acid sequences, proteins and peptides of the invention.

11 Claims, 34 Drawing Sheets

OTHER PUBLICATIONS

Lowenstein et al., *Int. Archs. Allergy Appl. Immunol.*, 57:379–383, 1978.

Lowenstein et al., *Allergy*, 33:30–41, 1978.

Lowenstein et al., *Allergy*, 35:188–191, 1980.

Lowenstein et al., *Int. Archs. Allergy Appl. Immunol.*, 49:95–98, 1974.

Matthiesen et al., Epitope of Atopic Allergens, Brussels, UCB Institute of Allergy, pp. 9–13, 1990.

Matthiesen et al., *Clinical and Experimental Allergy*, 21:297–307, 1991.

Matthiesen et al., *Clinical and Experimental Allergy*, 21:309–320, 1991.

Van Hage–Hamsten et al., *J. Allergy Clin. Immunol.*, 85:279, 1990.

Ventas et al. *Clin. Experimental Allergy*, 20:47, 1990.

Zhang et al., *J. Allergy*, 87:325, 1991.

Brieva et al., *Journal of Chromatography*, 370:165–172, 1986.

Cook et al., *Int. Arch. Allergy Appl. Immunol.*, 85:104–108, 1988.

Friedhoff et al., *Tissue Antigens*, 31:211–219, 1988.

Singh et al., *Int. Archs. Allergy Appl. Immunol.*, 78:300–304, 1985.

Wheeler et al., *Int. Archs. Allergy Appl. Immunol.*, 86:1–8, 1988.

```
CGCTATCCCT CCCTCGTACA AACAAACGCA AGAGCAGCA ATG GCC GTC CAG AAG                                    54
                                           Met Ala Val Gln Lys
                                           -25

TAC ACG GTG GCT CTA TTC CTC GCC GTG GCC CTC GCC GGC CCG GCC                                      102
Tyr Thr Val Ala Leu Phe Leu Ala Val Ala Leu Ala Gly Pro Ala
-20             -15                 -10                 -5

GCC TCC TAC GCC GCT GAC GCC ACC TAC ACC CCG GCC GCG GGC CCG GCC                                  150
Ala Ser Tyr Ala Ala Asp Ala Thr Tyr Thr Pro Ala Ala Gly Pro Ala
                -1                    5              10

CCG ACT CCT GCT ACC ACC CCG GCT GGA AAC GTC CCG GGG AAG GCG ACC                                  198
Pro Thr Pro Ala Thr Thr Pro Ala Gly Asn Val Pro Gly Lys Ala Thr
      15                  20                  25

ACC GAC CAG AAG CTG CTG GAG CAG CTT GGC TTC AAG GCA                                              246
Thr Asp Gln Lys Leu Leu Glu Gln Leu Gly Phe Lys Ala
  30                    35                  40

GTC GCC GCG AAC CTG CTG GAC AAG GCC GCG AAG TTC AAG ATC                                          294
Val Ala Ala Asn Leu Leu Asp Lys Ala Ala Lys Phe Lys Ile
        45                  50                  55                  60

TTC GAG GCC TTC TCC GAG TCC AAG GGC CTC CTC CTC ACC TCC                                          342
Phe Glu Ala Phe Ser Glu Ser Lys Gly Leu Leu Leu Thr Ser
        65                  70                  75
```

```
                                                                                                  390
GCC  AAG  GCA  CCC  GGC  CTC  ATC  CCC  AAG  CTC  GAC  ACC  GCC  TAC  GAC
Ala  Lys  Ala  Pro  Gly  Leu  Ile  Pro  Lys  Leu  Asp  Thr  Ala  Tyr  Asp
          80                       85                      90

438
GTC  TAC  AAG  GCC  GCC  GAG  GGC  GCC  GAG  ACC  CCC  GCC  AAG  TAC  GAC
Val  Tyr  Lys  Ala  Ala  Glu  Gly  Ala  Glu  Thr  Pro  Ala  Lys  Tyr  Asp
     95                       100                      105

486
GCC  GTC  TTC  GCC  CTC  ACC  GAA  CTC  CCC  CGC  GTC  ATC  GGC  GCC
Ala  Val  Phe  Ala  Leu  Thr  Glu  Leu  Pro  Arg  Val  Ile  Gly  Ala
          110                      115                      120

534
CTC  GTC  CAC  ACC  AAG  GGT  GAG  CAG  GTC  ACC  GAG  GTC  CCT  GCT  GCT
Leu  Val  His  Thr  Lys  Gly  Glu  Gln  Val  Thr  Glu  Val  Pro  Ala  Ala
125                      130                      135                140

582
AAG  ATC  ACC  CTG  GAG  ATC  GTT  GAC  ATC  GAT  GCT  GCT
Lys  Ile  Thr  Leu  Glu  Ile  Val  Asp  Ile  Asp  Ala  Ala
                    145                      150                155

630
TTC  AAG  GCC  ATC  ACC  GCC  AAC  GCC  GCC  CCC  ACC  AAC  GAT  AAG
Phe  Lys  Ala  Ile  Thr  Ala  Asn  Ala  Ala  Pro  Thr  Asn  Asp  Lys
               160                      165                      170
```

```
TTC ACC GTC TTC GAG AGT GCC TTC AAC AAG GCC CTC AAT GAG TGC ACG        678
Phe Thr Val Phe Glu Ser Ala Phe Asn Lys Ala Leu Asn Glu Cys Thr
        175                 180                 185

GGC GGC GCC TAT GAG ACC TAC AAG TTC ATC CCC TCC CTC GAG GCC GCG        726
Gly Gly Ala Tyr Glu Thr Tyr Lys Phe Ile Pro Ser Leu Glu Ala Ala
        190                 195                 200

GTC AAG CAG GCC TAC GCC GCC ACC GTC GCC GCC GCG CCC GAG GTC AAG        774
Val Lys Gln Ala Tyr Ala Ala Thr Val Ala Ala Ala Pro Glu Val Lys
        205                 210                 215             220

TAC GCC GTC TTT GAG GCC GCG CTG ACC AAG GCC ATC ACC GCC ATG ACC        822
Tyr Ala Val Phe Glu Ala Ala Leu Thr Lys Ala Ile Thr Ala Met Thr
                        225                 230                 235

CAG GCA CAG AAG GCC GGC AAA CCC GCT GCC GCC GCT GCC ACA GGC GCC        870
Gln Ala Gln Lys Ala Gly Lys Pro Ala Ala Ala Ala Ala Thr Gly Ala
                240                 245                 250

GCA ACC GTT GCC ACC GGC GCC GCA ACC GCC GCC GCC GGT GCT GCC ACC        918
Ala Thr Val Ala Thr Gly Ala Ala Thr Ala Ala Ala Gly Ala Ala Thr
                        255                 260                 265

GCC GCT GCT GGT GGC TAC AAA GCC TGATCAGCTT GCTAATATAC TACTGAACGT       972
Ala Ala Ala Gly Gly Tyr Lys Ala  *
                270                 275

ATGTATGTGC ATGATCCGGG CGGCGAGTGG TTTTGTTGAT AATTAATCTT CGTTTTCGTT     1032

TCATGCAGCC GCGATCGAGA GGGCTTGCAT GCTTGTAATA ATTCAATATT TTTCATTTCT     1092

TTTTGAATCT GTAAATCCCC ATGACAAGTA GTGGGATCAA GTCGGCATGT ATCACCGTTG     1152

ATGCGAGTTT AACGATGGGG AGTTTATCAA AGAATTTATT ATTAAAAAAA AAAAAAAAAA     1212

AAAAAAAAAA AAAAAA                                                    1229
```

Fig. 3c

```
GAATTCCCCCA ACGCAAGAGC AGCA ATG GCG GTG CAG AAG CAC ACG GTG GCG        51
                             Met Ala Val Gln Lys His Thr Val Ala
                             -25                 -20

CTT TTC CTC GTG GCC CTC GTG GCC CTC TTC TAC GCT                         99
Leu Phe Leu Val Ala Leu Val Ala Ser Tyr Ala
-15              -10              -5

GCG GAT GCT GGC TAT GCC GCG GGC CCG GCC CCG                            147
Ala Asp Ala Gly Tyr Ala Ala Gly Pro Ala Pro
  1              5              10          15

GCT ACT GCC ACC CCC GCC ACT CCC GCT ACT CCC GCA                        195
Ala Thr Ala Thr Pro Ala Thr Pro Ala Thr Pro Ala
         20              25              30

GCC GTG CCA GGG TCA AAG GCC ACC CCC AAG CTG ATC GAG                    243
Ala Val Pro Gly Ser Lys Ala Thr Pro Lys Leu Ile Glu
         35              40              45

AAG ATC AAC GCC TTC AAG GCC GAG GAG GCA GCC GTC GTC                    291
Lys Ile Asn Ala Phe Lys Ala Glu Glu Ala Ala Val Val
    50              55              60

CCA GCT GAC TAC AAG TTC GTC GAA ACC TTC GGC ACG GCC                    339
Pro Ala Asp Tyr Lys Phe Val Glu Thr Phe Gly Thr Ala
65              70              75              80
```

Fig. 10a-1

```
ACC AAG GCC TTC GTT GAG GGC CTC GCG TCC GGC TAC GCC GAT CAA       387
Thr Asn Lys Ala Phe Val Glu Gly Leu Ala Ser Gly Tyr Ala Asp Gln
             85              90              95

AGC AAG AAC CAG CTC ACC TCC AAG CTC GAC GCC TTA AAG CTC GCT       435
Ser Lys Asn Gln Leu Thr Ser Lys Leu Asp Ala Leu Lys Leu Ala
            100             105             110

TAC GAG GCT CAG GGC GCC ACT CCC GAG GCC AAG TAC GAT GCC TAC       483
Tyr Glu Ala Gln Gly Ala Thr Pro Glu Ala Lys Tyr Asp Ala Tyr
        115             120             125

GTC GAG GCT CTC ACC GAG GCC CGC CTC GTC ATC GCC GGC ACC CTC GAG   531
Val Glu Ala Leu Thr Glu Ala Arg Leu Val Ile Ala Gly Thr Leu Glu
        130             135             140

GTC CAC GCC GTA AAG CCC GAG GCC AAG GTC GGC GAG CTC GCC ATC       579
Val His Ala Val Lys Pro Glu Ala Lys Val Gly Glu Leu Ala Ile
145             150             155             160
```

```
CCC GCC GAG GTG CAG CTC ATC GAC AAG GTC GAC GCC TAC AGG                           627
Pro Ala Glu Val Gln Leu Ile Asp Lys Val Asp Ala Tyr Arg
            165             170             175

ACC GCC GCC ACT GCC AAC CCC AAC GAC AAG TTC ACC                                   675
Thr Ala Ala Thr Ala Asn Pro Asn Asp Lys Phe Thr
        180             185             190

GTC TTC GAG AAC ACC TTT AAT GCC ATC AAG GTG AGC GGC GCC                           723
Val Phe Glu Asn Thr Phe Asn Ala Ile Lys Val Ser Gly Ala
        195             200             205

GCC TAC AGC TTC AAG TAC AAG CAG CTT GTG CCC CTG AAG                               771
Ala Tyr Ser Phe Lys Tyr Lys Gln Leu Val Pro Leu Lys
210             215             220

CAG GCC GCC CAG AAA AAG GCC GCG ACT GAG GCC GTC AAG                               819
Gln Ala Ala Gln Lys Lys Ala Ala Thr Glu Ala Val Lys
225             230             235             240

GTC TCT GAG ACC CTG AAA AAG GCT GCC ATG TCA GAG GCC                               867
Val Ser Glu Thr Leu Lys Lys Ala Ala Met Ser Glu Ala
    245             250             255

GAG AAG GAG GCC ACC CCC GCC GCT ACA CCA GCC CCC                                   915
Glu Lys Glu Ala Thr Pro Ala Ala Thr Pro Ala Pro
260             265             270
```

```
GCG GCT GCC ACC GCC ACC GCA ACC CCC GCC ACC GCT GCC ACC GCT           963
Ala Ala Ala Thr Ala Thr Ala Thr Pro Ala Tyr Ala Thr Ala
            275             280             285

ACC CCC GCT GCC ACC GCC ACC GCA ACC GCC ACC CCC GCC ACC GCA          1011
Thr Pro Ala Ala Thr Ala Thr Ala Thr Ala Thr Pro Ala Thr Ala
    290             295             300

ACC CCC GCT GCT GGT GGC TAC AAA GTC TGATCAACTC TAACGGTATA            1061
Thr Pro Ala Ala Gly Gly Tyr Lys Val
    305             310

CATCCATCAT GCACATATAC TAACTCCGTAT CTATGTGCAT GGCATGGCCCG TGGGGTCGAG  1121

CGATTTAGCT GATAATTCAT TCTTGGTTTT CGTTTCATGC ATCCCGCGCC CATCAAGCGC   1181

GTGCATGGTC AATTGTTTAT GTAATATTTG TTTTCGATG TAAAACTAGG CCTGCGTGCC    1241

ACGGCTACTCG ACTAATTAAT GAACCGTTTT CACCTTTAAA AAAAAAGGA ATIC         1295

```
Clone 19R- GGCCACCAACAAGGCCCTTCGTTGAGGGCCCTCCGGCTACGCCGATC --- -385
Clone 12R- G-CCTTCTCCGAGTCCTCCA---AGGGCCTCCTCGCCACCTCCGCCGC-C --- -348
Clone 19R- AAAGCAAGAACCAGCT-CACCTCCAAGCTCCGACCCCTTAAAGCTCGC --- -434
Clone 12R- AAGGC---ACCCGGCCCTCATCCCCAAGCTCCGACACCCCTACGCCTCGC --- -395
Clone 19R- TTACGAGGCTGCCCCAGGGCGCCACTCCCGAGGCCAAGTACGATGCCTACG --- -484
Clone 12R- CTACAAGGCCCCGCCCAGGGCCCACCCCGAGGCCAAGTACGACGCCTTCG --- -445
Clone 19R- TCGCCCACCCTCACCCGAGCCGCTCCCGCGTCATCGCCCACCCCTCGAGGTC --- -534
Clone 12R- TCACTGCCCCTCACCCGAAGCGCTCCGCGTCATCGCCCGGCCCCTCGAGGTC --- -495
Clone 19R- CACGCCCGAGGTCAAGCCCGCCACCCGAGGAGGTCGGCGCCA-TCCCCG --- -583
Clone 12R- CACGCCCGTCAAGCCCCGCCAGCCGAGGAGGTCCCTG-CTGCTAAGATCCCCA --- -544
Clone 19R- CCGCCCGAGGTGCAGCTCATCGACAAGGTCGACGCCGCCGTACAGGACCGCC --- -633
Clone 12R- CCGGTGAGCTGCAGATCGTTGACAAGATCGATGCTGCCTTCAAGATCGCA --- -594
Clone 19R- GCCACTGCCCGCCCAACGCCCCCAACGACAAGTTCACCCGTCTTCGA --- -683
Clone 12R- GCCACCGCCCCGCCAACGCCCCCAACAACGATAAGTTCACCCGTCTTCGA --- -644
```

Fig. 12a-2

```
Clone 19R- GAACACCTTTAACAATGCCATCAAGGTGAGCCTGGGCCGCCTACGACA          -733
Clone 12R- GAGTGCCTTCAACAAGGCCCTCAATGAGTGCACGGCCGGCCCCTATCAGA          -694
Clone 19R- GCTACAAGTTCATCCCCCACCCTTGTGGCCCGGGCCGTCAAGCAGGCCTACGCC       -783
Clone 12R- CCTACAAGTTCATCCCCCTCCCTCGAGGCCCCGGGCCGGTCAAGCAGGCCTACGCC     -744
Clone 19R- GCCAAGCAGGCCACCCGGCCGGAGGTCAAGTACACTGTCTCTGAGACCGC           -833
Clone 12R- GCCACCCGTCGCCGCCGCCCCGGCCCCGGAGGTCAAGTACGCGCCGTCTCTTTGAGCCCGC -794
Clone 19R- GCTGAAAAAGGCCCGTCACTGCAATGTCAGAGAGGCCGACACAGAGGCCACGC        -883
Clone 12R- GCTGACCAAGGCCATCACCCGCCCCAGGCCCATGACCCGGCCACAGAAGCCCGCCAAAC  -844
Clone 19R- CCGCC---GCGGCCTGCCCGCCAACACCCCGGCCTACCCCGCTGCCAC             -930
Clone 12R- CCGCTGCCCGGCCGCCTGCCCGCCACAGGCCCGCCAAC---CCT---TGCCACCCGGC   -888
Clone 19R- ACCGCAACCCCGGCCCCGCTACGCCCCCGCTACCCCGCTGCCAC                 -980
Clone 12R- GCCGGCAACCGGCCCGCCGCCGG-T-----GCTGCCACCCGCCGCTGCTGG          -929
Clone 19R- CGCCACCGGCAACCCCCGCCCCGCTG-CCACCGCAACCCCGCGCC-GCTGCTGG       -1028
Clone 12R- TGGCTACAAAGCCTGATCAGCTTGCTAATATA-CTACTGAACG-TA-TGT           -976
```

Fig. 12b-1

```
Clone 19R- TGGCTACAAAGTCTGATCAACTCTAACGGTATATATCCATCATGCACATA
             ||| ||||||||||||||||  |||||||||||| |||||||||||||
Clone 12R- ATG-TGCATGATCCGGGCGGCG--AGTGGT-TTTGTTGATAATT-A-ATC    -1078
                                                                  -1020

Clone 19R- TACTAACTCGTATCTATGTGCATGGCCATGGCCCTGGGGTCCAGCCGATTTA
           ||| |||||||  ||  ||| |||  ||||  ||| ||  |||||||||
Clone 12R- TTCGTTTTCGTTC-AT--GCA-GCCGCGATCGAGAGGGCTTGC-ATGCT     -1128
                                                                  -1065

Clone 19R- GCTGATAATTCATTCTTGGTT--TTCGTTTCATGCATCCGGCGCCATCA
           | |||||||||||| ||||||  ||| ||||  || ||   |||| |
Clone 12R- TGTAATAATTCAATATTTTTCATTTCTTTT--TGAATCTGTAAATCCCCA    -1176
                                                                  -1113

Clone 19R- AGC-GCCTGCATGGT-CAATTGTTTATGTAATATTTGTTTTTC-GATGTA
           ||| ||| |||  || || ||||| ||||  ||||||||   |  |||
Clone 12R- TGACAAGTAGTGGGATCAAGTCGGCATGTATCACC-GTTGATGCCGA-GTT   -1223
                                                                  -1161

Clone 19R- AAACTAG-GCCTGCGTGCCACGCTACTCGACTAATTAATGAACCGTTTTC
           ||  |||  ||||| || |    |   ||||||| ||| |||  |||
Clone 12R- TAACGATGGGGAGTTTATCAAAGAATTT-ATTA-TTAAAAAAAAAAAAA    -1272
                                                                  -1209

Clone 19R- ACCTTTAAAAAAAAAAGGAATTC      -1295
           ||  |||||   ||||||||||
Clone 12R- AAA---AAAAAAAAAAAAAAAA        -1229
```

Fig.12b-2

```
Clone 19R-  MAVQKHTVALFLAVALVAGPAASYAADAGYAPATPATPAAAPATAATPATP              -50
              -|---|||||||||||||||||||||---|||||-|--------|---
Clone 12R-  MAVQKYTVALFLAVALVAGPAASYAADAGY-----------TPAAAATP              -38

Clone 19R-  ATPATPAAVPSGKATTEECKLIEKINAGFKAAVAAAAVVPPADKYKTEVE             -100
              -|-s|-|-----|---|-s|-|--s|-|||-|--s|--||-|-|----
Clone 12R-  ATPAATPAAAGGKATTDEQKLLEDVNAGFKAAVAAAANAPPADKFKIFEA              -88

Clone 19R-  TFG---------TATNKAFVEGLASGYADQSKNQLTSKLDAALKLAYEAAQ            -162
              s|--------|ss|-||--|--|--s|--s|--s|-|-s|--|-|---
Clone 12R-  AFSESSKGLLATSAAKAPG--------------LIPKLDTAYDVAYKAAE             -124

Clone 19R-  GATPEAKYDAYVATLTEALRVIAGTLEVHAVKPAAEEVKVGAIPAAEVQL             -192
              ||||||||-||-|||||||-|s|-|||||||-|-|-s|-|-s|-|-s|-s
Clone 12R-  GATPEAKYDAFVTALTEALRVIAGALEVHAVKPATEEVPAAKIPIGELQI             -174

Clone 19R-  IDKVDAAYRTAATAANAAPANDKFTVFENTFNNAIKVSLGAAYDSYKFIB             -242
              s|---s|-s---|-----|-----|s---s|-s-s-ss-|-|---|---
Clone 12R-  VDKIDAAFKIAATAANAAPTNDKFTVFESAFNKALNECTGGAYETYKFIP             -224

Clone 19R-  TLVAAVKQAYAAKQATAPEVKYTVSETALKKAVTAMSEASKEATPAAAAT             -292
              s|--|||||-|--s|-|--|--|s-||-s|-s|---|-|-s---|---
Clone 12R-  SLEAAVKQAYAATVAAAPEVKYAVFEAALTKAITAMTQAQKAGKPAAAA-             -233

Clone 19R-  ATPTPAAAATATATPAAAYATATPAAAATATATPAAATATATPAAAGCYKV            -339
              ------------------s-s|------|---|s--|---|-------
Clone 12R-  ------------------ATGAATVATGAATAAAGAAT--AAAGGYKA              -301
```

Fig. 13

| PEPTIDES PATIENTS | 19R | 12R | 1-47 E8 | 58-128 m8 | 76-179 mE7 | 111-195 E14 | 131-237 E2 | 172-240 E5 | 199-254 E4 |
|---|---|---|---|---|---|---|---|---|---|
| 1 | ▨ | ▨ | - | ░ | ░ | ░ | ░ | ░ | ░ |
| 2 | ▨ | ▨ | - | ░ | ░ | ░ | - | - | ░ |
| 3 | ▨ | ▨ | - | - | - | - | - | - | - |
| 4 | - | - | - | - | - | - | - | - | - |
| 5 | - | - | - | - | - | - | - | - | - |
| 6 | - | - | - | - | - | - | - | - | - |
| 7 | ▨ | ▨ | - | ░ | ░ | ░ | ░ | ░ | - |
| 8 | ▨ | ▨ | - | - | ░ | ░ | ░ | - | - |
| 9 | ▨ | ▨ | - | ░ | ░ | ░ | ░ | ░ | ░ |
| 10 | ▨ | ▨ | - | - | ░ | ░ | ░ | ░ | ░ |
| 11 | ▨ | ▨ | - | - | ░ | ░ | ░ | ░ | ░ |
| 12 | ▨ | ▨ | - | - | ░ | ░ | ░ | ░ | ░ |
| 13 | ▨ | ▨ | - | - | ░ | ░ | ░ | ░ | ░ |
| 14 | ▨ | ▨ | - | - | ░ | ░ | ░ | ░ | ░ |
| 15 | ▨ | ▨ | - | - | ░ | ░ | ░ | - | ░ |
| 16 | - | - | - | - | - | - | - | - | - |
| 17 | ▨ | ▨ | - | - | ░ | ░ | ░ | - | - |
| 18 | ▨ | ▨ | - | - | ░ | ░ | ░ | - | - |

RYEGRASS POLLEN ALLERGEN

REFERENCE TO RELATED APPLICATIONS

This application is a divisional of U.S. patent application Ser. No. 08/195,947 filed Feb. 14, 1994, which is a continuation of application Ser. No. 07/930,060, filed Aug. 14, 1992, now abandoned, which is a continuation-in-part of U.S. application Ser. No. 07/746,702 filed Aug. 16, 1991, now abandoned which is, in turn, a continuation-in-part of U.S. application Ser. No. 07/585,086 filed Oct. 26, 1990, now abandoned, the disclosure of all of which are hereby incorporated by reference.

FIELD OF THE INVENTION

The present invention relates to allergenic proteins from pollen of ryegrass, *Lolium perenne* L., and fragments, derivatives and homologues thereof, and to allergenic proteins immunologically related thereto. More particularly, the present invention relates to the major allergenic protein family Lol p Ib from pollen of ryegrass and related proteins of the Lol p Ib protein family.

BACKGROUND OF THE INVENTION

Genetically predisposed individuals, who make up about 10% of the population, become hypersensitized (allergic) to antigens from a variety of environmental sources to which they are exposed. Those antigens that can induce immediate and/or delayed types of hypersensitivity are known as allergens. (King, T. P., *Adv. Immunol.* 23 77–105 (1976) Anaphylaxis or atopy, which includes the symptoms of hay fever, asthma, and hives, is one form of immediate allergy. It can be caused by a variety of atopic allergens, such as products of grasses, trees, weeds, animal dander, insects, food, drugs and chemicals.

The antibodies involved in atopic allergy belong primarily to the IgE class of immunoglobulins. IgE bonds to mast cells and basophils. Upon combination of a specific allergen with IgE bound to mast cells or basophils, the IgE may be cross-linked on the cell surface, resulting in the physiological effects of IgE-antigen interaction. These physiological effects include the release of, among other substances, histamine, serotonin, heparin, a chemotactic factor for eosinophilic leukocytes and/or the leukotrienes, C4, D4 and E4, which cause prolonged constriction of bronchial smooth muscle cells (Hood, L. E. et al. *Immunology*, 2nd ed.) The Benjamin/Cumming Publishing Co., Inc., (1984). These released substances are the mediators which result in allergic symptoms caused by a combination of IgE with a specific allergen. Through them, the effects of an allergen are manifested. Such effects may be systematic or local in nature, depending on the route by which the antigen entered the body and the pattern of deposition of IgE on mast cells or basophils. Local manifestations generally occur in epithelial surfaces at the location at which the allergen entered the body. Systemic effects can include anaphylaxis (anaphylactic shock), which is the result of an IgE-basophil response to circulating (intravascular) antigen.

Allergens constitute the most abundant proteins of grass pollen, which is the major cause of allergic disease in temperate climates (Marsh (1975) Allergens and the genetics of allergy; in M. Sela (ed), The Antigens, Vol. 3, pp 271–359, Academic Press Inc., London, N.Y.)., Hill et al. (1979) Medical Journal of Australia 1, 426–429). The first descriptions of the allergenic proteins in ryegrass showed that they are immunochemically distinct, and are known as groups I, II, III and IV (Johnson and March (1965) Nature, 206, 935-; and Johnson and Marsh (1966) Immunochemistry 3, 91–100). Using the International Union of Immunological Societies' (IUIS) nomenclature, these allergens are designated Lol p Ib, Lol p II, Lol p III and Lol p IV. However, the allergenic spectrum of ryegrass pollen is now known to be more complex. The international reference preparation for ryegrass contains 17 allergens ranging in molecular weight from 12 to 89 kD (Stewart et al. (1988) Int. Arch. Allergy Appl. Immunol. 86: 9–18). These allergenic proteins in pollen have been detected by their ability to bind IgE, the immunoglobulin specifically present in allergic individuals.

Among these allergens, Lol p I, II, III and IV have been extensively studied. The full amino acid sequences of Lol pII and III have been reported. This is made possible by using standard biochemical techniques due to the high amount of allergenic proteins in the pollen and the relatively small molecular weight of the proteins. Although the proteins of Lol p I and IV are abundant in the pollen, only partial amino acid sequences had been reported using the same techniques. This is due to the relatively high molecular weight of the proteins. In addition, it is difficult to purify allergens without any cross-contamination and is labor-intensive. Lack of primary sequence and highly purified allergens in sufficient quantity have been the limiting factor in the development of both therapeutic and diagnostic products for the treatment and diagnosis of type I allergies.

Lol p I is defined as an allergen because of its ability to bind to specific IgE in sera of ryegrass-sensitive patients, to act as an antigen in IgG responses and to trigger T-cell responses. The allergenic properties have been assessed by direct skin testing of grass pollen-sensitive patients. The results showed that 84% had a skin sensitivity to Lol pI (Freidhoff et al., (1986) J. Allergy Clin. Immunol. 78: 1190–1201), demonstrating the primary importance of this protein as the major allergen. Furthermore, 95% of patients demonstrated to be grass pollen-sensitive possessed specific IgE antibody that bound-to Lol pI, as demonstrated by immunoblotting (Ford and Baldo (1986) International Archives of Allergy and Applied Immunology 81: 193–203).

Substantial allergenic cross-reactivity between grass pollens has been demonstrated using an IgE-binding assay, the radioallergo-sorbent test (RAST), for example, as described by Marsh et al. (1970) J. Allergy, 46, 107–121, and Lowenstein (1978) Prog. Allergy, 25, 1–62. (Karger, Basel).

The immunochemical relationship of Lol p I with other grass pollen antigens have been demonstrated using both polyclonal and monoclonal antibodies (e.g. Smart and Knox (1979) International Archives of Allergy and Applied Immunology 62: 173–187; Singh and Knox (1985) International Archives of Allergy and Applied Immunology 78, 300–304). Antibodies have been prepared to both purified proteins and IgE-binding components. These data demonstrate that the major allergen present in pollen of closely related grasses is immunochemically similar to Lol p I (Singh and Knox, supra).

SUMMARY OF THE INVENTION

In accordance with the present invention, it has been discovered that the ryegrass pollen allergen Lol pI comprises two proteins, designated as herein Lol p Ia and Lol p Ib. The Lol p Ib ryegrass pollen allergen is present in *L. perenne* as a family of proteins. The genes encoding two family members of Lol p Ib, designated Lol p Ib.1 and Lol p Ib.2 have now been identified. Family member Lol p Ib.1 was previously designated Lol p Ib and is now referred to as Lol p Ib.1. As used herein, Lol p Ib thus refers to a major ryegrass pollen protein allergen which is actually a family of closely related proteins having similar structure and function but encoded by separate genes. Therefore, the terms Lol p Ib and Lol p Ib family members may be used herein interchangeably.

The present invention provides purified nucleic acid sequences coding for at least one Lol p Ib ryegrass pollen allergen, or at least one antigenic fragment thereof, or derivative or homologue thereof, or the functional equivalent of said nucleic acid sequence. The present invention also provides expression vectors comprising a nucleic acid sequence coding for at least one Lol p Ib ryegrass pollen allergen, or at least one antigenic fragment thereof, or derivative or homologue thereof, or the functional equivalent of said nucleic acid sequence. The present invention further provides host cells transformed to express a protein or peptide encoded by the nucleic acid sequences of the invention.

Another aspect of the present invention provides at least one purified Lol p Ib ryegrass pollen allergen, or at least one antigenic fragment thereof, or derivative or homologue. A further aspect of the present invention provides an isolated antigenic fragment of an allergen from ryegrass pollen, preferably from a Lol p Ib ryegrass pollen allergen. More preferably the ryegrass pollen allergen is Lol p Ib.1 or Lol p Ib.2.

Still another aspect of the invention provides a modified ryegrass pollen protein allergen which, when administered to a ryegrass pollen-sensitive individual, reduces the allergic response of the individual to ryegrass pollen. Preferably the ryegrass pollen allergen is a modified Lol p Ib protein or derivative or homologue thereof. More preferably the ryegrass pollen allergen is a modified Lol p Ib.1 or Lol p Ib.2 protein or derivative or homologue thereof. The present invention also provides at least one modified fragment of ryegrass pollen protein allergen which, when administered to a ryegrass pollen-sensitive individual, reduces the allergic response of the individual to ryegrass pollen. Preferably the ryegrass pollen allergen is a Lol p Ib ryegrass pollen allergen, more preferably Lol p Ib.1 or Lol p Ib.2 Isolated protein allergen or antigenic fragment thereof immunologically related to Lol p Ib.1 or Lol p Ib.2, or fragment or derivative or homologue of Lol p Ib.1 or Lol p Ib.2 is also provided by the present invention.

In yet another aspect of the present invention, there is provided non-native (i.e., recombinant or chemically synthesized) Lol p Ib family members or their derivatives or homologues, or a non-native allergenic protein immunologically cross-reactive to antibodies to one or more Lol p Ib family members or their derivatives or homologues. The present invention also provides purified native Lol p Ib proteins or at least one fragment or derivative or homologue thereof.

Non-native Lol p Ib protein, and fragments or portions derived therefrom (peptides) can be used in methods of diagnosing, treating and preventing allergic reactions to ryegrass pollen. Purified native Lol p Ib protein, fragments thereof, and homologues or derivatives thereof are also useful in methods of diagnosing, treating and preventing allergic reactions to ryegrass pollen.

Still yet another aspect of the present invention relates to antibodies to non-native Lol p Ib or derivatives or homologues thereof as well as antibodies raised against purified native Lol p Ib or derivatives or homologues thereof.

Further features of the present invention will be better understood from the following detailed description of the preferred embodiments of the invention in conjunction with the appended figures.

BRIEF DESCRIPTION OF THE FIGURES

FIG. 1 shows isolation of cDNA clones specific for the Poaceae Group Ib allergens.

FIG. 2 shows tissue-type and cell-type specific expression of group Ib allergen transcripts.

FIG. 3 shows the cDNA sequence, predicted amino acid sequence and hydrophilicity profile of rye-grass pollen clone 12R, designated Lol p Ib.1. FIGS. 3b and 3c show the nucleotide and deduced amino acid sequence of the 1229 nucleotide EcoRI cDNA insert lambda-12R (SEQ ID NO:1 and SEQ ID NO:2). The deduced amino acid sequence represented by the single letter code is shown below the DNA sequence, and begins at the first potential in-frame initiation codon at nucleotide 40. One uninterrupted open reading frame continues for 301 amino acids (numbered below the DNA sequence) and ends with the TGA stop codon denoted by an asterisk. The putative signal peptide is indicated by negative numbers. The amino acid residues 1–9, 12–17, and 19 were identified by N-terminal sequencing.

FIG. 4a: IgE antibodies; FIG. 4b, MAb 40.1 and FIG. 4c, MAb 12.3. Controls for FIGS. 4a–c are provided by bacteria transformed with non-recombinant plasmids.

FIG. 5 shows detection of Lol p Ia and Lol p Ib in mature pollen of rye-grass using specific MAbs and immunogold probes.

FIGS. 10a and 10b show the cDNA sequence and predicted amino acid sequence of Lol p Ib.2 (clone 19R) (SEQ ID NO:3 and SEQ ID NO:4).

FIGS. 12a and 12b are a representation showing comparison of the cDNA sequences of Lol p Ib.2 (clone 19R) (SEQ ID NO:3) and Lol p Ib.1 (clone 12R) (SEQ ID NO:1). A bar is used to show identity between DNA sequences. Gaps are inserted within the translated region to show maximum similarity. The number of gaps inserted in clone 19R is 14. The number of gaps inserted in clone 12R is 35. Overall sequence identity is 887 bases (72.2%).

FIG. 13 is a representation comparing amino acid sequences of Lol p Ib.2 (clone 19R) (SEQ ID NO:4) and Lol p Ib.1 (clone 12R) (SEQ ID NO:2). Gaps are inserted within the translated region to show maximum similarity. A bar is used to show identity between amino acid sequences and "s" shows similarity between amino acid sequences. Amino acids said to be "similar" are A, S and T; D and E; N and Q; R and K; I, L, M and V; and F, Y and W. The number of gaps inserted in clone 19R is 1. The number of gaps inserted in clone 12R is 4. The two sequences contain 201 identical amino acids (66.8%), and 38 "similar" amino acids (12.6%)

FIG. 14 shows tissue-specific expression of clone 19R.

FIG. 22 shows identification of allergenic and antigenic epitopes of Lol p Ib.1 based on dot immunoassays of overlapping sequential synthetic peptides. FIG. 22(a) shows the IgE binding from 16 positive sera from a total of 50 ryegrass pollen allergic patients (RAST≧4). FIG. 22(b) shows monoclonal or polyclonal antibody binding. The values are arbitrary densitometric units of the intensity of the dot blot, measured by Pharmacia LKB UltraScan XL, Sweden. Densitometric values ≧ were considered as positive binding in comparison to the background. For every peptide the sera and antibody values have been added (score/peptide) and divided by the number of positive sera or antibody to express the final value as an average (score/sera or antibody). Sera C1 and C2 were used as negative controls. C refers to crude ryegrass pollen extract (1 µg/dot) as positive control.

DETAILED DESCRIPTION OF THE INVENTION

The data herein show that what was considered to be the major allergen of rye-grass pollen, Lol p I, actually comprises at least two different allergenic proteins: Lol p Ia, which comprises 4 different isoforms in the 35 kD range with pIs ranging from about 5.5–7.0 and Lol p Ib, which comprises at least 5 different isoforms of 31/33 kD proteins, and pIs ranging from 6.0–10.6. Lol p Ib has a different primary structure and composition from Lol p Ia, as deduced from $NH_2$-terminal amino acid sequence and the absence of allergenic cross-reactivity. cDNA clones encoding Lol p Ib.1 (clone 12R) (SEQ ID NO:1) and Lol p Ib.2 (clone 19R) (SEQ ID NO:3) have been isolated and characterized. The Lol p Ib protein encoded by clones 12R and 19R have a different primary structure and composition from Lol p Ia, as deduced by cDNA cloning and the absence of allergenic cross-reactivity. The $NH_2$-terminal sequence of recombinant Lol p Ib.1 is identical to that determined for purified native Lol p Ib. However, Lol p Ib.1 and Lol p Ib.2 are apparently acidic proteins, having a predicted pI of 5.16 and 5.9, respectively. Purified native Lol p Ib, Lol p Ib.1 and Lol p Ib.2 are non-glycosylated proteins with similar molecular weights (31/33 kD) and similar $NH_2$- terminal sequences. These similarities suggest that the genes encoding the native Lol p Ib and recombinant Lol p Ib proteins will be different members of the same gene family. Lol p Ib family members are synthesized in pollen as a preallergen with a 25 amino acid signal peptide that targets the allergen to plastids. This is followed by cleavage of the peptide, and in mature pollen the allergen occurs predominantly in the starch grains.

Figure 3A:
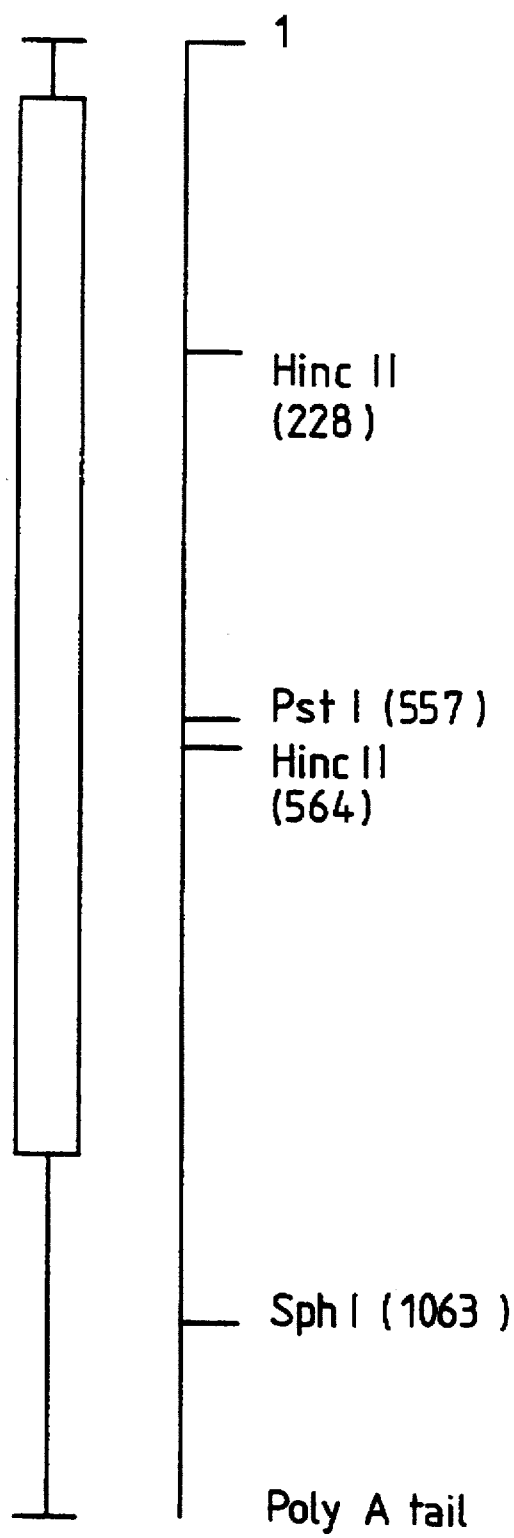
FIG. 3a shows a schematic restriction map of lambda-12R cDNA. The hatched box represents the predicted translation open reading frame.

Thus, one aspect of the present invention provides purified nucleic acid sequences coding for at least one Lol p Ib ryegrass pollen allergen, or at least one antigenic fragment thereof, or derivative or homologue thereof, or the functional equivalent of such nucleic acid sequence. Preferred nucleic acid sequences coding for Lol p Ib family members include the nucleic acid sequence encoding amino acids –25 through 276 of Lol p Ib.1 as shown in FIGS. 3b and 3c (SEQ ID NO:1), and the nucleic acid sequence encoding amino acids –25 through 314 of Lol p Ib.2 shown in FIGS. 10a and 10b (SEQ ID NO:3). These sequences encode the entire Lol p Ib.1 protein (SEQ ID NO:2) and Lol p Ib.2 protein (SEQ ID NO:4), including the 25 amino acid signal peptide. Other preferred nucleic acid sequences include the nucleic acid sequence encoding amino acids 1-276 of Lol p Ib.1 shown in FIGS. 3b and 3c, and the nucleic acid sequence encoding amino acids 1-314 of Lol p Ib.2 shown in FIGS. 10a and 10b. These nucleic acid sequences encode the mature Lol p Ib.1 and Lol p Ib.2 proteins. Still other nucleic acid sequences of the invention include nucleic acid sequences encoding at least one fragment of the coding portion of the nucleic acid sequence of Lol p Ib.1 shown in FIG. 3b–3c, or at least one fragment of the coding portion of the nucleic acid sequence of Lol p Ib.2 shown in FIGS. 10a and 10b, or the functional equivalent of such nucleic acid sequences.

The original source of the genetic material is fresh ryegrass pollen from Lolium perenne L., collected from field sources near Melbourne, Australia and bulk collected pollen from a supplier (Greer Laboratories, Lenoir, N.C.) and from flowerhead. These sources of pollen are not intended to limit the scope of the invention since they only represent one convenient supply of the pollen. The present invention can be practiced using pollen from any location.

"Gene", is used, in respect of the present invention, in its broadest sense and refers to any contiguous sequence of nucleotides, the transcription of which leads to a mRNA molecule, which mRNA molecule is capable of being translated into a protein. The gene encoding a Lol p Ib family member means the nucleotide sequence encoding the protein or derivatives or homologues of the protein which may contain single or multiple amino acid substitutions, deletions or additions. A Lol p Ib gene also refers to cDNAs complementary to the mRNAs corresponding to the full or partial length of a Lol p Ib protein.

It is expected that there are sequence polymorphisms in the nucleic acid sequence coding for each Lol p Ib family member, and it will be appreciated by one skilled in the art that one or more nucleotides in the nucleic acid sequence coding for a Lol p Ib family member may vary among individual L. perenne plants due to natural allelic variation. Any and all such nucleotide variations and resulting amino acid polymorphisms are within the scope of the invention. It may also be appreciated by one skilled in the art that Lol p Ib is a family of highly related genes whose proteins are present in L. perenne pollen (e.g. Rafnar et al. (1991) J. Biol. Chem. 266: 1229–1236; Silvanovich et al. (1991) J. Biol. Chem. 266: 1204–1210). Nucleotide sequences and corresponding deduced amino acid sequences of any and all such related family members including Lol p Ib.1 and Lol p Ib.2 are within the scope of the invention.

Accordingly, it is within the scope of the present invention to encompass all proteins belonging to the Lol p Ib family, at least one fragment (peptide) of a Lol p Ib protein family member, and amino acid derivatives thereof, and to encompass nucleotide sequences, including DNA, cDNA and mRNA and homologue or degenerate forms thereof, encoding Lol p Ib family members or fragments thereof, or derivatives thereof. It is also within the scope of the invention to encompass purified native Lol p Ib, at least one fragment (peptide) thereof, and derivatives or homologues thereof. It is further in accordance with the present invention to include molecules such as polypeptides fused to a Lol p Ib protein, or at least one fragment thereof, or derivatives thereof or to nucleotide sequences contiguous to such fragment and/or derivative-encoding nucleotide sequences. For example, for some aspects of the present invention, it is desirable to produce a fusion protein comprising a Lol p Ib family member or at least one fragment thereof or their derivatives and an amino acid sequence from another peptide or protein, examples of the latter being enzymes such as beta-galactosidase, phosphatase, urease and the like. Most fusion proteins are formed by the expression of a recombinant gene in which two coding sequences have been joined together such that their reading frames are in phase. Alternatively, proteins or peptides can be linked in vitro by chemical means. All such fusion protein or hybrid genetic derivatives of a Lol p Ib protein or its encoding nucleotide sequences are encompassed by the present invention. Furthermore, by homologues and derivatives of a Lol p Ib protein is meant to include synthetic derivatives thereof. The nucleotide sequences as elucidated herein, can be used to chemically synthesize the entire protein or generate any number of fragments (peptides) by chemical synthesis by well known methods (e.g. solid phase synthesis). All such chemically synthesized peptides are encompassed by the present invention. Accordingly, the present invention extends to isolated Lol p Ib protein family members, fragments thereof and their derivatives, homologues and immunological relatives made by recombinant means or by chemical synthesis.

The terms "isolated" and "purified" are used interchangeably herein and refer to peptides, protein, protein fragments, and nucleic acid sequences substantially free of cellular material or culture medium when produced by recombinant DNA techniques, or chemical precursors or other chemicals when synthesized chemically. The term "native purified" as used herein refers to proteins or fragments thereof purified from L. perenne pollen or other plant part. Furthermore, the present invention extends to proteins or fragments (peptides)

corresponding in whole or part to the nucleotide coding sequence given in FIGS. 3b and 3c and FIGS. 10a and 10b, or to degenerate or homologue forms thereof.

Fragments of nucleic acid within the scope of the invention include those coding for parts of Lol p Ib that elicit an immune response in mammals, preferably humans, such as the stimulation of minimal amounts of IgE; binding of IgE; eliciting the production of IgG and IgM antibodies; or the eliciting of a T cell response such as proliferation and/or lymphokine secretion and/or the induction of T cell anergy. The foregoing fragments of Lol p Ib are referred to herein as antigenic fragments. Fragments within the scope of the invention also include those capable of hybridizing with nucleic acid from other plant species for use in screening protocols to detect allergens that are cross-reactive with Lol p Ib protein. As used herein, a fragment of the nucleic acid sequence coding for Lol p Ib refers to a nucleotide sequence having fewer bases than the nucleotide sequence coding for the entire amino acid sequence of Lol p Ib and/or a mature Lol p Ib family member. Generally, the nucleic acid sequence coding for the fragment or fragments of a Lol p Ib family member will be selected from the bases coding for the mature Lol p Ib protein family member, however, in some instances it may be desirable to select all or a part of a fragment or fragments from the leader sequence portion of a nucleic acid sequence of the invention. A nucleic acid sequence of the invention may also contain linker sequences, restriction endonuclease sites and other sequences useful for cloning, expression or purification of a Lol p Ib protein or fragments thereof.

Antigenic fragments of an allergen from ryegrass pollen, preferably Lol p Ib.1, Lol p Ib.2, or purified native Lol p Ib, may be obtained, for example, by screening peptides produced by recombinant methods from the corresponding fragment of the nucleic acid sequence of the invention coding for such peptides, synthesized chemically using techniques known in the art, or by degrading of the purified allergen. The peptide fragments of the protein allergen may be obtained by any method known in the art such as chemical cleavage of the allergen, arbitrary division of the allergen into fragments of a desired length with no overlap of the peptides, or preferably division of the allergen into overlapping fragments of a desired length. The fragments are tested to determine their antigenicity and allergenicity. Fragments of recombinantly or synthetically produced Lol p Ib or of purified native Lol p Ib which are capable of eliciting a T cell response such as stimulation (i.e., proliferation or lymphokine secretion) and/or are capable of inducing T cell anergy are particularly desirable. Fragments of recombinantly or synthetically produced Lol p Ib or purified native Lol p Ib which do not bind immunoglobulin E (IgE) and/or which have minimal IgE stimulating activity are also desirable. If the fragment or fragments of a recombinantly or synthetically produced Lol p Ib protein family member or purified native Lol p Ib bind IgE, it is preferable that such binding does not lead to histamine release, e.g., such binding does not cause cross-linking of IgE on mast cells or basophils. Minimal IgE stimulating activity refers to IgE stimulating activity that is less than the amount of IgE production stimulated by whole recombinantly or synthetically produced Lol p Ib protein or whole purified native Lol p Ib protein. Preferred fragments also include antigenic fragments which, when administered to a ryegrass pollen-sensitive individual or an individual allergic to an allergen cross-reactive with ryegrass pollen allergen, are capable of modifying the allergic response to ryegrass pollen allergen of the individual, and antigenic fragments which, when administered to a ryegrass pollen-sensitive individual, are capable of modifying B-cell response, T-cell response or both B-cell and T-cell response of the individual to a ryegrass pollen allergen. As used herein modification of the allergic response of an individual sensitive to ryegrass pollen allergen can be defined as non-responsiveness or diminution in symptoms to the allergen, as determined by standard clinical procedures (see e.g. Varney et al, British Medical Journal, (1990), 302:265–269), including diminution in grass pollen induced asthmatic symptoms (Suphioglu et al. (1992) Lancet 339: 569–572).

Antigenic fragments of the present invention which have T cell stimulating activity, and thus comprise at least one T cell epitope are particularly desirable. T cell epitopes are believed to be involved in initiation and perpetuation of the immune response to a protein allergen which is responsible for the clinical symptoms of allergy. These T cell epitopes are thought to trigger early events at the level of the T helper cell by binding to an appropriate HLA molecule on the surface of an antigen presenting cell and stimulating the relevant T cell subpopulation. These events lead to T cell proliferation, lymphokine secretion, local inflammatory reactions, recruitment of additional immune cells to the site, and activation of the B cell cascade leading to production of antibodies. One isotype of these antibodies, IgE, is fundamentally important to the development of allergic symptoms and its production is influenced early in the cascade of events, at the level of the T helper cell, by the nature of the lymphokienes secreted. A T cell epitope is the basic element or smallest unit of recognition by a T cell receptor, where the epitope comprises amino acids essential to receptor recognition. Amino acid sequences which mimic those of the T cell epitopes and which modify the allergic response to protein allergens are within the scope of this invention.

Exposure of patients to purified protein allergens of the present invention or to the antigenic fragments of the present invention which comprise at least one T cell epitope and are derived from protein allergens may tolerize or anergize appropriate T cell subpopulations such that they become unresponsive to the protein allergen and do not participate in stimulating an immune response upon such exposure. In addition, administration of the protein allergen of the invention or an antigenic fragment of the present invention which comprises at least one T cell epitope may modify the lymphokine secretion profile as compared with exposure to the naturally-occurring protein allergen or portion thereof (e.g. result in a decrease of IL-4 and/or an increase in IL-2). Furthermore, exposure to such antigenic fragment or protein allergen may influence T cell subpopulations which normally participate in the response to the allergen such that these T cells are drawn away from the site(s) of normal exposure to the allergen (e.g., nasal mucosa, skin, and lung) towards the site(s) of therapeutic administration of the fragment or protein allergen. This redistribution of T cell subpopulations may ameliorate or reduce the ability of an individual's immune system to stimulate the usual immune response at the site of normal exposure to the allergen, resulting in a diminution in allergic symptoms.

Screening for IgE binding to the protein or fragments thereof may be performed by scratch tests or intradermal skin tests on laboratory animals or human volunteers, or in in vitro systems such as RAST (radioallergosorbent test), RAST inhibition, ELISA assay or radioimmunoassay (RIA).

The Lol p Ib family member Lol p Ib.1 has been divided into a number of overlapping peptides as shown in Table 4. Each of these peptides is also within the scope of the invention.

The present invention provides expression vectors and host cells transformed to express the nucleic acid sequences of the invention. Expression vectors of the invention comprise a nucleic acid sequence coding for at least one Lol p Ib ryegrass pollen allergen, or at least one antigenic fragment thereof, or derivative or homologue thereof, or the functional equivalent of such nucleic acid sequence. Nucleic acid sequences coding for Lol p Ib family members including Lol p Ib.1 or Lol p Ib.2, or at least one fragment thereof may be expressed in prokaryotic or eukaryotic host cells. Suitable host cells include bacterial cells such as $E.$ $coli$, insect cells, yeast, or mammalian cells such as Chinese hamster ovary cells (CHO). Suitable expression vectors, promoters, enhancers, and other expression control elements may be found in Sambrook et al. Molecular Cloning: A Laboratory Manual, second edition, Cold Spring Harbor Laboratory Press, Cold Spring Harbor, N.Y., 1989. Suitable vectors for expression in yeast include YepSec1 (Baldari et al. (1987) $Embo$ $J.$ 6: 229–234); pMF_ (Kurjan and Herskowitz (1982) $Cell$ 30: 933–943); and JRY88 (Schultz et al. (1987) $Gens$ 54: 113–123).

For expression in $E.$ $coli$, suitable expression vectors include pTRC (Amann et al. (1988) $Gene$ 69: 301–315); pET-11d (Novagen, Madison, Wis.); pGEX (Amrad Corp., Melbourne, Australia); pMAL (N.E. Biolabs, Beverly, Mass.); pRIT5 (Pharmacia, Piscataway, N.J.); and pSEM (Knapp et al. (1990) $BioTechniques$ 8: 280–281). The use of pTRC and pET-11d will lead to the expression of unfused protein. The use of pGEX, pMAL, pRIT5 and pSEM will lead to the expression of allergen fused to glutathione S-transferase (pGEX), maltose E binding protein (pMAL), protein A (pRIT5), or truncated β-galactosidase (PSEM). When a Lol p Ib protein family member, fragment, or fragments thereof is expressed as a fusion protein, it is particularly advantageous to introduce an enzymatic cleavage site at the fusion junction between the carrier protein and the Lol p Ib protein family member or fragment thereof. A Lol p Ib family member or fragment thereof may then be recovered from the fusion protein through enzymatic cleavage at the enzymatic site and biochemical purification using conventional techniques for purification of proteins and peptides. Suitable enzymatic cleavage sites include those for blood clotting Factor Xa or thrombin for which the appropriate enzymes and protocols for cleavage are commercially available from for example Sigma Chemical Company, St. Louis, Mo. and N.E. Biolabs, Beverly, Mass.

Host cells can be transformed to express the nucleic acid sequences of the invention using conventional techniques such as calcium phosphate or calcium chloride co-precipitation, DEAE-dextran-mediated transfection, or electroporation. Suitable methods for transforming the host cells may be found in Sambrook et al. supra, and other laboratory textbooks. The nucleic acid sequences of the invention may also be synthesized using standard techniques.

Accordingly, another aspect of the present invention provides a method of producing recombinant Lol p Ib.1 or Lol p Ib.2, or at least one fragment thereof, or their derivatives or homologues, or their immunological relatives (as hereinbefore defined) comprising culturing an organism containing a replicable recombinant DNA molecule, said molecule comprising a promoter capable of expression in said organism, a gene encoding a Lol p Ib family member, at least one fragment thereof, or homologue or derivative thereof, or immunological relatives thereof, located downstream of and transcribed from said promoter, a selectable marker and a DNA vehicle containing a prokaryotic or eukaryotic origin of replication, under conditions and for a time sufficient for said recombinant DNA molecule to be stably maintained and direct the synthesis of the Lol p Ib protein, at least one fragment thereof, or derivatives, homologues or immunological relatives thereof and then optionally isolating same.

Lol p Ib.1 protein, Lol p Ib.2 protein and fragments (peptides) thereof can be purified from cell culture medium, host cells, or both using techniques known in the art for purifying peptides and proteins, including ion-exchange chromatography, gel filtration chromatography, ultrafiltration, electrophoresis and immunopurification with antibodies specific for Lol p Ib.1, Lol p Ib.2 or fragment of Lol p Ib.1 or Lol p Ib.2. The terms isolated and purified are used interchangeably herein and refer to peptides, protein, protein fragments, and nucleic acid sequences substantially free of cellular material or culture medium when produced by recombinant DNA techniques, or chemical precursors or other chemicals when synthesized chemically.

Another aspect of the invention provides protein preparations comprising Lol p Ib, Lol p Ib.1, Lol p Ib.2 or at least one fragment of Lol p Ib, Lol p Ib.1 or Lol p Ib.2. In preferred embodiments of this aspect of the invention, Lol p Ib.1 or Lol p Ib.2 protein or at least one fragment of Lol p Ib.1 or Lol p Ib.2 is produced in a host cell transformed with a nucleic acid sequence coding for the protein or fragment.

Using the structural information now available, it is possible to design peptides derived from Lol p Ib which, when administered to a ryegrass pollen sensitive individual in sufficient quantities, will modify the individual's allergic response to ryegrass pollen. This can be done, for example, by examining the structure of Lol p Ib, producing peptides (via an expression system, synthetically or otherwise) to be examined for their ability to influence B-cell and/or T-cell responses in ryegrass pollen sensitive individuals and selecting appropriate epitopes recognized by the cells. In referring to an epitope, the epitope will be the basic element or smallest unit of recognition by a receptor, particularly immunoglobulins, histocompatibility antigens and T cell receptors where the amino acids essential to the receptor recognition may be contiguous and/or non-contiguous in the amino acid sequence. Amino acid sequences which mimic those of the epitopes and which are capable of down regulating allergic response to ryegrass pollen allergen can also be used.

It is now also possible to design an agent or a drug capable of blocking or inhibiting the ability of ryegrass pollen allergen to induce an allergic reaction in ryegrass pollen sensitive individuals. Such agents could be designed, for example, in such a manner that they would bind to relevant anti-Lol p Ib-IgE's, thus preventing IgE-allergen binding and subsequent mast cell or basophil degranulation. Alternatively, such agents could bind to cellular components of the immune system, resulting in suppression or desensitization of the allergic response to L. perenne pollen allergens. A non-restrictive example of this is the use of appropriate B- and T-cell epitope peptides, or modifications thereof, based on the cDNA/protein structures of the present invention to suppress the allergic response to ryegrass pollen. This can be carried out by defining the structures of B- and T-cell epitope peptides which affect B- and T-cell function in in vitro studies with blood components from ryegrass pollen sensitive individuals.

Protein, peptides or antibodies of the present invention can also be used for detecting and diagnosing ryegrass pollinosis. For example, this could be done by combining blood or blood products obtained from an individual to be assessed for sensitivity to ryegrass pollen with an isolated antigenic peptide or peptides of recombinantly or synthetically produced Lol p Ib or native purified Lol p Ib, or isolated Lol p Ib protein or isolated native purified Lol p Ib protein, under conditions appropriate for binding of components (e.g., antibodies, T-Cells, B-cells) in the blood with the peptide(s) or protein and determining the extent to which such binding occurs. The extent to which binding occurs can be determined, for example, by assessing T cell function, T cell proliferation, B cell function, or binding of the protein, or fragment thereof, or derivative or homologue thereof to antibodies present in the blood or a combination thereof.

Additionally, sensitivity of a mammal to ryegrass pollen may be determined by administering to a mammal a sufficient quantity of at least one ryegrass pollen allergen belonging to the Lol p Ib family, or at least one antigenic fragment thereof, or derivative or homologue thereof to provoke an allergic response in the mammal and determining the occurrence of an allergic response in the mammal to the ryegrass pollen allergen. The ryegrass pollen allergen(s), fragment(s) or derivative or homologue thereof used in this aspect of the present invention can be produced recombinantly or synthetically. Purified native Lol p Ib protein or fragments thereof may be substituted for a recombinantly or synthetically produced Lol p Ib or fragments thereof and used in the above method to determine sensitivity of the mammal to ryegrass.

The DNA used in any embodiment of this invention can be cDNA obtained as described herein, or alternatively, can be any oligodeoxynucleotide sequence having all or a portion of a sequence represented herein, or their functional equivalents. Such oligodeoxynucleotide sequences can be produced chemically or mechanically, using known techniques. A functional equivalent of an oligonucleotide sequence is one which is 1) a sequence capable of hybridizing to a complementary oligonucleotide to which the sequence (or corresponding sequence portions) of FIGS. 3b and 3c (Lol p Ib.1) or fragments thereof hybridizes or to which the sequence (or corresponding sequence portions) of FIGS. 10a and 10b (Lol p Ib.2) or fragments thereof hybridizes, or 2) the sequence (or corresponding sequence portion) complementary to the nucleic acid sequence of FIGS. 3b and 3c or FIGS. 10a and 10b, and/or 3) a sequence which encodes a product (e.g., a polypeptide or peptide) having the same functional characteristics of the product encoded by the sequence (or corresponding sequence portion) of the nucleic acid sequence of FIGS. 3b and 3c or FIGS. 10a and 10b. Whether a functional equivalent must meet one or more criteria will depend on its use (e.g., if it is to be used only as an oligoprobe, it need meet only the first or second criteria and if it is to be used to produce Lol p Ib, it need only meet the third criterion).

A Lol p Ib cDNA, including Lol p Ib.1 or Lol p Ib.2 (or the mRNA from which it was transcribed) or a portion thereof can be used to identify similar sequences in any variety or type of plant and thus, to identify or "pull out" sequences which have sufficient homology to hybridize to Lol p Ib cDNA or mRNA or portion thereof, for example, DNA from allergens of plants of the family Poaceae, under conditions of low stringency. Those sequences which have sufficient homology (generally greater than 40%) can be selected for further assessment using the method described herein. Alternatively, high stringency conditions can be used. In this manner, DNA of the present invention can be used to identify, in other types of plants, preferably related families, genera, or species, sequences encoding polypeptides having amino acid sequences similar to that of Lol p Ib and thus to identify allergens in other species. Thus, the present invention includes not only Lol p Ib, but also other allergens encoded by DNA which hybridizes to DNA of the present invention.

The invention further includes isolated allergenic proteins or fragments thereof that are immunologically related to Lol p Ib, including Lol p Ib.1 or Lol p Ib.2 or fragments, or derivatives or homologues thereof, such as by antibody cross-reactivity wherein the isolated allergenic proteins or fragments thereof are capable of binding to antibodies specific for the protein and peptides of the invention, or by T cell cross-reactivity wherein the isolated allergenic proteins or fragments thereof are capable of stimulating T cells specific for the protein and peptides of this invention.

Work by others has shown that high doses of allergens generally produce the best results (i.e., best symptom relief). However, many people are unable to tolerate large doses of allergens because of allergic reactions to the allergens. Modification of naturally-occurring allergens can be designed in such a manner that modified peptides or modified allergens which have the same or enhanced therapeutic properties as the corresponding naturally-occurring allergen but have reduced side effects (especially anaphylactic reactions) can be produced. These can be, for example, a protein or peptide of the present invention (e.g., one having all or a portion of the amino acid sequence of Lol p Ib, including Lol p Ib.1 or Lol p Ib.2 or purified native Lol p Ib), or a modified protein or peptide, or protein or peptide analogue. It is possible to modify the structure of a protein or peptide of the invention for such purposes as increasing solubility, enhancing therapeutic or preventive efficacy or stability (e.g., shelf life ex vivo and resistance to proteolytic degradation in vivo. A modified protein or peptide can be produced in which the amino acid sequence has been altered, such as by amino acid substitution, deletion or addition, to modify immunogenicity and/or reduce allergenicity or to which a component has been added for the same purpose.

Thus, the present invention provides modified ryegrass pollen protein allergens which, when administered to a ryegrass pollen-sensitive individual, reduce the allergic response of the individual to ryegrass pollen. Preferred modified ryegrass pollen protein allergens include modified Lol p Ib.1 protein or derivative or homologue thereof and modified Lol p Ib.2 protein or derivative or homologue thereof. The present invention also provides at least one modified fragment of ryegrass pollen protein allergen which, when administered to a ryegrass pollen-sensitive individual, reduces the allergic response of the individual to ryegrass pollen. Preferably such modified fragments are at least one modified fragment of Lol p Ib.1 protein or derivative or homologue thereof, or Lol p Ib.2 protein or derivative or homologue thereof.

Lol p Ib.1 or Lol p Ib.2 or purified native Lol p Ib protein or peptides can be modified, for example, using the polyethylene glycol method of A. Sehon and co-workers. Wie et al. (1981) Int. Arch. Allergy Appl. Immunology. 64: 84–99. Modification of Lol p Ib.1 or Lol p Ib.2 or purified native Lol p Ib protein or peptides can also include reduction/alkylation (Tarr [1986] in: Methods of Protein Microcharacterization, J. E. Silver, ed. Humana Press, Clifton, N.J., pp 155–194); acylation (Tarr, supra); esterification (Tarr, supra); chemical coupling to an appropriate carrier (Mishell and Shiigi, eds, [1980] Selected Methods in Cellular Immunology, W. H. Freeman, San Francisco, Calif.; U.S. Pat. No. 4,939,239); or mild formalin treatment (Marsh [1971] Int. Arch. Allergy Appl. Immunol. 41: 199–215).

Another example of a modification of protein or peptides is substitution of cysteine residues preferably with alanine, serine, threonine, leucine or glutamic acid to minimize dimerization via disulfide linkages. Another example of modification of the peptides of the invention is by chemical modification of amino acid side chains or cyclization of the peptide.

In order to enhance stability and/or reactivity, the protein or peptides of the invention can also be modified to incorporate one or more polymorphisms in the amino acid sequence of the protein allergen resulting from natural allelic variation. Additionally, D-amino acids, non-natural amino acids or non-amino acid analogues can be substituted or added to produce a modified protein or peptide within the scope of this invention.

Native Lol p Ib may be purified using conventional methods known in the art such as those in Scopes, R.K. (1987), Protein Purification, Principles and Practice, Second Edition, Springer-Verlag, New York, N.Y. Suitable methods include ion exchange chromatography, high pressure liquid chromatography, electrophoresis, ultrafiltration, iso-electric-focusing and immunoadsorption chromatography using antibodies specific for native Lol p Ib. Purification of native Lol p Ib by iso-electric-focusing and SDS-PAGE is described in Example 2.

The cloning of the cDNAs encoding Lol p Ib.1 and Lol p Ib.2 was based on the recognition of the protein expressed by *Escherichia. coli* transformed with lambda-gt 11 phage, using both specific monoclonal antibodies and specific serum IgE from grass pollen-sensitive patients. Two such clones are designated 12R and 19R. Also, monoclonal antibodies used were MAbs 3.2, FMC A7 (12.3), 21.3 and FMC A1 (40.1) (Kahn & Marsh (1986) *Molec. Immunol.* 23: 1281–1288; Singh & Knox (1985) *International Archives of Allergy and Applied Immunology* 78, 300–304; Smart et al. (1983) *International Archives of Allergy and Applied Immunology* 72 243–248). Details of the cloning of Lol p,Ib.1 and Lol p Ib.2 are given in the Examples.

The allergenic nature of the subject proteins are characterized in part, by their binding of the reaginic IgE antibodies which are present at high levels in sera of allergic patients. The IgE binding to the epitopes on allergic proteins can be tested in a chromogenic assay in which allergens immobilized on a solid support can be visualized by sequential incubation in (1) allergic patients serum; (2) enzyme-labelled anti-IgE antibodies.

Another aspect of the present invention relates to recombinant vectors comprising DNA sequences encoding proteins displaying allergenic activity from pollen of a grass species. More particularly, the grass species belongs to the family Poaceae (Gramineae), and even more particularly, to the genus Lolium. Still even more particularly, the allergenic protein is characterized as being immunologically cross-reactive with antibody to Lol p Ib protein of *Lolium perenne* pollen, namely:

Pooid (festucoid) grasses. GROUP 1: Triticanea: *Bromus inermis*, smooth broom; *Agropyron repens*, English couch; *A. cristatum*; *Secale cereale* rye *Triticum aestivum*, wheat. GROUP 2: Poanae: *Dactylis glomerata*, orchard grass of cocksfoot; *Festuca elatior*, meadow fescue; *Lolium perenne*, perennial ryegrass; *L. multiflorum*, Italian ryegrass; *Poa pratensis*, Kentucky bluegrass; *P. compressa*, flattened meadow grass; *Avena sativa*, oat; *Holcus lanatus*, velvet grass or Yorkshire fog; *Anthoxanthum odoratum*; sweet vernal grass; *Arrhenatherum elatius*, oat grass; *Agrostis alba*, red top; *Phleum pratense*, timothy; *Phalaris arundinacea*, reed canary grass. Panicold grass, *Paspalum notatum*, Bahia grass, Andropogonoid grasses: *Sorghum halepensis*, Johnson grass.

A variety of expression vectors can be constructed for the production of Lol p Ib, at least one fragment thereof or their derivatives. Thus, a further aspect of the present invention provides recombinant vectors comprising DNA sequences encoding the allergenic protein Lol p Ib of ryegrass, *Lolium perenne*, L. pollen, or derivatives or homologues thereof. More particularly, the present invention relates to recombinant DNA molecules comprising a eukaryotic or prokaryotic origin of replication, a detectable marker, DNA sequences encoding Lol p Ib family members or derivatives or homologues thereof, or allergenic proteins cross-reactive with antibodies to Lol p Ib family members or derivatives or homologues thereof, and, optionally, promoter sequences capable of directing transcription of Lol p Ib family members.

The present invention also extends to the promoter of ryegrass pollen proteins, and particularly, to a promoter of a Lol p Ib gene such as the gene encoding Lol p Ib.1 and Lol p Ib.2. This promoter developmentally regulates a Lol p Ib gene expression and is organ, i.e., pollen specific. Developmental regulation as used herein refers to the expression of a particular trait, in this case allergenic proteins in pollen, during a certain stage in a plants life cycle and non-expression during another stage. Hence, the Lol p Ib promoter is particularly useful in allowing expression of Lol p Ib, or any other gene or nucleotide sequence relative thereto, only during the development of pollen. The skilled artisan will immediately recognize the importance of such promoters in selectively expressing a particular trait during pollen formation.

Accordingly, the present invention provides a method of inhibiting pollen development or function and thereby inducing nuclear male sterility in plants of the family Poaceae, and in particular *Lolium perenne* L., comprising the steps of:

a) developing a plant carrying a recombinant DNA molecule comprising a ryegrass pollen promoter sequence or homologue or degenerate form thereof located on said molecule and a nucleotide sequence encoding a polypeptide having a deleterious function in cells derived from the family Poaceae, said nucleotide sequence transcribeable from said promoter, and said recombinant DNA molecule stably contained in pollen producing cells, and, b) growing said plants under conditions and for a time sufficient for their development stage to cause expression of said nucleotide sequence from said promoter thereby producing the polypeptide having a deleterious function in said pollen producing cells such that pollen formation is inhibited or said pollen is inactive.

Well established methods exist for introducing recombinant DNA molecules into plant cells such as use of Agrobacterium plasmids and electroporation amongst others. By "deleterious function" in respect of a polypeptide refers to a feature of said polypeptide that will inhibit cell growth, cause lysis of a cell, or inhibit various functions in a cell and thereby prevent the normal functioning of the cell. In this case, lethal gene constructs having a deleterious function are contemplated which inhibit or prevent pollen formation and thereby result in a male sterile plant. Such "lethal genes" may encode enzymes, enzyme inhibitors, and/or toxic polypeptides, amongst other molecules. Alternatively, the lethal gene may encode an antisense RNA capable of inhibiting translation of a particular species of mRNA, the translated product thereof, being vital for pollen development.

Male sterile plants are particularly useful in developing hybrid crop varieties.

The Lol p Ib promoter is isolatable from ryegrass genomic DNA by any number of procedures including use of promoter probes vectors, "chromosome walking" and S1 nuclease mapping and sequencing as DNA upstream of the transcription initiation site.

Accordingly, the present invention provides a recombinant DNA molecule comprising a ryegrass pollen promoter sequence, and in particular a promoter for a gene encoding a Lol p Ib family member, or homologues or degenerate forms thereof located on said molecule and further having one or more restriction endonuclease sites downstream of said promoter such that a nucleotide sequence inserted into one or more of these sites is transcribable in the correct reading frame and is thereby a developmentally regulated, pollen-specific expression vector. As used herein, the "correct reading frame" has the same meaning as "in phase". The aforementioned DNA molecule will preferably also have a selectable marker thereon, such as an antibiotic or other drug resistance gene, such as for example gene encoding resistance to ampicillin, carbenicillin, tetracycline, streptomycin and the like. The recombinant molecule will further comprise a means for stable inheritance in a prokaryotic and/or eukaryotic cell. This can be accomplished by said recombinant molecule carrying a eukaryotic and/or a prokaryotic origin of replication as hereinbefore described in relation to expression vectors.

Alternatively, the recombinant molecule will carry a means for integration into a host cell genome thereby permitting replication of said recombinant molecule in synchrony with the replication of said host cell genome. Examples of preferred prokaryotic hosts include cells *E. coli*, Bacillus and Pseudomonas amongst others. Preferred eukaryotic hosts include cells from yeast and fungi, insects, mammals and plants. Even more preferred host cells are plants of the family Poaceae, and in particular of the genus Lolium, such as *Lolium perenne*. Accordingly in a preferred embodiment, a Lol p Ib gene promoter with a gene encoding a deleterious function positioned relative thereto will be carried by a recombinant DNA molecule capable of integration into the genome of cells of plants from the family Poaceae, or *L. perenne*. Such a recombinant DNA molecule is transferred to the aforementioned cells by, for example, electroporation. Ideally, said cells are callus-derived cells. Said callus-derived cells transformed with said recombinant DNA molecule are then permitted to regenerate into whole plants. Whole plants entering the pollen development stage of its like cycle permit functioning of a Lol p Ib gene promoter and, hence, expression of the gene encoding a deleterious function. Consequently, pollen development is inhibited or prevented and a nuclear male sterile plant results therefrom.

Alternatively, a Lol p Ib promoter will direct expression of a gene having advantageous functions, such as a cytokinin. All such recombinant DNA molecules are encompassed by the present invention.

The present invention extends to monoclonal and polyclonal antibodies to Lol p Ib or at least one fragment of recombinantly or synthetically produced Lol p Ib or purified native Lol p Ib, produced according to the methods described in International Patent Application No. PCT/AU89/00123 and to their use in immunoassays and test kits as described therein.

The monoclonal antibodies used in the present work to screen the cDNA library for Lol p Ib clones showed cross-reactivity with allergenic proteins from pollen of various related grass species. This shows there is a homology between allergenic proteins produced by these pollens with Lol p Ib protein allergens supporting the applicability of the present invention to all related grasses. The present invention also relates to antibodies to recombinant Lol p Ib protein allergens and derivatives, homologues and immunological relatives thereof including chemical synthetic derivatives thereof. In the following discussion, reference to Lol p Ib protein allergens includes its derivatives, homologues and immunological relatives and chemical synthetic derivatives thereof. The following discussion also includes antibodies specific for purified Lol p Ib and fragments, derivative and homologues thereof. Such antibodies are contemplated to be useful in developing detection assays (immunoassays) for Lol p Ib protein allergens especially during the monitoring of a therapeutic or diagnostic regimen and in the purification of recombinantly or synthetically produced Lol p Ib family members or purified native Lol p Ib. The antibodies may be monoclonal or polyclonal. Additionally, it is within the scope of this invention to include any second antibodies (monoclonal or polyclonal) directed to the first antibodies discussed above. The present invention further contemplates use of these first or second antibodies in detection assays and, for example, in monitoring the effect of a diagnostic or an administered pharmaceutical preparation. Furthermore, it is within the scope of the present invention to include antibodies to any molecules complexed with a Lol p Ib protein allergen. Accordingly, an antibody to a Lol p Ib protein allergen encompasses antibodies to such Lol p Ib protein allergen, or antigenic parts thereof, and to any associated molecules (e.g., lipid regions, carrier molecules, fused proteins, and the like).

The Lol p Ib family members, or fragments thereof, considered herein are purified then utilized in antibody production. Both polyclonal and monoclonal antibodies are obtainable by immunization with recombinant, synthetic or native Lol p Ib protein family members, and either type is utilizable for immunoassays. The methods of obtaining both types of sera are well known in the art. Polyclonal sera are less preferred but are relatively easily prepared by injection of a suitable laboratory animal with an effective amount of a purified Lol p Ib family member, or antigenic parts thereof, collecting serum from the animal, and isolating specific sera by any of the known immunoabsorbent techniques. Although antibodies produced by this method are utilizable in virtually any type of immunoassay, they are generally less favored because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. (See, for example, Kohler and Milstein (1975) *Nature* 256: 495–499, and Kohler and Milstein (1986) *Eur. J. Immunol.* 6: 511–519.

Unlike preparation of polyclonal sera, the choice of animal is dependent on the availability of appropriate immortal lines capable of fusing with lymphocytes. Mouse and rat have been the animals of choice in hybridoma technology and are preferably used. Humans can also be utilized as sources for sensitized lymphocytes if appropriate immortalized human (or nonhuman) cell lines are available. For the purpose of the present invention, the animal of choice may be injected with from about 0.1 mg to about 20 mg of purified recombinant or native Lol p Ib, or parts thereof. Usually the injecting material is emulsified in Freund's complete adjuvant. Boosting injections may also be required. The detection of antibody production can be carried out by testing the antisera with appropriately labelled antigen. Lymphocytes can be obtained by removing the spleen or lymph nodes of sensitized animals in a sterile fashion and carrying out fusion. Alternatively, lymphocytes can be stimulated or immunized in vitro, as described, for example, in Reading (1982) *J. Immunol. Methods* 53:261–291.

A number of cell lines suitable for fusion have been developed, and the choice of any particular line for hybridization protocols is directed by any one of a number of criteria such as speed, uniformity of growth characteristics, deficiency of its metabolism for a component of the growth medium, and potential for good fusion frequency.

Intraspecies hybrids, particularly between like strains, work better than interspecies fusions. Several cell lines are available, including mutants selected for the loss of ability to secrete myeloma immunoglobulin.

Cell fusion can be induced either by virus, such as Epstein-Barr or Sendai virus, or polyethylene glycol. Polyethylene glycol (PEG) is the most efficacious agent for the fusion of mammalian somatic cells. PEG itself may be toxic for cells, and various concentrations should be tested for effects on viability before attempting fusion. The molecular weight range of PEG may be varied from 1000 to 6000. It gives best results when diluted to from about 20% to about 70% (w/w) in saline or serum-free medium. Exposure to PEG at 37° C. for about 30 seconds is preferred in the present case, utilizing murine cells. Extremes of temperature (i.e., about 45° C.) are avoided, and preincubation of each component of the fusion system at 37° C. prior to fusion can be useful. The ratio between lymphocytes and malignant cells is optimized to avoid cell fusion among spleen cells and a range of from about 1:1 to about 1:10 is commonly used.

The successfully fused cells can be separated from the myeloma line by any technique known by the art. The most common and preferred method is to chose a malignant line which is hypoxanthine guanine phosphoribosyl transferase (HGPRT) deficient, which will not grow in an aminopterin-containing medium used to allow only growth of hybrids, and aminopterin-containing medium used to allow only growth of hybrids and which is generally composed of hypoxanthine $1.10^{-4}$M, aminopterin $1\times10^{-5}$M, and thymidine $3\times10^{-5}$M, commonly known as the HAT medium. The fusion mixture can be grown in the HAT-containing culture medium immediately after the fusion or 24 hours later. The feeding schedules usually entail maintenance in HAT medium for two weeks and then feeding with either regular culture medium or hypoxanthine, thymidine-containing medium.

The growing colonies are then tested for the presence of antibodies that recognize the antigenic preparation. Detection of hybridoma antibodies can be performed using an assay where the antigen is bound to a solid support and allowed to react to hybridoma supernatants containing putative antibodies. The presence of antibodies may be detected by "sandwich" techniques using a variety of indicators. Most of the common methods are sufficiently sensitive for use in the range of antibody concentrations secreted during hybrid growth.

Cloning of hybrids can be carried out after 21–23 days of cell growth in selected medium. Cloning can be preformed by cell limiting dilution in fluid phase or by directly selecting single cells growing in semi-solid agarose. For limiting dilution, cell suspensions are diluted serially to yield a statistical probability of having only one cell per well. For the agarose technique, hybrids are seeded in a semisolid upper layer, over a lower layer containing feeder cells. The colonies from the upper layer may be picked up and eventually transferred to wells.

Antibody-secreting hybrids can be grown in various tissue culture flasks, yielding supernatants with variable concentrations of antibodies. In order to obtain higher concentrations, hybrids may be transferred into animals to obtain inflammatory ascites. Antibody-containing ascites can be harvested 8–12 days after intraperitoneal injection. The ascites contain a higher concentration of antibodies but include both monoclonals and immunoglobulins from the inflammatory ascites. Antibody purification may then be achieved by, for example, affinity chromatography.

The presence of Lol p Ib protein allergen contemplated herein, or antibodies specific for same, in a patient's serum, plant or mammalian tissue or tissue extract, can be detected utilizing antibodies prepared as above, either monoclonal or polyclonal, in virtually any type of immunoassay. A wide range of immunoassay techniques are available as can be seen by reference to U.S. Pat. Nos. 4,015,043, 4,424,279 and 4,018,653. This, of course, includes both single-site and two-site, or "sandwich", assays of the non-competitive types, as well as in the traditional competitive binding assays. Sandwich assays are among the most useful and commonly used assays and are favored for use in the present invention. A number of variations of the sandwich assay technique exist, and all are intended to be encompassed by the present invention. Briefly, in a typical forward assay, an unlabeled antibody is immobilized in a solid substrate and the sample to be tested brought into contact with the bound molecule. After a suitable period of incubation, for a period of time sufficient to allow formation of an antibody-antigen secondary complex, a second antibody, labelled with a reporter molecule capable of producing a detectable signal is then added and incubated, allowing time sufficient for the formation of a tertiary complex of antibody-antigen-labelled antibody (e.g., antibody-Lol p Ib protein-antibody). Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labelled antibody are added simultaneously to the bound antibody, or a reverse assay in which the labelled antibody and sample to be tested are first combined, incubated and then added simultaneously to the bound antibody. These techniques are well known to those skilled in the art, including any minor variations as will be readily apparent.

Although the following discussion is concerned with detecting Lol p Ib, it is equally applicable to detecting antibodies to Lol p Ib and it is intended to be a sufficient description thereof. In the typical forward sandwich assay, a first antibody having specificity for Lol p Ib, or antigenic parts thereof, contemplated in this invention, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated at 25° C. for a period of time sufficient to allow binding of any subunit present in the antibody. The incubation period will vary but will generally be in the range of about 2–40 minutes. Following the incubation period, the antibody subunit solid phase is washed and dried and incubated with a second antibody specific for a portion of the hapten. The second antibody is linked to a reporter molecule which is used to indicate the binding of the second antibody to the hapten.

By "reporter molecule," as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e., radioisotopes). In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidass, beta-galactosidase and alkaline phosphatase, amongst others. The substrates to be used with the specific enzymes are generally chose for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine, 5-aminosalicylic acid, or toluidine are commonly used. It is also possible to employ fluorogenic substrates, which yield a fluorescent product rather than the chromogenic substrates noted above. In all cases, the enzyme-labelled antibody is added to the first antibody hapten complex, allowed to bind, and then the excess reagent is washed away. A solution containing the appropriate substrate is then added to the tertiary complex of antibody-antigen-antibody. The substrate will react with the enzyme linked to the second antibody, giving a qualitative visual signal, which may be further quantitated, usually spectrophotometrically, to give an indication of the amount of hapten which was present in the sample. "Reporter molecule" also extends to use of cell agglutination or inhibition of agglutination such as red blood cells or latex beads, and the like.

Alternately, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic color visually detectable with a light microscope. As in the EIA, the fluorescent labelled antibody is allowed to bind to the first antibody-hapten complex. After washing off the unbound reagent, the remaining tertiary complex is then exposed to the light of the appropriate wavelength, the fluorescein observed indicates the presence of the hapten of interest. Immunofluorescence and EIA techniques are both very well established in the art and are particularly preferred for the present method. However, other reporter molecules, such as radioisotope, chemilluminescent or bioluminescent molecules, may also be employed. It will be readily apparent to the skilled technician how to vary the procedure to suit the required purpose. It will also be apparent that the foregoing can be used to detect directly or indirectly (i.e., via antibodies) Lol p Ib protein of this invention.

Accordingly, one aspect of the present invention provides a method of detecting Lol p Ib or a derivative or homologue thereof or an allergenic protein immunologically reactive with said Lol p Ib or derivatives or homologues present in serum, tissue extract, plant extract or other biological fluid comprising the steps of containing said serum, extract or fluid to be tested with an antibody to said Lol p Ib protein for a time and under conditions sufficient for an allergenic protein-antibody complex to form and subjecting said complex to a detecting means. The present invention also provides a method of detecting an antibody to an allergenic protein from pollen of the family Poaceae (Gramineae) in serum or other biological fluid comprising contacting said serum or fluid with a Lol p Ib protein, or derivative or homologue thereof, or its antigenic derivative for a time and under conditions sufficient for an antibody-Lol p Ib complex to form and subjecting said complex to a detecting means. The latter complex may be detected by the Lol p Ib protein having attached thereto a reporter molecule or by addition of a second antibody labelled with a reporter molecule.

Accordingly, the present invention is also directed to a kit for the rapid and convenient assay for antibodies to Lol p Ib or derivatives, homologues or immunological relatives thereof in mammalian body fluids (e.g., serum, tissue extracts, tissue fluids), in vitro cell culture supernatants, and cell lysates. The kit is compartmentalized to receive a first container adapted to an antigenic component thereof, and a second container adapted to contain an antibody to Lol p Ib, said antibody being labelled with a reporter molecule capable of giving a detectable signal as hereinbefore described. If the reporter molecule is an enzyme, then a third container adapted to contain a substrate for said enzyme is provided. In an exemplified use of the subject kit, a sample to be tested is contacted with the contents of the first container for a time and under conditions for an antibody, if present in the sample, to bind to Lol p Ib protein in said first container. If the Lol p Ib protein of the first container has bound to antibodies in the test fluid, the antibodies of the second container will bind to the secondary complex to form a tertiary complex and, since these antibodies are labelled with a reporter molecule, when subjected to a detecting means, the tertiary complex is detected. Therefore, one aspect of the present invention is a kit for the detection of antibodies to a protein having allergenic properties, said protein from pollen of the family Poaceae (Gramineae), the kit being compartmentalized to receive a first container adapted to contain recombinant Lol p Ib protein or its antigenic derivative or homologue or a purified native Lol p Ib protein or its antigenic derivative or homologue, and a second container adapted to contain an antibody to Lol p Ib or derivative or homologue thereof, said antibody labelled with a reporter molecule capable of giving a detectable signal. The "reporter molecule" may also involve agglutination of red blood cells (RBC) on latex beads. In this kit the reporter molecule is a radioisotope, an enzyme, an fluorescent molecule, a chemilluminescent molecule, bioluminescent molecule or RBC. The kit alternatively comprises a container adapted to contain recombinant Lol p Ib or is antigenic derivative or homologue labelled with a reporter molecule capable of giving a detectable signal.

Because of the presence of allergens in the environment, hayfever and seasonal asthma continue to have significant morbidity and socio-economic impact on Western communities, despite advances made in their pharmacology and immunology. While the available spectrum of drugs, including anti-histamines and steroids have resulted in improvement in the treatment of allergic disease, they have unfortunate side-effects associated with long-term usage. Because of these problems, renewed interest has been shown in the immunotherapy of allergic disease. Immunotherapy involves the injection of potent allergen extracts to desensitize patents against allergic reactions (Bousquet, & Michel (1989) *Allergy Clin. Immunol. News* 1: 7–10). Unfortunately, the pollen preparations used as allergens are polyvalent and of poor quality. Consequently, concentrations used are frequently high in order to induce IgG responses, but may be lethal through triggering of systemic reactions, including anaphylaxis. The cloned gens product or synthetic peptides based on the sequence of allergens provides a safer medium for therapy since it can be quality controlled, characterized and standardized.

The precise mechanism for symptomatic relief remains hypothetical. However, administration of a preparation comprising recombinant, synthetic or purified native Lol p Ib or at least one antigenic fragment thereof, of the instant invention to a ryegrass sensitive individual will modify the allergic response of a ryegrass sensitive individual to ryegrass pollen allergens, e.g. by modifying the B-cell response to Lol p Ib, the T-cell response to Lol p Ib, or both the B cell and T cell response to Lol p Ib.

Currently immunotherapy is one of the most frequently administered treatments in allergology, and in the U.S.A. it is considered the first choice. An advantage of this treatment for pollen rhinitis is that treatment takes up to 3 years, while pharmacotherapy must be carried out during the patent's entire life time. Patients given pollen extract for immunotherapy showed a clinical benefit that lasted for four years after the end of treatment (Grammer et al. (1984) *J. Allergy Clin. Immunol* 73: 484–489).

Immune responsiveness to rye-grass pollen allergens Lol p II and Lol p III in the human population is significantly associated with the histocompatibility leukocyte antigen HLA-DR3 (Friedhoff et al. (1988) *Tissue Antigens* 31: 211–219; Ansari, et al. (1989) *Human Immunol.* 25: 59–71; Ansari et al. (1989) *Int. Arch. Allergy Appl. Immunol.* 88: 164–189). This means that the HLA-DR3 encoded class II Ia molecules of the antigen-presenting cells may recognize a similar immunodominant T cell/Ia recognition site present on another allergen. Lol p Ia is known to share an immunodominant T cell/Ia recognition site (YTTEGGTKS EVEDV IP) with both Lol p II and Lol pIII (Friedhoff et al., supra). Most allergic individuals who respond to Lol p II and III also respond to Lol pIa, but not the reciprocal. Thus, Lol p Ia appears to have unique T cell/Ia recognition site(s) not present in Lol p II or III. Furthermore, the common T cell/Ia recognition site shared between Lol p Ia, II and III is not represented in the deduced sequence of Lol p Ib.1 or Lol p Ib.2.

Accordingly, the present invention is directed to the Lol p Ib family of protein allergens, their derivatives, homologues or immunological relatives including derivatives containing the common antigenic epitope between Lol p Ia and Lol p Ib.1 which are useful in developing a vaccine to desensitize humans to allergies due to grass pollen.

Accordingly, the present invention provides a method for desensitizing a human allergic to grass pollen which comprises administering to said human a desensitizing-effective amount of Lol p Ib or at least one fragment or a derivative, homologue, or immunological relative thereof, for a time and under conditions sufficient to effect desensitization of the human to the grass pollen.

The present invention also provides a method of treating sensitivity to ryegrass pollen in a mammal sensitive to such pollen, comprising administering to the mammal a therapeutically effective amount of a therapeutic composition of the invention. The present invention further provides a method of treating sensitivity to ryegrass pollen allergen or an allergen immunologically cross-reactive with ryegrass pollen allergen comprising administering to a mammal a therapeutically effective amount of said protein preparation of the invention.

Through the use of the peptides and protein of the present invention, preparations of consistent, well-defined composition and biological activity can be made and administered for therapeutic purposes (e.g., to modify the allergic response of a L perenne sensitive individual to pollen of such plants. Administration of such peptides or protein may, may, for example, modify B-cell response to Lol p Ib allergen, T-cell response to Lol p Ib allergen, or both responses. Purified peptides can also be used to study the mechanism of immunotherapy of *L. perenne* allergy and to design modified derivatives or analogues useful in immunotherapy.

The present invention, therefore, provides a pharmaceutical compositions comprising a desensitizing or therapeutically effective amount of Lol p Ib or derivatives, homologues or immunological relatives thereof and one or more pharmaceutically acceptable carriers and/or diluents. The active ingredients of a pharmaceutical composition comprising Lol p Ib is contemplated to exhibit excellent therapeutic activity, for example, in the desensitization of humans allergic to grass pollen when administered in amount which depends on the particular case. For example, from about 0.5 ug to about 20 mg per kilogram of body weight per day may be administered. Dosage regime may be adjusted to provide the optimum therapeutic response. For example, several divided doses may be administered daily or the dose may be proportionally reduced as indicated by the exigencies of the therapeutic situation. The active compound may be administered in a convenient manner such as by the oral, intravenous (where water soluble), intramuscular, subcutaneous, intranasal, intradermal or suppository routes or implanting (e.g., using slow release molecules). Depending on the route of administration, the active ingredients which comprise the pharmaceutical composition of the invention may be required to be coated in a material to protect said ingredients from the action of enzymes, acids and other natural conditions which may inactivate said ingredients. For example, Lol p Ib may be administered in an adjuvant, co-administered with enzyme inhibitors or in liposomes. Adjuvant is used in its broadest sense and includes any immune stimulating compound, such as interferon. Adjuvants contemplated herein include resorcinols, non-ionic surfactants such as polyoxyethylene oleyl ether and n-hexadecyl polyethylene ether. Enzyme inhibitors include pancreatic trypsin. Liposomes include water-in-oil-in-water CGF emulsions as well as conventional liposomes. For purposes of inducing T cell anergy, the pharmaceutical composition if preferably administered in non-immunogenic form (e.g. it does not contain adjuvant).

The active compounds may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders of the extemporaneous dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

Figure 1A:
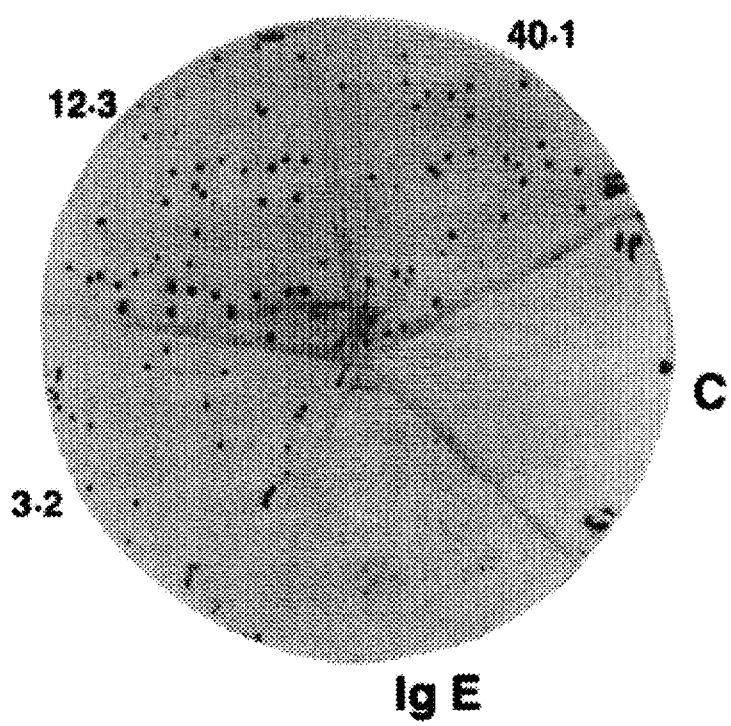
FIG. 1a illustrates recognition of a positive clone (12R) by three different MAbs FMC A1 (40.1), FMC A7 (12.3), 3.2 (Kahn & Marsh (1986) Molec. Immunol. 23: 1281–1288; Singh & Knox (1985) International Archives of Allergy and Applied Immunology 78, 300–304; Smart et al. (1983) International Archives of Allergy and Applied Immunology 72 243–248) and IgE from allergic patients' sera. C is the control in which the primary MAb was omitted.

When at least one Lol p Ib family member, or at least one fragment thereof is suitably protected as described above, the active compound may be orally administered, for example, with an inert diluent or with an assimilable edible carrier, or it may be enclosed in hard or soft shell gelatin capsule, or it may be compressed into tablets, or it may be incorporated directly with food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be carried and may conveniently be between about 5 to 80% of the weight of the unit. The amount of active compound in such therapeutically useful compositions is such that a suitable dosage will be obtained. Preferred compositions or preparations according to the present invention are prepared so that an oral dosage unit form contains between about 10 ug and 2000 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

As used herein "pharmaceutically acceptable carrier and/or diluent" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosagto pit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (1) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from about 10 μg to about 2000 mg. Expressed in proportions, the active compound is generally present in from about 10 μg to about 2000 mg/ml of carrier. In the case of compositions containing supplementary active ingredients, the dosages are determined by reference to the usual dose and manner of administration of the said ingredients.

The present invention is further illustrated by the following non-limiting Figures and Examples.

EXAMPLES

Example 1

Isolation of cDNA Clones

A cDNA expression library in the vector lambda-gt 11 was prepared from polyadenylated mRNA of mature ryegrass pollen (Beall & Mitchell (1986) *J. Immunol.* Methods 86: 217–223). This library was screened initially with monoclonal antibody (MAb) FMC-A1 (40.1) (FIG. 1*a*).

Poly (A+) mRNA isolated from mature rye grass pollen by the phenol method (Herrin and Michaels, (1984) *Plant Mol. Biol. Rep.*, 2:24–28) was used to construct a cDNA library in the vector lambda-gt 11. The library was then screened with antibody probes to detect sequences expressing Group I proteins. *E. coli* Y1090 transfected with $3\times10^4$ recombinant phages were plated and incubated at 42° C. for 3 h. The plates were overlaid with a dry 132 mm nitrocellulose (NC) filter previously soaked in 10 mm IPTG and transferred to 37° C. After incubation for 3 h the filters were carefully peeled off and incubated in 20 ml per filter of MTBS (10% w/v non-fat milk powder, 50 mm Tris-HCl, pH 7.6, 150 mM NaCl) for 30 min. at room temperature. A second set of NC filters was placed on phage plates and after incubating for 3 h were treated as above. Both sets of NC filters were tested for binding of MAb 40.1 to plaques by the method described in Huynh et al. (1985) In: DNA Cloning, a practical approach, Glover, D. M. (ed.) Vol. 1, pp. 49–78, IRL Press, Oxford, England. The antibody positive plaques were picked, purified, then replated and tested for binding to probes. The positive clones were plaque-purified and tested for IgE binding using sera from grass pollen-allergic subjects. Eighteen clones were selected as encoding proteins recognized by both Lol p I-specific MAbs and IgE antibodies (Table 1). The largest of the cDNA clones, 1.2 kb in size, that expressed rye-grass allergenic protein was initially selected for further characterization and sequencing, and designated clone lambda-12R (FIG. 1a).

TABLE 1

Characteristics of cDNA Clones Expressing Group I Allergens of Ryegrass

| Clone No. (-R) | Binding of MAb 12.3* | Binding of MAb 40.1* | Binding of IgE from sera of allergic indivs. | Approx. Size of Insert (bp) |
|---|---|---|---|---|
| 1 | – | – | – | |
| 2 | + | ++ | – | 700 |
| 3 | + | ++ | – | 600 |
| 4 | + | ++ | – | 800 |
| 5 | + | ++ | – | 500 |
| 6 | + | ++ | – | 600 |
| 7 | + | ++ | – | 400 |
| 8 | – | – | – | |
| 9 | – | – | – | |
| 10 | – | – | – | |
| 11 | + | ++ | – | 500 |
| 12 | ++ | ++ | ++ | 1200 |
| 13 | + | ++ | + | 800 |
| 14 | ++ | ++ | ++ | 1200 |
| 15 | – | – | – | |
| 16 | + | ++ | – | 800 |
| 17 | + | ++ | – | 400 |
| 18 | ++ | ++ | ++ | 1200 |

++: -strongest binding
–: -no binding
MAb 12.3 shows high affinity for Lol p Ib.1 encoded by clone 12R.

Figure 1B:
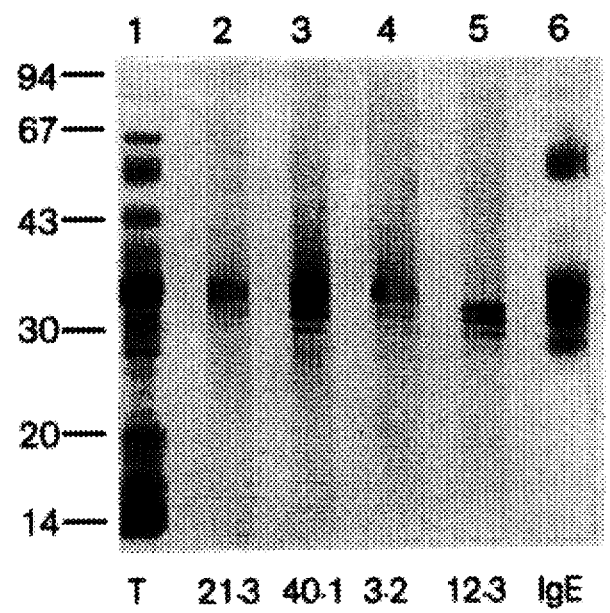
FIG. 1b shows an immunoblot analysis of MAbs and IgE binding to group I antigens from rye-grass pollen. Lane 1 shows total protein profile (Coomassie blue staining); Lane 2: MAb 21.3; Lane 3: MAb 40.1; Lane 4: MAb 3.2; Lane 5 12.3-; Lane 6: IgE antibodies.

The specificity of IgE and MAbs was tested by immunoblot analysis of rye-grass pollen protein extracts (FIG. 1b).

Soluble proteins were extracted from rye-grass pollen by vigorous shaking in PBS (150 mM NaCl in 10 mM sodium phosphate, pH 7.2) on ice for 3 h. Pollen was spun out of solution and the extracted protein standardized using the Biorad assay. 120 ug protein per lane was electrophoresed under reducing conditions on a 10–15% w/v SDS-polyacrylamide gel. Proteins were electroblotted onto NC filters and the blot blocked with TBS (10 mM Tris, 150 mM NaCl, pH 7.9) containing 10% w/v non-fat milk powder. The blot was cut into strips and each treated with the various probes: MAbs were diluted 1:1000 in TBS containing 1% BSA. Sera collected from at least 4 patients with high RAST scores for grass pollen, was pooled and used diluted 1:5 in TBS/1% w/v BSA for IgE binding. Horseradish peroxidase-conjugated secondary antibodies were used (Dakopatts, Glostrup, Denmark) and after washing, binding was visualized with 4-chloro 1-naphthol (Biorad, Richmond, Calif.) and $H_2O_2$.

When the immunoblot was incubated in pooled sera from grass pollen-allergic individuals, strong IgE binding was observed throughout the 28–35 kD region. The MAbs used in this study, 3.2, 12.3, 21.3 and 40.1 had previously been partially characterized (Kahn and Marsh (1986) Molec. Immunol. 23: 1281–1288; Singh and Knox (1985) Intl. Arch. Allergy and Applied. Immunol. 78: 300–304; Smart et al. (1983) Intl. Arch. Allergy and Applied Immunol. 72: 243–248). MAbs 3.2, 21.3 and 40.1 showed strong reactivity with the proteins in the 28–35 kD region. MAb 12.3 exhibited no binding to the 35 Kd band, but bound strongly to the lower bands. These interactions suggest that both IgE and MAbs can recognize denatured allergens, which makes them suitable probes for the detection of recombinant protein expressed in E. coli. It was previously thought that MAb FMC-A1 had a strong preference for Lol p Ia, although it would also bind to a lesser extent to Lol p Ib. New data suggests that the original FMC-A1 preparation may be polyclonal rather than monoclonal. One antibody in the FMC-A1 preparation appears to be specific for Lol p Ia while one appears to be specific for Lol p Ib. Therefore, the apparent cross-reaction of Lol p Ia and Lol p Ib defined by FMC-A1 may reflect polyclonality in this antibody preparation.

The allergen-beta-galactosidase fusion protein produced by the induction of lysogenic cultures of the lambda clone containing the 12R insert was characterized by immunoblot analysis using MAb 40.1. This fusion protein of approximately 146 kD is assumed to be comprised of the 116 kD beta-galactosidase and 30 kD of allergen-encoded sequence. This fusion protein was produced in low yields. So in order to increase yields of the cloned allergen for further analysis, we used an alternative expression system. The 1.2 kb insert was subcloned in the pGEX1–3 series of plasmid expression vectors. These plasmids give a fusion polypspride with the carboxyl terminus of the Schistosoma japonicum glutathione S-transferase protein (Smith and Johnson, (1988), Gene, 67:31–40). Strong IgE binding was detected only in bacteria transformed with pGEX-12R, and not in those with parental pGEX plasmids (data not shown, but similar binding shown in FIG. 4). Probing of Western blots with control sera that had negative radioallergosorbent (RAST) score for rye-grass pollen showed no IgE binding.

Example 2

Identity of Cloned Allergen 12R

All four MAbs used in this study recognized the cloned allergen 12R (FIG. 1a).

Not all MAbs show the same specificity to the native Lol p I proteins (FIG. 1b). In particular, MAb 12.3 does not recognize the 35 kD band. Because the cloned allergen binds all the MAbs, and with high intensity to MAb 12.3, it is predicted that the cloned allergen is likely to correspond to a protein of lower Mr, and not to the 35 kD protein. To confirm its identity, an immunological approach developed for parasite antigens was employed (e.g. Beall & Mitchell (1986) J. Immunol. Methods 86: 217–223). In this method, the cloned allergen 12R was immobilized on nitrocellulose membrane, and used to bind specific IgE antibodies from sera. Bound antibodies were eluted and used to probe a Western blot of rye-grass pollen proteins. Highly specific and reproducible patterns of binding were consistently obtained in several experiments to two protein components of molecular weight 31 and 33 kD. The 35 kD band has been designated Lol p Ia and the 31 and 33 kD bands have been designated Lol p Ib. These experiments demonstrate that IgE antibodies that bind to clone 12R recognize two components with slightly different molecular weights, 31 and 33 kD. No specific binding was observed when IgE antibodies from non-grass pollen allergic individuals were used nor when extracts of *E. coli* transformed with non-recombinant pGEX plasmids were used to select IgE antibodies.

Lol p Ib protein was purified by two-dimensional analysis involving preparative iso-electric focusing in the first dimension, followed by SDS-PAGE of the individual fractions collected. This procedure successfully separated Lol p Ib in sufficient quantity for the N-terminal sequence to be determined (Table 2).

TABLE 2

N-Terminal Amino Acid Sequences Of Grass Pollen Allergens Obtained In This Study Compared With Reported Sequences

| Allergen | N-terminal sequence |
|---|---|
| Lol pIa | IAKVPG??I TAEYGDKWLD AKSTWYGKPT |
| Lol pIb | ADAGYTPAA? ?TPATAP?T |
| Clone 12R | ADAGYTPAAA ATPATPAATP AAAGGKATTD EQKL |
| Lol pII | AAPVEFTVEK GSDEKNLALS IKYNKEGDSM A |
| Lol pIII | -TKVDLTVEK GSDAKTLVLN IKYTRPGDTL A |
| Phl p V | ADLGYAPATP AAPGAGYTPA TPAAP |
| Dac g V | GYTPATPAAA GGKATIEEQK L |
| Poa p IX | ADVGYGAPAT LATPATPAAP AAGYTPAAPA GAAP |

(The N-terminal amino acid sequences in Table 2 are represented as follows: Lol p Ia — SEQ ID NO:5; Lol p Ib — SEQ ID NO:6; Clone 12R — SEQ ID NO:7; Lol p II — SEQ ID NO:8; Lol p III — SEQ ID NO:9; Phl p V — SEQ ID NO:10; Dac g V, — SEQ ID NO:11; Poa p IX — SEQ ID NO:12)

Individual protein components were isolated using preparative isoelectric focussing on the Rotofor (Biorad, Richmond, Calif.). The proteins were separated on SDS-PAGE, and transferred to PVDF membrane (Millipore, Bedford, Mass.). N-terminal sequencing was performed according to Matsudaira (1987) *J. Biol. Chem.* 262: 10035–10038, and Simpson et al. (1989) *J. Chromatogr.* 476: 345–361.

The 31/33 kD protein, Lol p Ib, has a different N-terminal amino acid sequence from Lol p I (Cottam et al. (1986) *Biochem J.* 234: 305–310; Table 2), described herein as Lol p Ia. It is concluded that the allergen encoded by clone 12R represents a major newly identified allergen, Lol p Ib.1. The nucleotide sequence of clone 12R is shown in FIGS. 3*b* and 3*c* (SEQ ID NO:1).

Example 3

Pollen-specific expression of allergens

Poly A+ RNAs were isolated from different plant tissues: seed, leaf, root and pollen. 20 ug of total RNA from the different tissues was electrophoresed on a 1.2% w/v agarose gel in the presence of formamide and formaldehyde (Sambrook, et al., supra), transferred to Hybond-C extra (Amersham, Arlington Heights, Ill.) and the filters baked at 80°0 C. for 2 h. The 1.2 kb 12R cDNA was radio-labelled with $^{32}$P and incubated with the NC filter at 65° C. in the presence of 50% v/v formamide. The membrane was washed with 2×SSC (0.3M NaCl, 0.3M sodium citrate, pH 7.0) containing 0.1% w/v SDS at 65° C. Proteins were isolated from the different tissues (flower, leaf, root and pollen) by grinding in 10 mM PBS containing 1 mM PMSF, and immunoblotted (10 ug protein per lane) with the indicated antibodies. The binding was visualized by using $^{125}$I-goat anti-mouse Ig (Amersham, Arlington Heights, Ill.) for MAbs, and polyclonal $^{125}$I-goat anti-human IgE (Kallestad, Chaska, Minn.) followed by autoradiography.

Figure 2A:
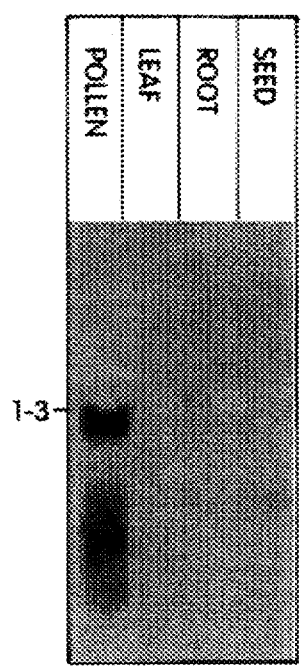
FIG. 2a shows RNA blot hybridization. Poly(A)+RNAs were isolated from different plant tissues: seed leaf, root and pollen.
Figure 2B:
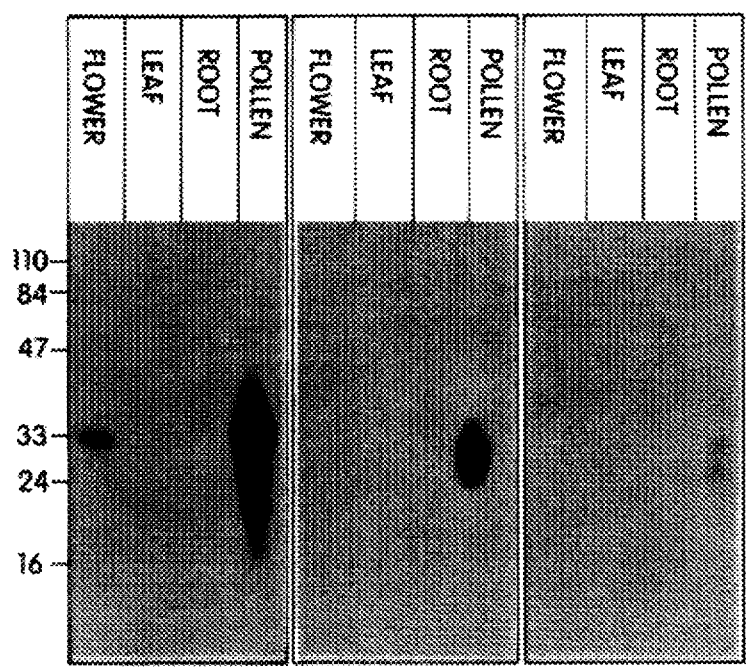
FIG. 2b shows immunoblot analysis of tissue-type and cell-type specific distribution of group Ib antigens. The soluble proteins were extracted from different plant tissues: flower, leaf root and pollen, and were immunoblotted using MAbs 40.1 (panel 1), 12.3 (panel 2) and IgE antibodies (panel 3).

Northern blot analysis of RNA prepared from pollen showed high levels of expression of the cloned allergen gens in pollen but not in any vegetative tissues. A prominent band approximately 1.3 kb long observed in pollen RNA is not detectable in RNA from vegetative tissues (FIG. 2*a*). Pollen-specific RNA expression corresponded to pollen-specific expression of antigens recognized by MAbs 40.1, 12.3 and IgE antibodies (FIG. 2*b*). Specific binding occurred only when pollen and floral tissues (containing pollen) were used as protein source.

Example 4

Primary Structure Analysis

The cDNA clone 12R was isolated and subcloned into pGEM-3Z vectors (Promega, Madison, Wis.) and restriction mapped. Various sized restriction fragments were subcloned into pGEM vectors.

The isolated cDNA clone 12R was also subcloned into pBluescript II vectors (Stratagene, La Jolla, Calif.) and used to transform XL1-Blue cells (Stratagene, La Jolla, Calif.). DNA sequence was determined by double-stranded sequencing carried out by the dideoxy chain termination method (Sanger et al. (1977) *Proc. Natl Acad. Sci. USA* 74: 5463–5468) using T7 DNA polymerase (Pharmacia, Piscataway, N.J.). Nested deletions were generated from both the T7 and T3 ends using Exo III and S1 nuclease. Plasmid DNA was prepared using a modified alkaline lysis procedure. Deletion clones were size selected for DNA sequencing by electrophoresis on agarose gels. DNA sequencing was performed using T7 DNA polymerase and dideoxy nucleotide termination reactions. [$^{35}$S]dATP was used as the label. Sequencing reactions were analyzed on 6% polyacrylamide wedge gels containing 8M urea. Internal sequencing primers were synthesized as necessary. The reading frame was confirmed by sequencing two expression subclones in pGEM vector as detailed in FIG. 4. DNA sequence data were analyzed using the PC GENE System (Intelligenetics, Mountain View, Calif.).

The nucleotide sequence of the cDNA clone 12R is GC-rich (61% GC, FIGS. 3*b* and 3*c* (SEQ ID NO:1). As shown in FIGS. 3*b* and 3*c*, there is an open reading frame of 903 bp starting with an ATG initiation codon at nucleotide 40 and terminating with a TGA codon starting at nucleotide 943. The proposed translation initiation site and its flanking sequences share 89% homology with the consensus plant sequence AACAATGGC (nucleotides 36–44 of SEQ ID NO:1), and can be considered as in optimum context with the presence of a purine at position −3 (nucleotide 37 of SEQ. ID. NO:1) from the methionine codon. (Cavener and Ray (1991), *Nucleic Acid Res.*, 19:3185–3192) The open reading frame encodes a protein of predicted Mr 29.8 kD.

The predicted protein sequence, which is rich in alanins (32%), has a putative signal or target peptide sequence of 25 amino acids (amino acids −25 through −1 in FIG. 3*b* and SEQ ID NO:2). This is indicative of a cleaved protein of predicted Mr 27.3 kD. The N-terminal protein sequence of Lol p Ib is identical to the deduced amino acid sequence of clone 12R immediately after the putative cleavage site of the signal peptide sequence. This confirms that the cDNA-12R encodes a Lol p Ib allergenic protein and that the protein has a signal peptide sequence which is cleaved. The protein encoded by the 12R clone has been designated Lol p Ib.1 (SEQ ID NO:2). The deduced amino acid sequence of Lol p Ib.1 is also shown in FIGS. 3*b* and 3*c*).

Figure 3D:
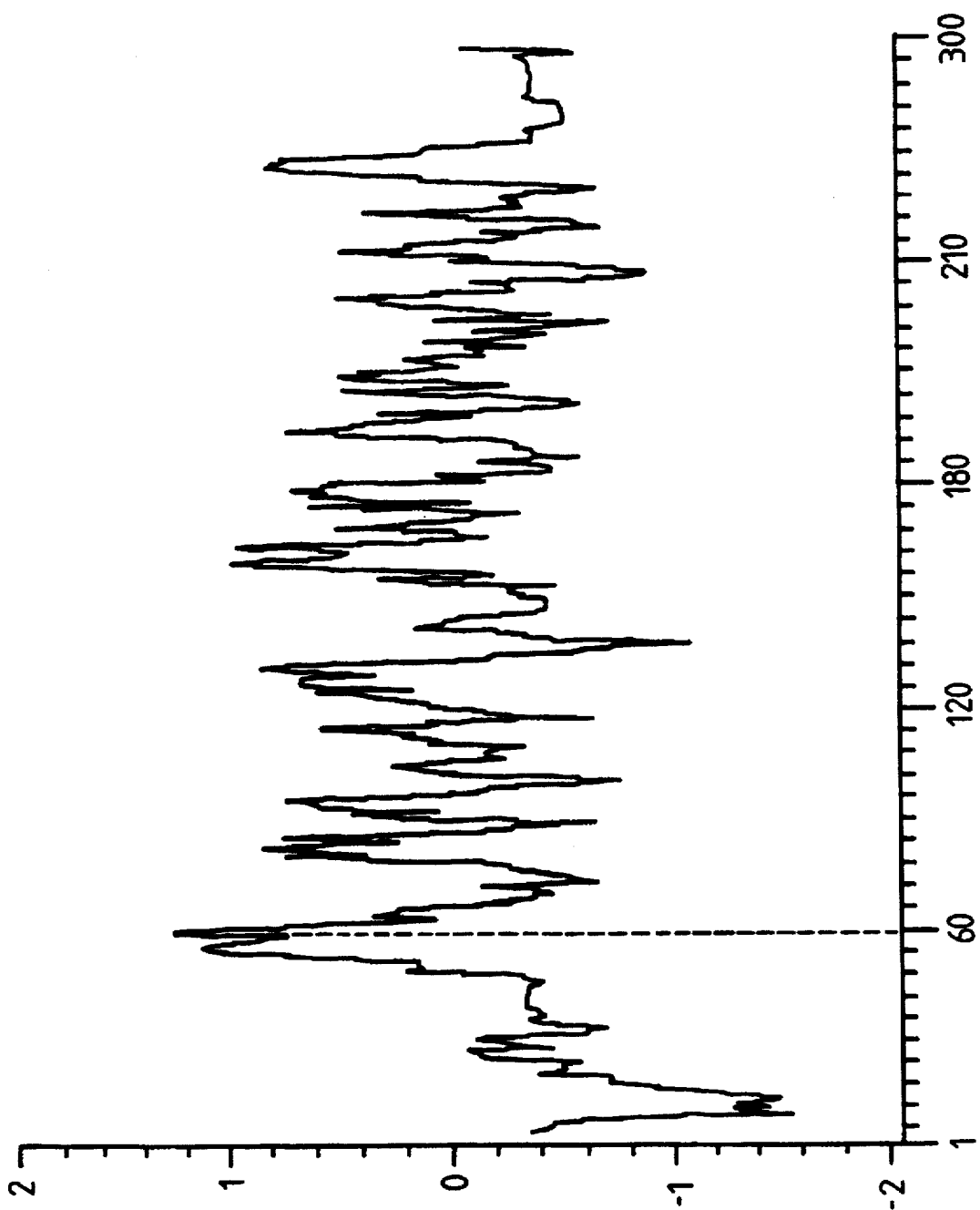
FIG. 3d shows the hydrophilicity profile of predicted amino acid sequence based on method of Hopp and Woods (1981) Proc. Natl Acad. Sci. USA 78: 3824–3828, with a window of seven amino acids.

The signal sequence has features that are typical of other eukaryotic sequences: a relatively hydrophilic sequence of 5 amino acids at the C-terminus, a relatively hydrophobic sequence extending over most of the signal region which becomes more hydrophilic at the N-terminus (FIG. 3d). The amino acids at the C-terminus include alanins at the cleavage site, an aromatic residue tyrosine at −2, and a helix breaker proline at −6, all of which are common features of the C-terminal region of a signal sequence.

A search for consensus glycosylation sequences (Asn-X-Ser/Thr) in the deduced amino acid sequence detected no such sequences. The absence of an N-linked carbohydrate chain on the allergen was confirmed by the lack of deglycosylation following treatment with the enzymes N-glycanase and endo-F glycosidase. Chemical deglycosylation followed by SDS-PAGE showed no decrease in molecular weight of the protein. The 31/33 kD components remained as a doublet, suggesting that the difference in molecular weight is not due to glycosylation. The deglycosylation treatments did not affect IgE binding to the 31/33 kD components. As compared to Lol p Ia which has 5% carbohydrate, no carbohydrate is present in Lol p Ib.

The amino acid sequence for Lol p Ib and deduced amino acid sequence of Lol p Ib.1 show protein sequence homology with the published amino acid sequences determined for Phl p V (Matthiesen and Lowenstein (1991) Clin. Exp. Immunol. 21:297–307) and Dac g V (Walsh et al. (1989) Int. Arch. Allergy Appl. Immunol. 91:419–425) from direct protein sequencing and deduced from a Poa p IX cDNA clone (Silvanovich et al. (1991) J. Biol. Chem. 266:1204–1210). These sequence homologies are indicated in Table 2.

Example 5

Delineation of IgE- and Mab-Reacting Epitopes

To localize MAb and IgE determinants, an E. coli recombinant expression system was employed (Smith and Johnson (1988) Gene 67: 31–40). Using this system, a number of restriction fragments were subcloned into the expression plasmid pGEX 1-3. The "in frame" sub-cloning of full length cDNA into pGEX, expressed the 61 kD fusion protein recognized by both IgE and MAbs 40.1 and 12.3.

The full length cDNA 12R or two restriction fragments 1H and 2P (shown in FIG. 4), were subcloned into plasmid expression vector pGEX. The procedure for inducing fusion proteins and preparation of bacterial lysates have been described earlier (Smith and Johnson, supra). The lyeares obtained were subjected to reducing SDS-PAGE, followed by transfer to NC membranes. The blots were probed with IgE antibodies, and MAbs 40.1 and 12.3 as described in relation to FIG. 1b, except that $^{125}$I-anti-human IgE (Kallestad, Chaska, Minn.) was used to detect IgE binding.

Figure 4:
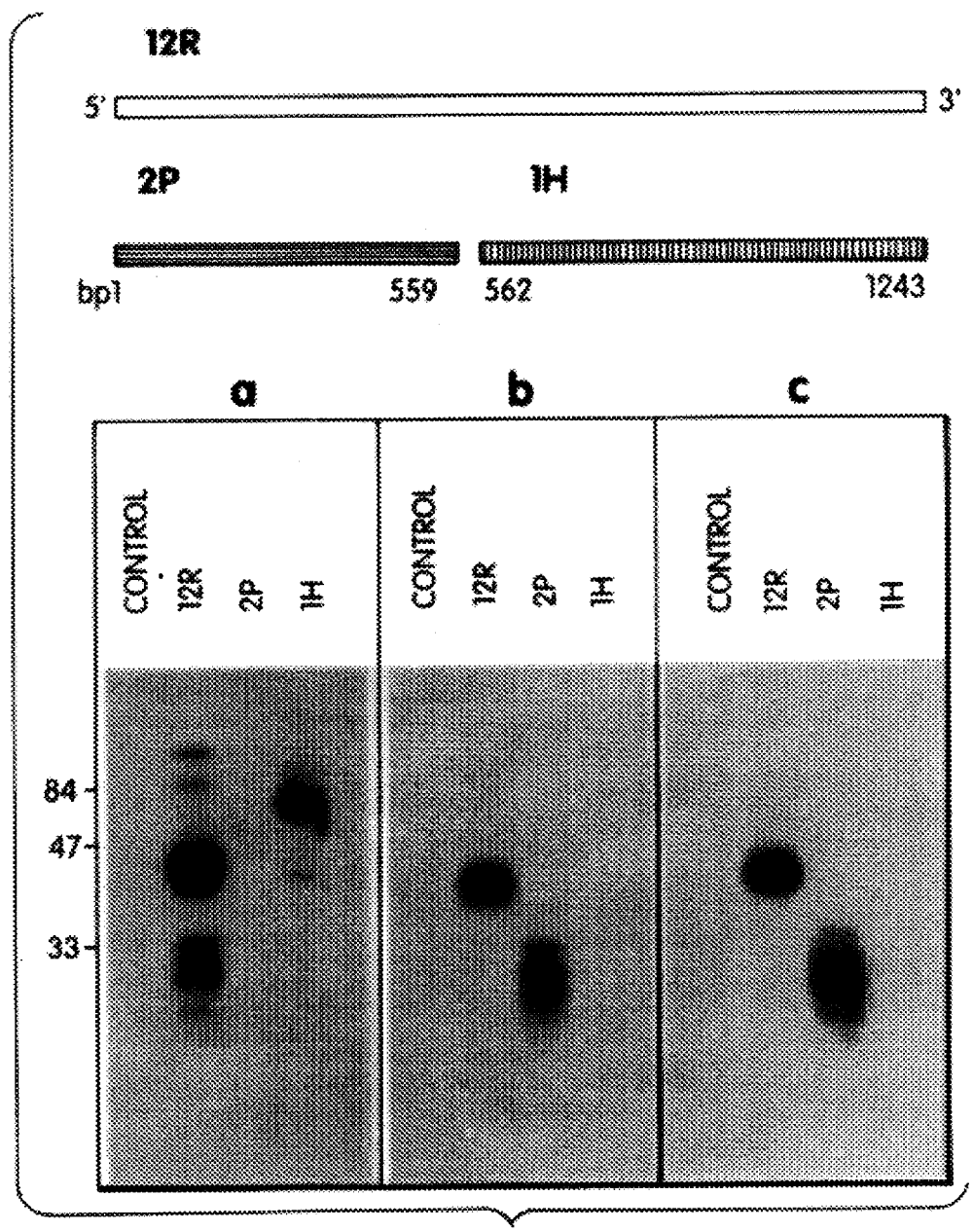
FIG. 4 shows the delineation of IgE and MAb-reacting epitopes in Lol p Ib.1 (clone 12R) using immunoblotting.

Immunoblot analysis showed that most of the fusion protein produced is cleaved by bacterial proteases near its fusion site with glutathione-S transferass, generating breakdown products which are recognized by IgE antibodies (FIG. 4). The recombinant fusion protein expressed by fragment 2P (GST-2P), although strongly reactive with both MAbs, was not recognized by IgE antibodies in pooled allergic sera. However, the N-terminally truncated protein produced by fragment 1H (GST-1H) was not recognized by either of the MAbs, but was highly reactive with the IgE antibodies.

In this way, two distinct domains of the allergen molecule have been delineated: the N-terminal containing fragment 2P has recognition sites for MAbs 12.3 and 40.1; and the C-terminal containing fragment 1H which shows strong IgE binding and thus has the allergenic determinant(s). Because the two MAbs have different binding specificities (FIG. 1b), the recognition sites for the two MAbs are likely to be different, although in the same fragment. Fine mapping with smaller fragments is needed to delineate the 12.3 and 40.1 binding sites, but these results are sufficient to show that the IgE determinant is different.

Example 6

Intracellular Targeting Of Lol p Ib In Ryegrass Pollen

Mature pollen of Lolium perenne was prepared for scanning electron microscopy according to established methods (Staff et al. (1990) Histochem J. 22: 276–290). For immunocytochemistry, mature anthers were fixed under anhydrous conditions: 0.1% glutaraldehyde, 1% paraformaldehyde in 2,2-dimethoxypropane at 4° C. for 2 h and processed for transmission electron microscopy (Staff et al., supra). This method has been developed to reduce diffusion of the allergens from their cellular sites in aqueous media. Blocks were polymerized in LR gold resin with 1% benzil at −25° C. under UV illumination and 80 nm thin sections picked up on gold grids. Immuno-labelling was first with primary antibody, MAb 12.3 (specific for Lol p Ib) followed by gold-goat-anti-mouse IgG probe (15 nm particle size). This label was silver-enhanced to 40 nm particle size (modified from Danscher & Norgaard (1983) J. Histochem. Cytochem. 31:1394–1398). A second labelling was performed on the same sections with a mixture of three MAbs, 3.2, 21.3 and 40.1 followed by gold-goat-anti-mouse IgG probe with 15 nm particle size. Antibody specificity and method controls run as described previously (Staff et al., supra) showed no gold particles at these sites.

Figure 5A:
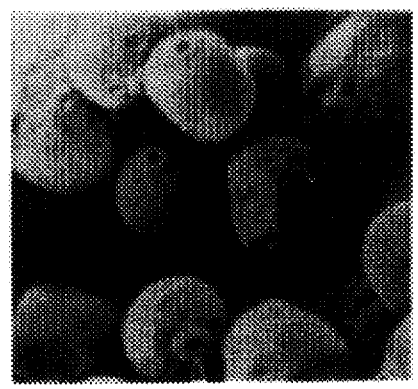
FIG. 5a shows whole pollen grains visualized by scanning electron microscopy, showing the single germinal pore. Scale bar, 30 um.

Lol p Ia is located in the cytosol and not in the organslies. These findings were obtained using immuno-gold probes with MAbs specific for Lol p Ia. As shown herein, MAb 12.3, which is specific for Lol p Ib, binds predominantly to the starch grains (FIGS. 5a, b). Grass pollen is filled with starch grains which are 1×2.5 um in size, and originate in the lumen of amyloplasts.

Figure 5B:
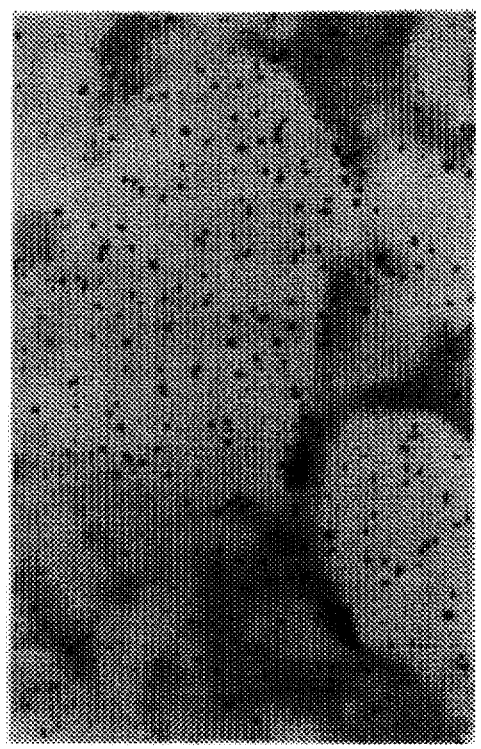
FIG. 5b shows detection of cellular sites of Lol p Ia and Lol p Ib by immuno-gold localization—double labelling.
Figure 5C:
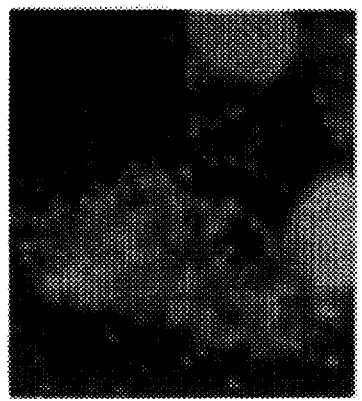
FIG. 5c shows the appearance of fresh, viable pollen after exposure to water for 30s, dark field illumination.

As shown in FIG. 5b, the large gold particles located predominantly over the starch grains (large electron-lucent spaces) show binding of MAb 12.3 to Lol p Ib, while smaller particles over the cytosol are typical of binding to Lol p Ia. Scale bar is 1 um. FIG. 5c shows the appearance of fresh, viable pollen after exposure to water for 30s, dark field illumination. Most pollen grains burst, extruding their cytoplasmic contents, including starch grains (white particles) through the germinal pore. Scale bar, 30 um.

The localization of Lol p Ib in the plastids implies that this protein should be transported from the cytosol to the lumen of the plastids during development. For transport to chloroplasts, the proteins which are synthesized in the cytosol are synthesized as large precursors containing a target peptide sequence that is cleaved after transport into the organelle. These intracellular processing steps, synthesis of Lol p Ib first as a pre-allergen in the cytosol and transport to the plastid for post-translational modification, may explain the appearance of the doublet 31/33 kD found by immunoblotting. The unprocessed pre-allergen is 33 kD, and after processing in the plastids, the mature protein is 31 kD. Both these forms co-exist in mature pollen. Alternatively, this doublet may also represent different isoforms or family members of Lol p Ib.

Example 7

Presentation of Lol p Ib to the immune system

When the rye-grass flower opens, the anthers are exerted and the pollen is released into the air through a pore which opens at the base of each anther. Rye-grass shows the greatest pollen production of any grass, releasing approximately 460 kg of pollen per hectare into the atmosphere in pastures that are not mowed or grazed. Ninety-nine per cent of this pollen is deposited (and re-deposited) within 1 km of its source. Grass pollen is short-lived, yet it can remain for several days in the atmosphere. Experiments show that the pollen remains viable for only a few hours after release.

When viable, the grains can germinate on the stigma, or in artificial media with high levels of osmoticum. Living viable rye-grass pollen grains when exposed to water, burst at the single germinal aperture releasing the cytoplasmic contents (FIG. 5c). Prominent among the released contents are the starch grains. Media with high osmoticum, e.g. 30% w/v sucrose are required to maintain tonicity of the grains. In contrast, it is well-known that dead pollen grains which have no permeability barriers, act like a sponge. Cellular proteins, including allergens, are released from the surface upon moistening.

It is easy to see how grass pollen can trigger hay fever after contacting the oral and eye mucosa, by direct release of the allergens. The pollen grains themselves remain on the surface of the mucosa, but the released allergenic protein pass through the mucosa and subepithelial layers where they interact with basophils and mast cells. It is less easy to see how pollen grains as large as 30–50 um in diameter can induce allergic asthma, a disease triggered allergens sence of allergens in the airways of the lungs.

Recent evidence suggests that grass pollen allergens are associated with smaller micronic particles found in the atmospheric aerosol. The original of such particles is obscure. From the present results on allergen localization, and observations on pollen behavior in water, a new hypothesis is proposed to explain how grass pollen can induce allergic asthma in the lungs of susceptible humans. Starch grains are released as micronit particles into the atmospheric aerosol when the living pollen grains encounter water vapor, or water on the surface of a leaf or other substrata. These particles, both coated and filled with allergens, act as vehicles for allergen presentation to the upper and lower respiratory tract. Micronic particles can also, of course, results from the leaching of allergens from grass pollen and deposition on other components of the atmospheric aerosol.

Example 8

Monoclonal Antibodies Against Lol p Ib.1

Monoclonal antibodies (MAbs) were prepared against fusion protein GST-1H from Example 5 using techniques that are well known to those skilled in the art (see for example, Kohler and Milstein, supra, and Kohler and Milstein, supra). The fusion protein encoded by fragment 1H (FIG. 4), which corresponds to the IgE binding domain, is antigenic.

Four female BALB/c mice were injected intraperitoneally (i.p.) with 100 mg of FPLC purified GST-1H fusion protein in 0.1 ml PBS and 0.1 ml RIBI adjuvant (Immunochem. Res., Hamilton, Mont.). Fourteen days later a booster i.p. of the same material was given. After ten days the mice were bled. The serum was screened for binding to Western blots of total ryegrass pollen proteins and the mice were selected on the basis of this serum binding to the blot. Fourteen days later the mouse selected for fusion was given an i.p. booster of 0.2 ml containing 100 mg fusion protein only. Four days later the mouse was sacrificed and the spleen removed for fusion with myeloma cells (a gift from the Veterinary Research Institute, Parkville, Victoria, Australia). The methods used for fusion and culture were based on those of Harlow and Lane (1990) Antibodies, A Laboratory Manual, (Cold Spring Harbor Laboratory Press, Cold Spring Harbor, N.Y.), using RPMI and Hybridsera (Commonwealth Serum Laboratories, Melbourne, Victoria, Australia). Aminopterin selection was used (50×HAT and HT solutions, Flow Laboratories, Scotland, U.K.) Cloning was by limiting dilution.

Monoclonal lines were isotyped using a mouse monoclonal antibody isotyping kit (Amersham International, U.K.). Human allergic sera were collected, after informed consent, from patients who showed typical symptoms of seasonal hay fever during the grass pollen season and gave a positive response to a skin prick test. The sera were assayed for IgE reactivity with total proteins of ryegrass pollen on Western blots. The pollen samples were purchased from Greet Laboratories (Lenoir, N.C.). Soluble proteins were extracted from the grass pollen by vigorous shaking in PBS containing 1 mM phenyl-methylsulfonyl fluoride on ice for three hours. The protein concentration for each sample was determined using Bio-Rad (Richmond, Calif.) protein assay.

The antibody binding of each grass was initially detected by slot immunoblotting. 100 μl sample containing 2 mg of total pollen proteins was applied to the nitrocellulose membrane using a Minifold II slot blotting apparatus (Schleicher and Schuell, Dassel, Germany). this was washed in PBS and blocked in the same buffer containing 10% milk powder.

SDS-PAGE was carried out with a 10–15% acrylamide gradient gel utilizing a Bio-Rad (Richmond, Calif.) Protean II slab gel apparatus and the Laemmli buffer system (Laemmli, U.K. (1970) Nature 227: 680). The proteins were visualized by Coomassie Blue R250 (Sigma Chemical Co., St. Louis, Mo.) staining. Proteins separated by gradient SDS-PAGE were electrophoretically transferred from the gel onto nitrocellulose membrane according to the procedure of Towbin et al., (1979) Proc. Natl. Acad. Sci. USA 76: 4350–4354, in a Bio-Rad (Richmond, Calif.) transblot cell. The proteins on the nitrocellulose were detected by blocking the non-specific sites by incubating the membrane in milk powder as described for slot blots. The membrane was then washed in PBS and immersed in either the MAb solution for two hours or overnight in human serum (a pool of sera obtained from 10 grass-allergic patients) diluted 1:5 in PBS containing 0.5% BSA and 0.1% sodium azide. The membrane, incubated in the MAb solution, was washed in PBS, then incubated with sheep anti-mouse IgG-horseradish peroxidase (Silenus, Australia) diluted 1:500 in PBS-BSA. After washing, the serum blot was first incubated in a solution of rabbit anti-human IgE (Dakopatts, Glostrup, Denmark) diluted 1:200 in PBS-BSA for two hours and then in a solution of goat anti-rabbit IgG-horseradish peroxidase (Promegal, Madison, Wis.) diluted 1:2500 with PBS-BSA for one hour. After washing the antibody binding to the blots was visualized by incubating in peroxidase substrate solution containing 4-chloro-1-napthol and hydrogen peroxide.

The fractions containing the GST-1H fusion protein were fractions 9 and 10 as eluted from the FPLC column. These fractions, when analyzed by SDS-PAGE revealed a single band of 41 kD (GST-1H) corresponding to 26 kD GST and 15 kD protein encoded by fragment 1H.

During MAb production, one fusion resulted in 75 wells containing cell colonies, 7 of which were positive to native Lol p Ib pollen proteins. Three strongly growing colonies were cloned to produce MAb lines. When isotyped two lines produced IgG kappa antibodies, designated LpIX-3A and LpIX-4A, and one produced IgM kappa antibody. In a similar fashion, the MAb LpI-7E (7E) was generated using soluble pollen extract as an antigen. MAb LpI-7E is specific for Lol p Ia.

Figure 6:
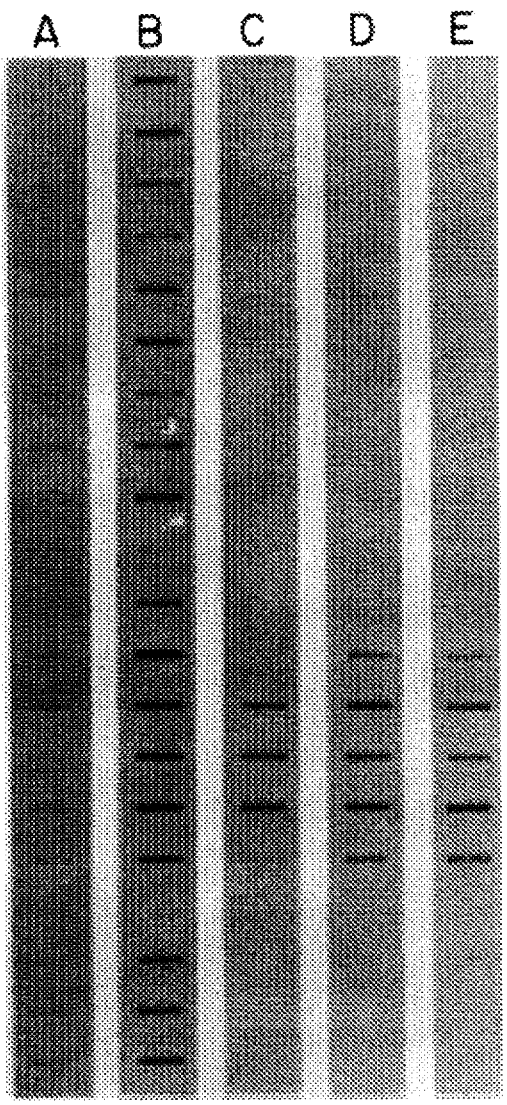
FIG. 6 shows antibody binding to non-denatured pollen proteins from 20 different grasses. Lanes A through E shown binding of various antibodies to the pollen proteins in the listed grass species—lane A) IgE, lane B) FMC-A1 antibody, lane C) FMC-A-7 antibody, lane D) LpIX-3A antibody, and lane E) LpIX-4A antibody.
Figure 7A:
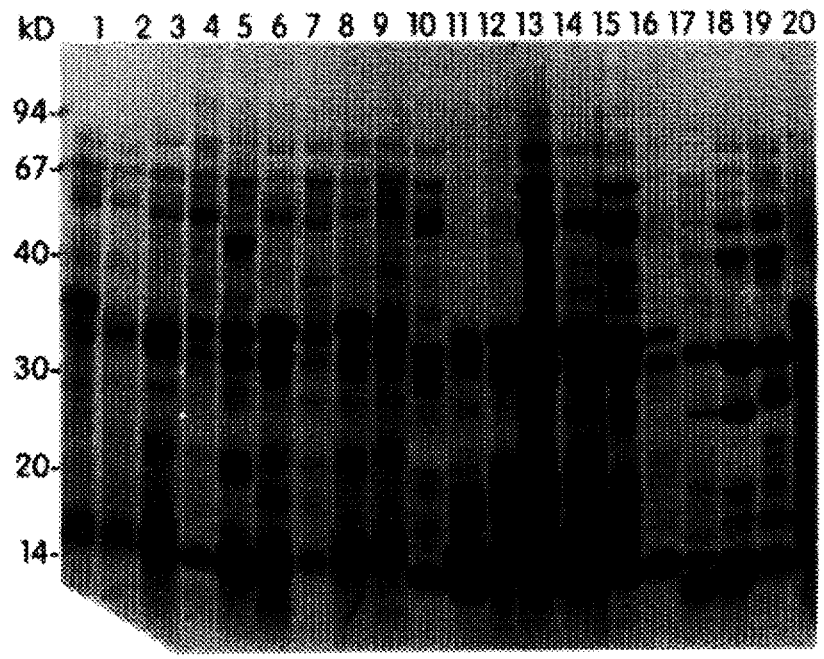
FIG. 7 shows soluble pollen proteins of 20 different grasses separated by gradient SDS-PAGE and visualized by Coomassie Brilliant Blue R250 staining (FIG. 7a), and binding of serum IgE (FIG. 7b), monoclonal antibody FMC-A1 (FIG. 7c), monoclonal antibody FMC-A7 (FIG. 7d), antibody LpIX-3A (FIG. 7e) and antibody LpIX-4A (FIG. 7f). Individual lanes correspond to the grasses shown in FIG. 6.
Figure 7B:
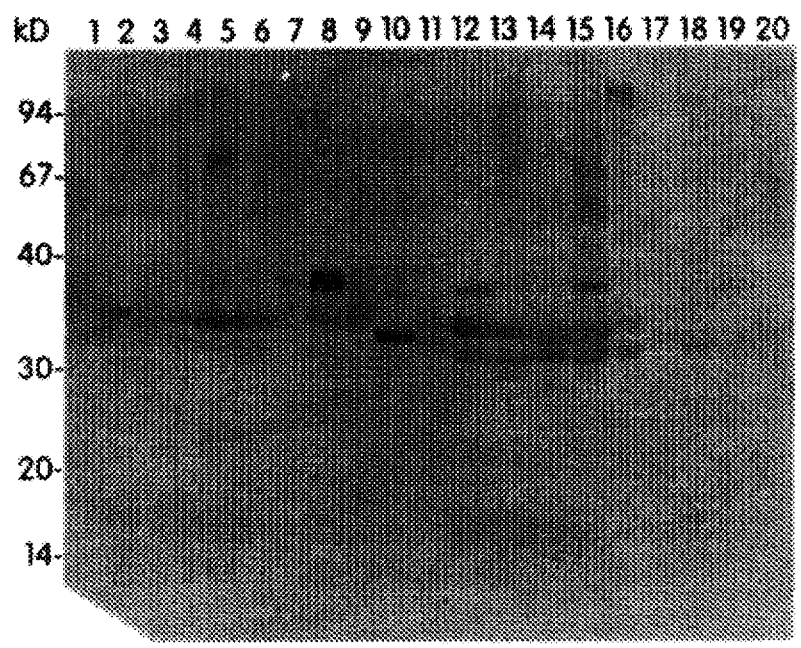
Figure 7C:
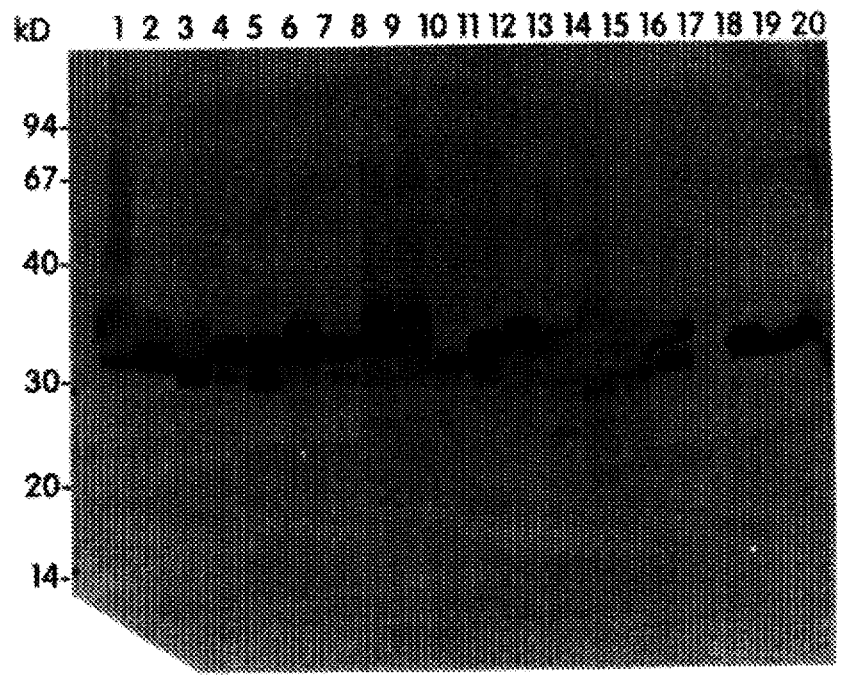
Figure 7D:
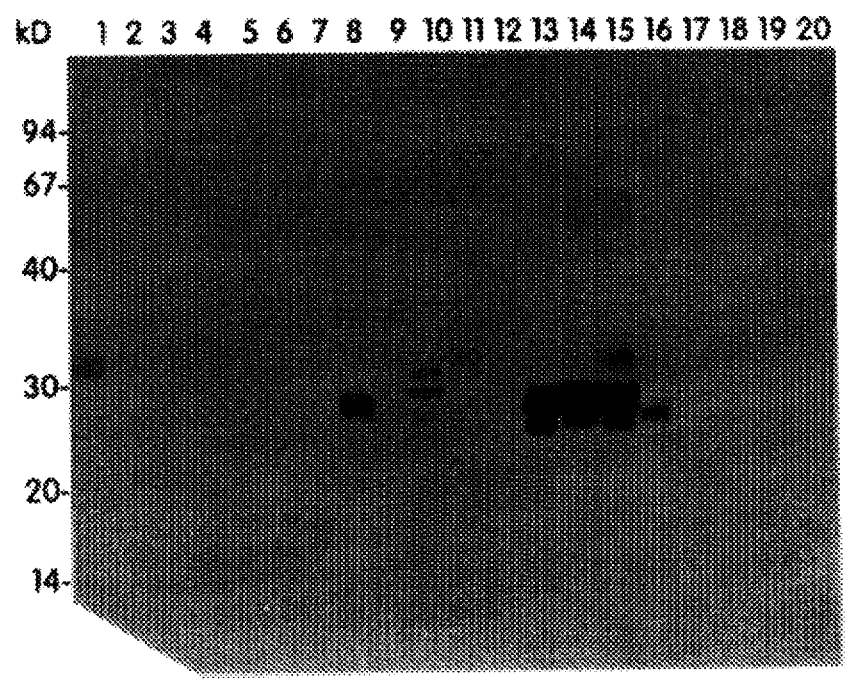
Figure 7E:
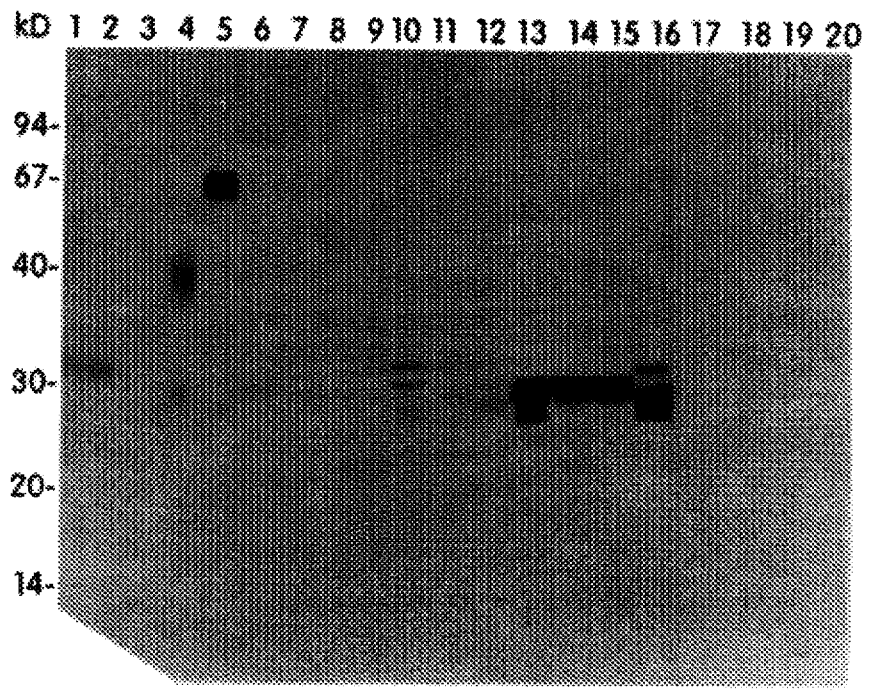
Figure 7F:
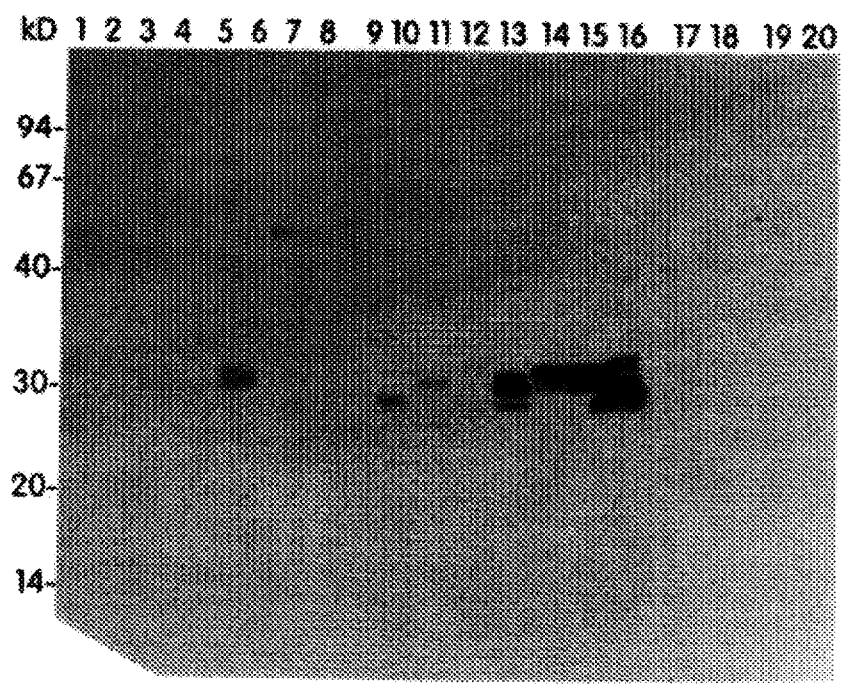

These MAbs bind to non-denatured antigens in the pollens of Dactylis glomerata, Festuca elatior, Lolium perenne, Lolium multiflora and Poa pratensis (FIG. 6). On Western blots of soluble pollen proteins separated by SDS-PAGE, MAbs LpIX-3A and LpIX-4A bind to antigens in Festuca elatior, Lolium perenne, Lolium multiflora and Poa pratensis (FIG. 7). These grasses are all taxonomically related. They are members of the tribe Poeae, supertribe Poadae, subfamily Pooideae.

Example 9

Isolation of cDNA Clone 19R Encoding Lol p Ib.2 Immunological Screening

Duplicate filters of the cDNA expression library in Example 1 were screened with specific IgE from pooled human allergic sera. The bound IgE was detected using $^{125}$I-labelled anti-human IgE (Kallestad Laboratories, Chaska, Minn.). The plaques that were antibody-positive on both of the duplicate filters were picked off, purified, and then replated and tested for binding to MAbs.

Figure 8:
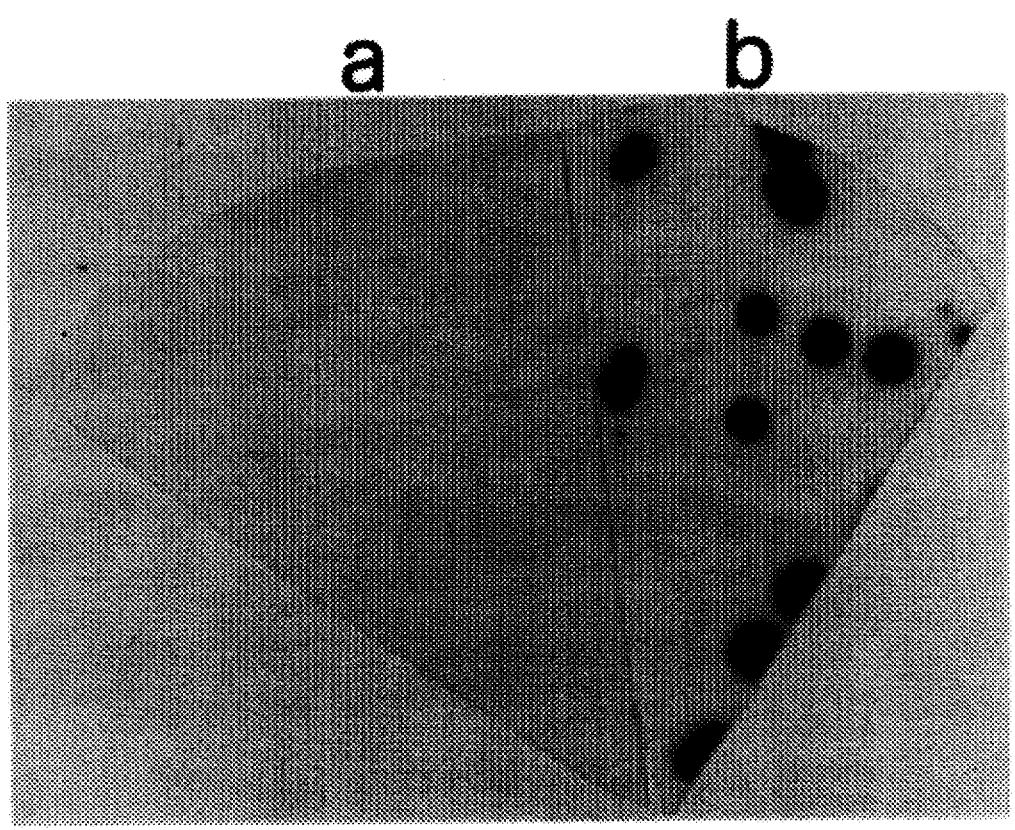
FIG. 8 is a photographic representation of immunoscreening of clone 19R in the vector lambda gt 11 using pooled sera from (a) allergic patients and (b) non-allergic patients.

Plaque purified clone 19R was not positive when tested with non-allergic sera (FIG. 8). This showed that clone 19R is an allergen by its ability to bind specific IgE in sera of ryegrass sensitive patients.

Figure 9:
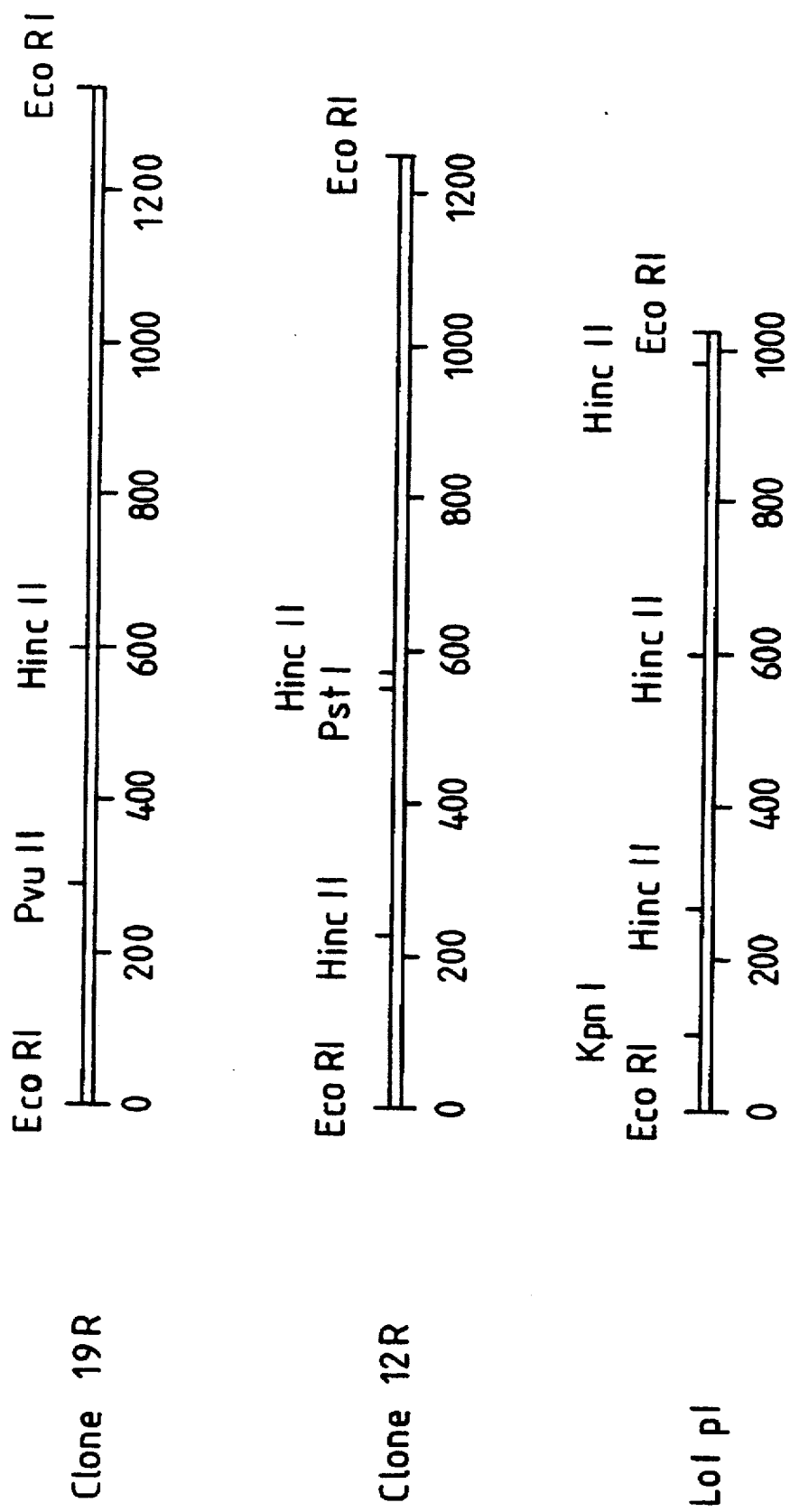
FIG. 9 is a schematic representation showing a partial restriction endonuclease map of Lol p Ib.2 (clone 19R), Lol p Ib.1 (clone 12R) and Lol p Ia.

Clone 19R was digested with EcoRI and ligated into pGEM plasmid (Promega, Madison, Wis.). FIG. 9 shows a partial restriction map of the subcloned EcoRI insert from clone 19R compared to restriction maps of the genes encoding Lol p Ib.1 and Lol p Ia. The insert is different from those encoding Lol p Ia and Lol p Ib.1, as shown in FIG. 9. The size of the EcoRI insert is about 1295 bp.

Subcloning and Sequencing of DNA

DNA was prepared from plague-purified phase using the liquid lysate method as described in Meese, E. et al., (1990) Nucleic Acids Res., volume 18:1923. Inserts recovered from EcoRI digestion were ligated into pGEM4-Z (Promega, Madison, Wis.) and subcloned as various-sized restriction fragments into pGEM vectors (pGEM4-Z). All sequencing was done using double stranded plasmid templates. These templates were prepared as described in the Qiagen, Inc., Chatsworth, Calif., U.S.A.). Dideoxy sequencing (Sanger et al, (1977) Proc. Nat'l. Acad. Sci. USA, 74:5460–5463) was performed as described in Example 4. 7-deaza dITP was used to resolve severe GC band compressions. Sequencing was facilitated by generation of nested deletions from both ends of the insert with Exo III and S1 nucleases. Internal sequencing primers were synthesized as necessary.

Sequence Analysis

Sequence analysis was carried out using the Melbourne database system (MELBDBSYS), a collection of analysis programs developed at the Walter and Eliza Hall, Ludwig and Howard Florey Institutes of the University of Melbourne, Australia, and PC Gens (Intelligenetics, Mountain View, Calif.). This system incorporates databases from the following sources: GenBank, EMBL, and BPRF nucleic acid libraries; NBRF PRI protein, PSD-Kyoto (Ooi), GBtrans, Swiss-Prot, and Doolittle protein libraries. During the searching period, EMBL and GenBank databases were releases 28.0 and 68.0 respectively.

The cDNA sequence of clone 19R is shown in FIGS. 10a and 10b (SEQ ID NO:3) and contains 1295 nucleotides. There is an open reading frame of 1017 bp starting with an ATG initiation codon at nucleotide positions 25–27 and terminating with a TGA stop codon starting at nucleotide position 1041. The cDNA of clone 19R possesses the following characteristice suggesting that it contains full-length coding regions:

i) The proposed translation initiation site and its flanking sequences (nucleotides 21–29) share 89% homology with the consensus sequence of monocot plants. The most critical nucleotide, a purine at position −3 relative to the ATG start codon (nucleotide 21 in FIG. 10a), is conserved, Caveher, D. R., and Ray, S. C. (1991) Nucleic Acids Research, 19:3185–3192;

ii) The cDNA has a complete 3'-untranslated region canonical AATTAA polyadenylation signal, Birnsteil et al. (1985) Cell, 41: 349–359, followed by a poly (A) tail; and iii) The 3'-untranslated region also contains ATTTA which may be associated with mRNA stability.

Figure 11:
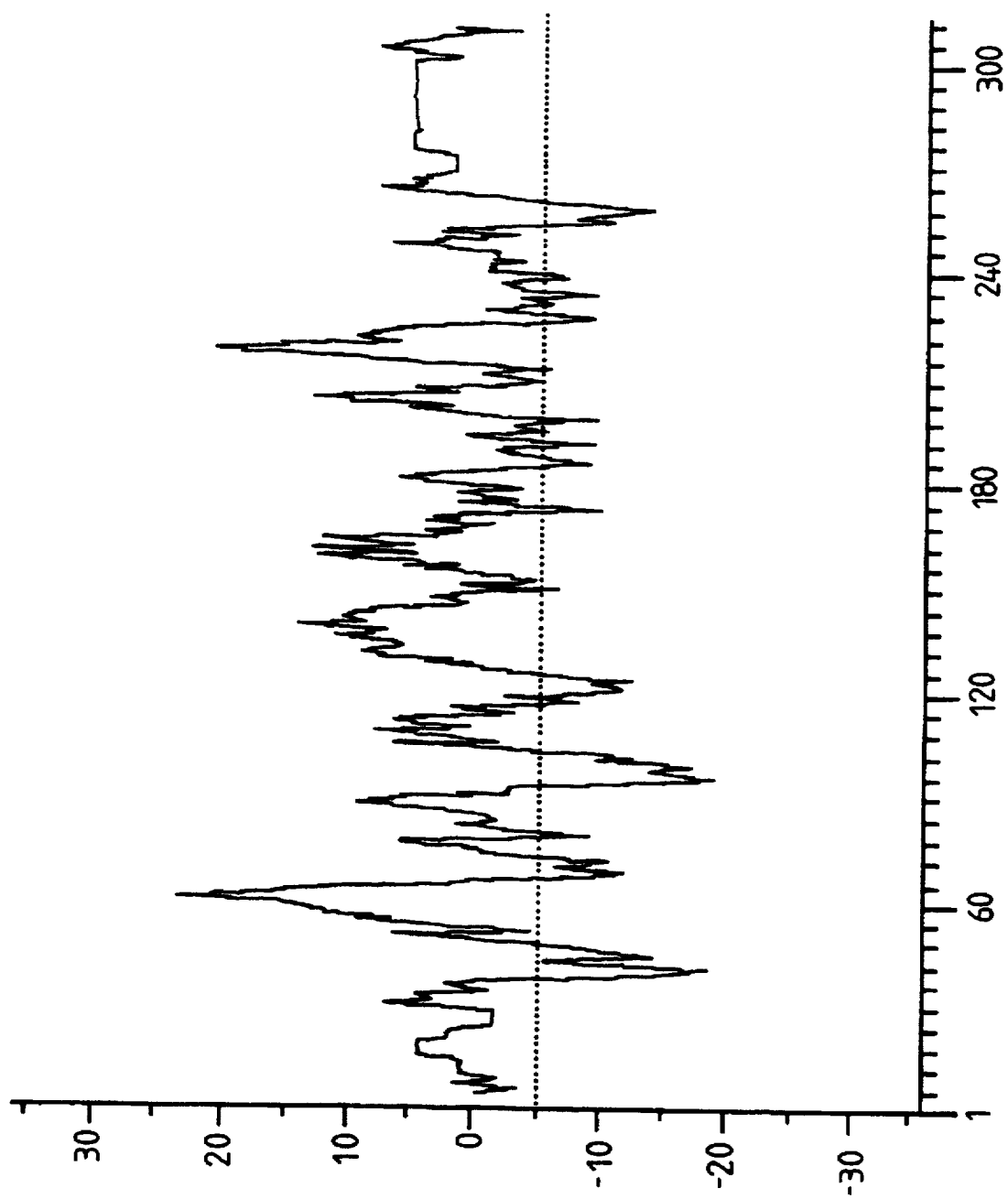
FIG. 11 is a graphical representation of a hydrophobicity profile of the predicted amino acid sequence for Lol p Ib.2 based on the method of Kyte and Doolittle (1982) *J. Mol. Biol.*, 157:105–132, with a window of nine amino acids.

The nucleotide sequence of clone 19R cDNA (SEQ ID NO:3) is G+C rich (63%). The open reading frame potentially encodes a protein, designated Lop Ib.2 (SEQ ID NO:4) of 314 amino acids with a predicted Mr of 35.3 kD. The predicted protein appears to posses a leader peptide of 25 amino acids on the basis of hydropathy profiles of the N-terminal sequence as shown in FIG. 11, which shows the hydophobicity profile of the predicted amino acid sequence based on the method of Kyte and Doolittle (1982) J. Mol. Biol., 157:105–132, with a window of nine amino acids. This suggests the molecular weight of the mature processed protein is 32.8 kD. No Asn-X-Ser/Thr sequons required for N-glycosylation are found and the predicted pI value for the mature protein is 5.9.

Nucleotide and amino acid sequence searches of existing data bases showed that clone 19R only has similarity with Lol p Ib.1 and Poa p IX allergens. There is a 72.3% homology between the nucleotide coding regions of clone 19R (SEQ ID NO:3) and clone 12R (SEQ ID NO:1), as shown in FIGS. 12a and 12b. Amino acid comparison showed 66.8% identity between the predicted amino acid sequences of clone 19R (SEQ ID NO:4), and Lol p Ib.1 (SEQ ID NO:2), as shown in FIG. 13. Both allergens have a very similar 25 amino acid leader peptide. There is a 64–69% identity between the amino acid sequences of clone 19R and the three isoallergens of Poa p IX (Silanovich et al. (1991) J. Biol. Chem., 266:1204–1210).

Isolation of Pollen Proteins and Immunoblotting

Soluble proteins were extracted from ryegrass pollen by vigorous shaking in PBS and 1 mM phenylmethylsulfonyl fluoride on ice for three hours. Conditions for SDS-PAGE were essentially as described in Ong et al. (1990) Int. Arch. Allergy Appl. Immunol., 93:338–343. Immediately after electrophoresis, the separated proteins were either silver stained (Angorge, W. (1982), in "Electrophoresis'82: Advanced Methods, Biochemical and Clinical Applications, Proceedings of the International Conference on Electrophoresis, Athens, Greece, Apr. 21–24, 1982", Editor: D. Stathakos, Walter de Gruyeer, Berlin and New York, 1983, pages 235–242) or transferred at 4° C. to nitrocellulose (Towbin et al., (1979) Proc. Natl. Acad. Sci. USA, 76:4350–4354.

For IgE antibody binding, blots were incubated in pooled allergic sera or affinity purified IgE in PBS containing 0.5% bovine serum albumin (BSA). The bound IgE was detected according to the method of Ong, E. et al., (1990) Int. Arch. Allergy Appl. Immunol., 93:338–343, using $^{125}$I-labeled anti-human IgE (Kallestad Lab, Chaska, Minn.). For MAb binding, the bound IgG was detected using horseradish peroxidase labeled sheep anti-mouse Ig (Silenus, Hawthorn, Victoria, Australia). The blot was developed using an enhanced chemiluminescence system (Amersham Int., U.K.).

Affinity Purification of IgE Antibodies cDNA clones in lambda gt 11 phages encoding allergens were expressed as fusion proteins in *Escherichia coli*. Plaque lifts, containing the recombinant fusion proteins (rfp) were then incubated in pooled sera. The bound IgE antibodies were eluted with 0.2M glycine HCL, pH 2.6/0.5% BSA/0.1% sodium azide and used to probe Western blots. Binding of IgE was visualized using $^{125}$I-labeled anti-human IgE (Kallestad, Chaska, Minn.) followed by autoradiography, Ong et al., *Int. Arch Allergy Appl. Immunol.*, 93:338–343.

RNA Blot Hybridization

For RNA gel blot analysis, total RNA was denatured in 20 mM 3-(N-morpholino)-propanesulfonic acid, 50% deionized formamide, and 2.2M formaldehyde at 65° C. for five minutes, electrophoresed in 1.2% agarose gel containing 2.2M formaldehyde, and electrolotted onto nitrocellulose. The RNA slot-blot analysis was carried out by denaturing the total RNA is 20 mM 3-(N-morpholino)-propanesulfonic acid, 5 mM sodium acetate, and 1 mM EDTA at 65° C. for ten minutes and applying the samples onto nitrocellulose saturated with 20×SSC (SSC–3M sodium chloride, 1.0M sodium citrate) fitted in the Minifold 11 Filtration Manifold (Schleicher & Schuell, Dassel, Germany). Both filters were prehybridized for two to six hours at 42° C. in a solution containing 50% deionized formamide, 2×SSPE (SSPE –3M sodium chloride, 0.2M sodium phosphate, 0.02M EDTA), 1% sodium dodecyl sulfate (SDS), 0.5% Blotto (10% nonfat milk in phosphate buffered saline), 10% dextran sulfate, and 0.5 mg/ml $^{32}$P-labelled cDNA probe prepared by random oligonucleotide priming using an oligolabelling kit (Bresatec, Adelaide, Australia). The filters were washed in four changes of 2×SSC, 0.1% SDS at 42° C. for 2 hours, and then exposed to X-ray film.

Figure 14A:
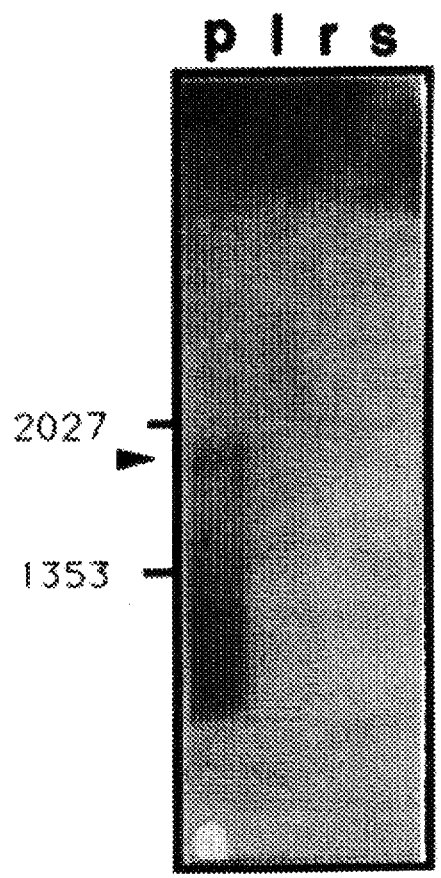
FIG. 14(a) Northern blot analysis of total RNA from ryegrass pollen, leaf, root and seed probed with a 82 base fragment specific to clone 19R.
Figure 14B:
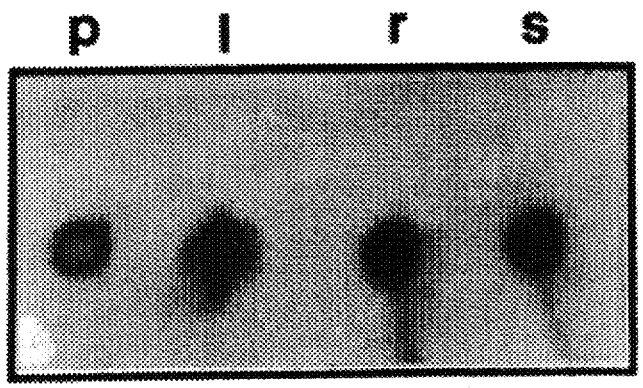
FIG. 14(b) Northern dot blot analysis of total RNA from ryegrass pollen, leaf, root and seed probed with a ribosomal DNA from *Pisum sativum*. 20 ug of total RNA was loaded in FIGS. 14(a) and (b) for all tissues.

To determine the tissue specificity of clone 19R gene expression, Northern blot analysis of RNA prepared from various *L. perenne* tissues were examined. The Northern blot was probed with an 84 bp Ssp I/Eco RI restriction fragment from clone 19R. This cDNA probe, corresponding to nucleotides 1207 to 1291 of clone 19R (FIG. 10b) that binds to clone 19R but not clone 12R, hybridizes to a single transcript of 1780 bases in pollen. No hybridization to any transcripts in ryegrass seed, root and leaf was observed. A positive control hybridization using a complete ribosomal DNA from Pisum sativum as the probe, showed that the amount of RNA used was sufficient for detection in all the samples. This is shown in FIGS. 14a and 14b.

Example 10

Construction of a Random Fragment Lambda gt 11 Library of Clone 19R

The full length (1295 bp) EcoRI insert DNA of the lambda gt 11 clone 19R was isolated and the insert DNA, containing complementary EcoRI ends, was self-ligated overnight at 14° C. and extracted twice with phenol/chloroform/isoamyl in the ratio 25:24:1. The aqueous phase was than extracted once with chloroform/isoamyl. Sodium acetate was added to 0.3M, and the DNA was precipitated with 2.5 volume of ethanol at −70° C. overnight. The DNA was pelleted, washeand resuspendev) ethanol and resuspended in 300 µl of 10 mM MgCl and 1 mM dithiothreitol. The DNA was then sonicated using a Branson sonifer 450 (Branson Sonic Power, Danbury, U.S.A.) at 0° C. for 15 one-minutes bursts. The degree of shear was monitored by agarose gel electrophresis. The fragments produced were treated with Klenow polymerase (Promega, Madison, Wis., U.S.A.) for 1.5 hours in the presence of dNTPs. Blunt-ended DNA fragments were ligated to an 80-fold molar excess of phosphorylated EcoRI linkers (New England Biolabs, Beverly, Mass., U.S.A.) and then digested with EcoRI. This mixture was heated at 70° C. for five minutes, and fractionated by 9% polyacrylamide gel electrophoresis (PAGE). DNA fragments in the range 72–118 and 118–310 bp were recovered by elution into 2M ammonium acetate, 10% SDS and 0.5M EDTA at 37° C., extracted with phenol, and ethanol precipitated. EcoRI-linkered fragments were ligated to alkaline phosphatase treated lambda gt 11 arms (Promega, Madison, Wis.). The ligated DNA was packaged, and plaques were grown in *E. coli* Y1090.

Immunological screening was done by plating the libraries and duplicate filters were produced. One of the filters was screened with the pooled allergic sera and the other was screened with MAbs PpV1 and PpV4 provided by F. Matthiesen (ALK, Horsholm, Denmark). The bound antibodies were detected using standard chromogenic methods.

Figure 15:
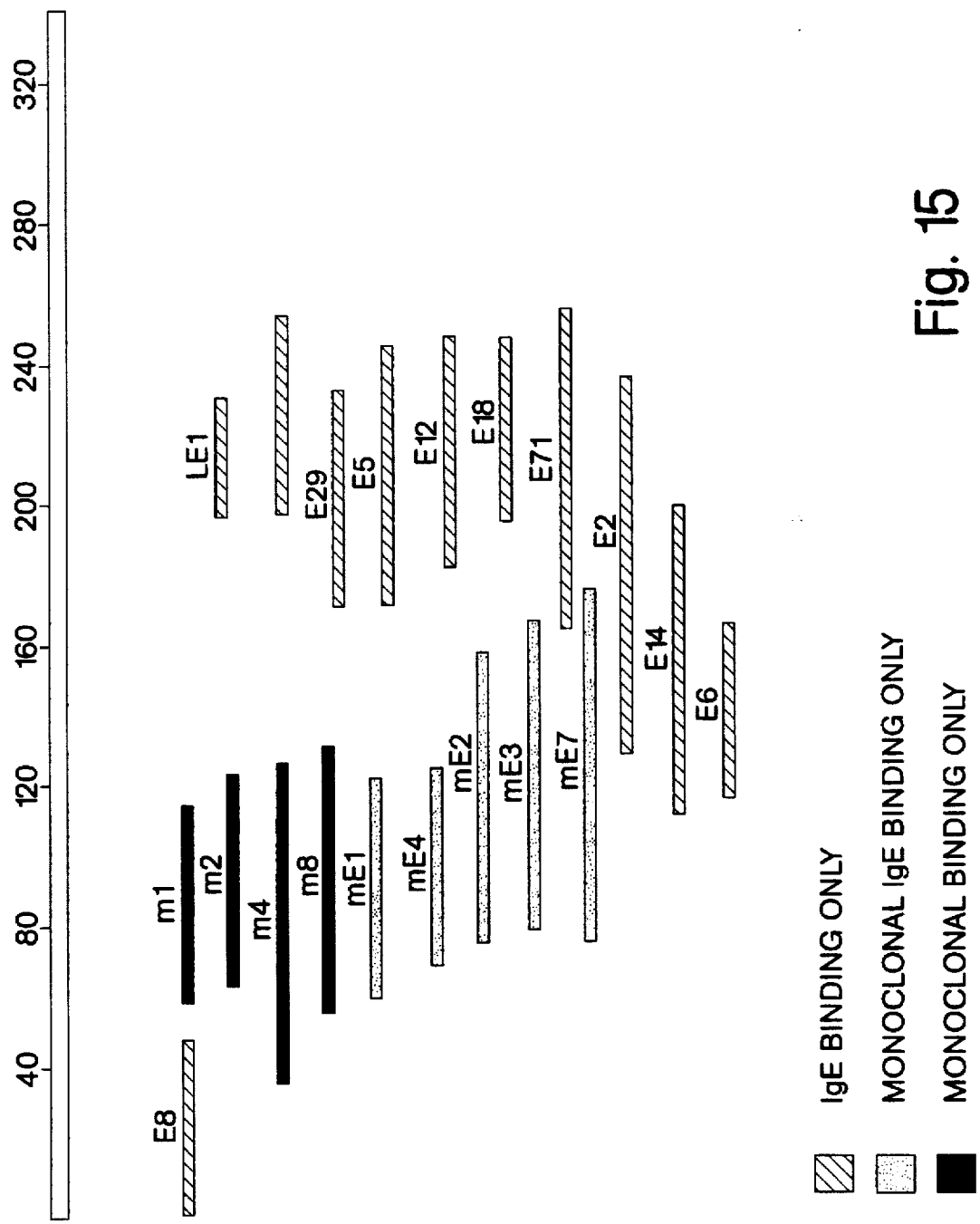
FIG. 15 is a graphic representation showing Lol p Ib.2 (clone 19R) and fragments thereof and corresponding antibody specificities of the polypeptides encoded by the random fragments of Lol p Ib.2 (clone 19R). Cross-hatched bars represent IgE binding only polypeptides. Dotted bars represent monoclonal antibody and IgE binding only polypeptides, and solid black bars represent monoclonal antibody binding only polypeptides.
Figures 16A, 16B:
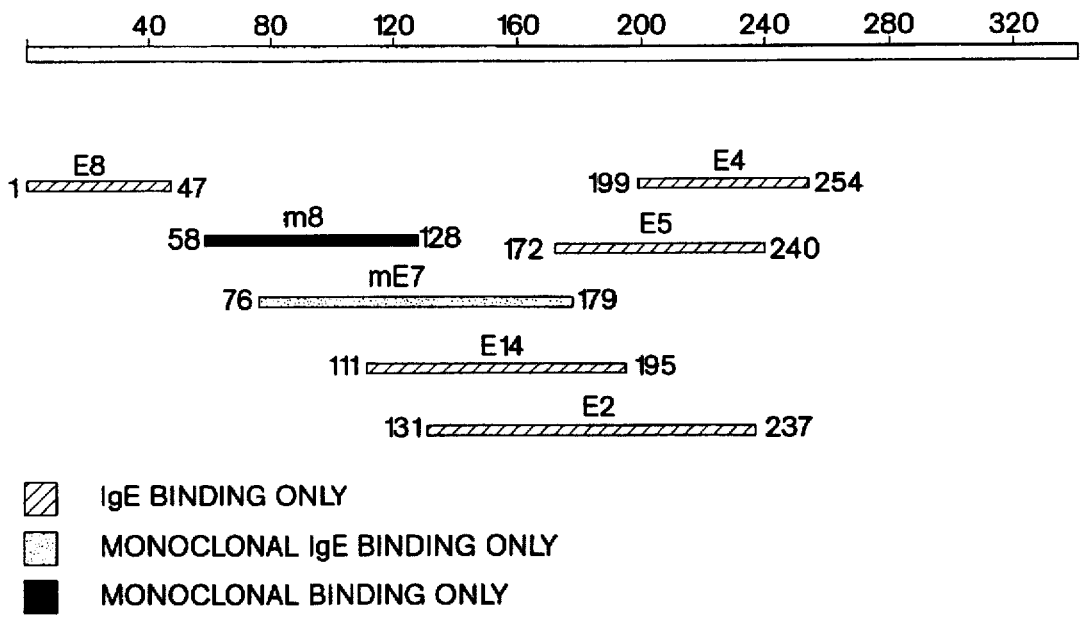
FIG. 16a is a graphic representation of Lol p Ib.2 and fragments thereof and corresponding antibody specificities of the polypeptides encoded by the random fragments of Lol p Ib.2 (clone 19R). Cross-hatched bars represent IgE binding only polypeptides. Dotted bars represent monoclonal antibody and IgE binding only polypeptides, and solid black bars represent monoclonal antibody binding only polypeptides.
FIG. 16b shows binding of IgE from individual patients to recombinant Lol p Ib.1, recombinant Lol p Ib.2 and polypeptides encoded by random fragments of Lol p Ib.2.

Lambda DNA was prepared from purified plaques using Promega Magic Lambda Purification System (Promega, Madison, Wis.). The Lambda DNA was sequenced directly using the fmol DNA Sequencing System (Promega, Madison, Wis.). IgE and MAb binding to the clone 19R random fragment library are shown in FIGS. 15 and 16. Fragments E8, mE1, mE2, mE3, mE4, mE7, E2, E4, E5, E6, E12, E14, E18, E29, E71 and LE1 bound IgE from one or more patients. Fragments m1, m2, m4 and m8 only bound MAb. Fragments mE1, mE2, mE3, mE4 and mE7 bound both MAb and IgE.

Example 11

Characterization of Lol p Ib Allergens Material and Methods

Pollen was obtained from Greer Laboratories, Lenoir, NC. Soluble pollen proteins were extracted as described in Griffith, et al., (1991) *FEBS Letters*, 279:210–215. Crude pollen extract was obtained and its protein concentration determined as described in Ong, et al., (1990) *Int. Arch. Allergy Appl. Immunol.*, 93:338–343. MAbs LpIX3A and LpIX4A were raised against a recombinant protein encoded by the IgE binding portion of clone 12R, as described in Example 8. MAb 7E is specific for Lol p Ia as described in Example 8 and FMC-A1 is as described in Example 1.

Serum used in the experiment to identify allergen regions of Lol p Ia and Lol p Ib was collected by Dr. R. Phomley at the Epworth Hospital (Richmond, Australia) from patients with a history of allergy to ryegrass pollen and a positive skin test to ryegrass pollen extract. IgE was affinity-purified from recombinant allergens as previously described (Singh, et al., (1991) *Proc. Nat'l Acad. Sci. USA*, 21:309; Example 2) except recombinant proteins were derived from lambda-gt11 culture rather than pGEX cultures.

Sera used in the experiment identifying fragments of clone 12R and clone 19R which encode IgE binding polypeptides were obtained from fifty subjects selected on the basis of previous clinical record of spring hay fever symptoms and RAST towards ryegrass pollen (Phadezyme RAST, Pharmacia LKB, Sweden). The RAST score for all sera was four. Sera were also obtained from two subjects, who were shown to be non-atopic by RAST, and used as negative controls. Sera were stored at −20° C. in small aliquots.

Two Dimensional Gel Electrophoresis and Immunoblot Analysis

Two dimensional (2D)-PAGE was performed in a mini-Protean II 2-D cell (Biorad, Richmond, Calif.) according to the manufacturer instructions. The proteins were diluted 1:1 in 4% CHAPS. An aliquot of 13 mg of protein was applied per gel and the sample overlaid with first dimension sample overlay buffer. The first dimension gel was run for 3.5 hours. The second dimension gel was run for 45 minutes. Proteins on 2D-PAGE gels were silver stained to reveal the protein profile.

Conditions for electrophoresis and Western blotting and for the processing of Western blots with MAbs and IgE were as described by Singh, et al., (1985) *Int. Arch. Allergy Appl. Immun.*, 78:300.

Identification of allergenic isoforms in pollen extract.

Figure 17:
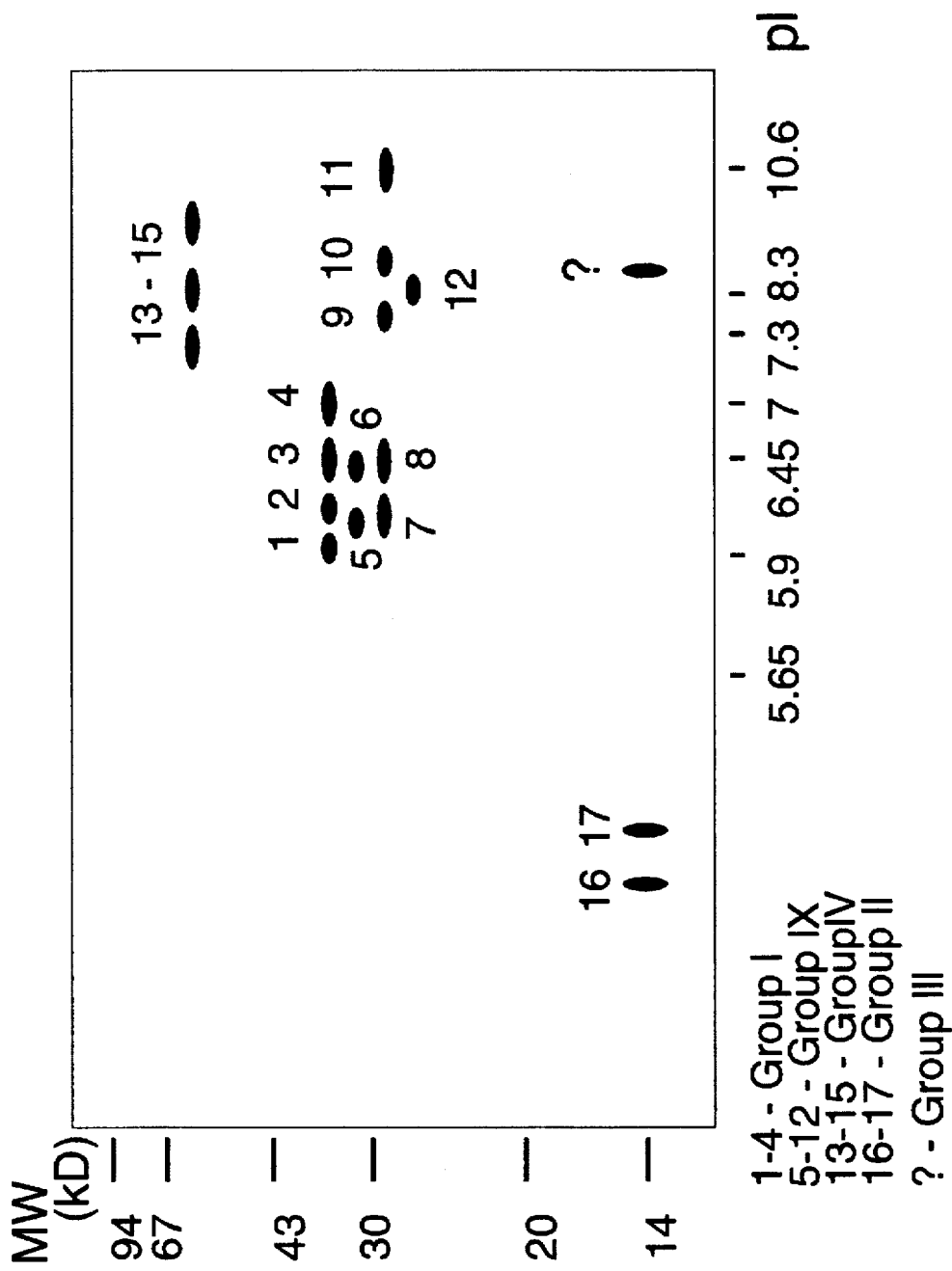
FIG. 17 represents pollen proteins probed with sera of allergic individuals in a two-dimensional Western blot analysis. Group Ia is components 1–4; Group Ib is components 5–12; Group IV is components 13–15; Group II is components 16–17 and Group III is ?.

Probing of Western blots of pollen proteins separated by SDS-PAGE with sera of allergic individuals reveals protein bands at four different molecular weights in the MW range of 28–35 kD that bind IgE. Similar treatment of Western blots of 2D-gels resolved these four bands into twelve allergen spots, as shown in FIG. 17. Using a number of MAbs and IgE preparations the antigenic relationship between these allergens was studied.

Figure 18:
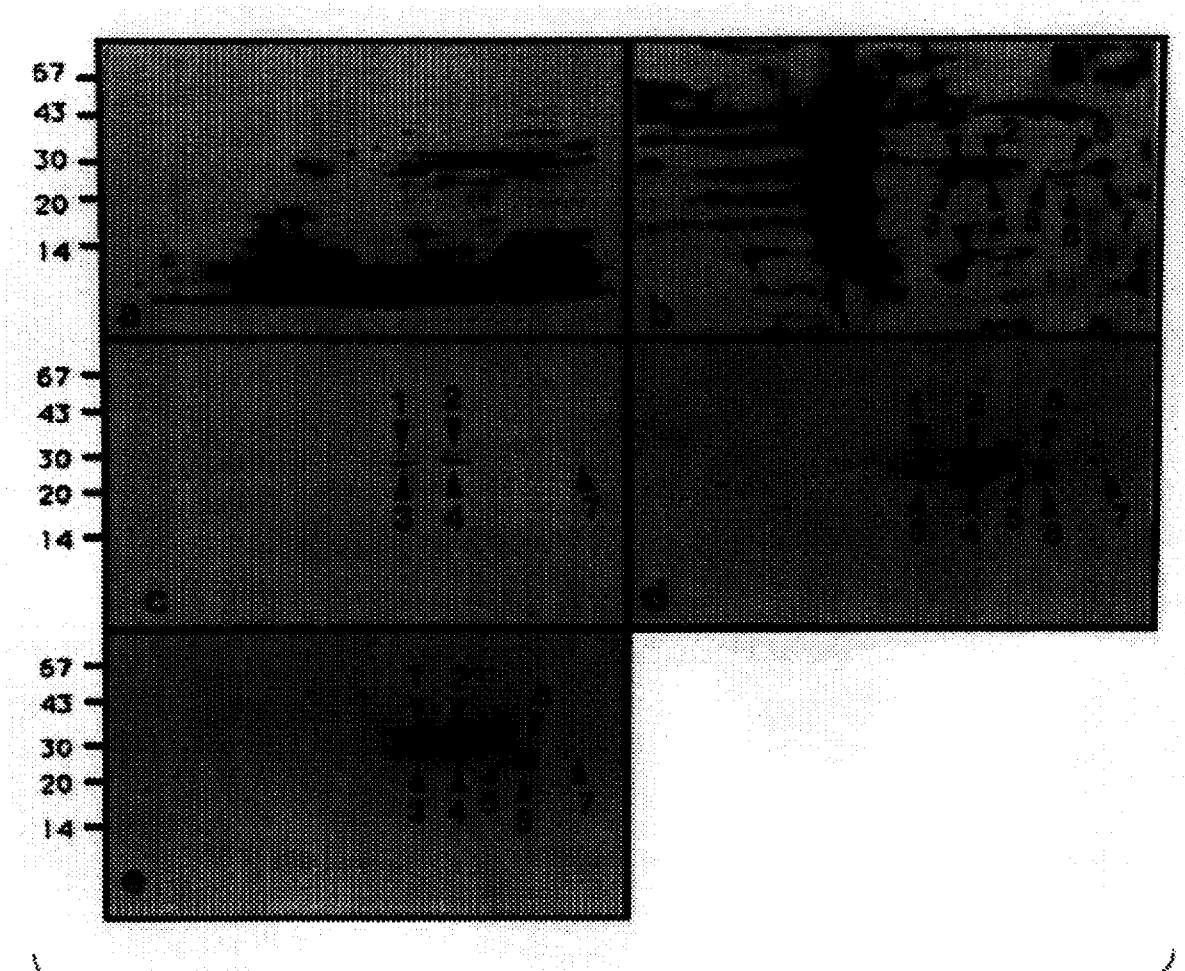
FIG. 18 shows two-dimensional Western analysis of ryegrass pollen proteins. In all cases, ryegrass pollen proteins were subjected to isoelectric focussing (left to right) followed by SDS-PAGE (top to bottom). (a) two-dimensional gel electrophoresis separation of total proteins silver stained. Two-dimensional Western blots probed with (b) total IgE antibodies from pooled sera of grass pollen allergic patients, (c) MAb FMC-A7, (d) IgE antibodies affinity-purified from Lol p Ib.1 and (e) IgE antibodies affinity-purified from Lol p Ib.2.

Two-dimensional Western analyses are shown in FIG. 18 and Table 3. Blots were probed with affinity purified IgE antibodies from Lol p Ib.1, Lol p Ib.2, rfp Lol p Ia, total pooled sera and MAb FMC A7. The total pooled sera have IgE antibodies recognizing two acidic isoforms of the 32 kD component (no. 1, 2), five isoforms of the 30 kD component with pI values in the range of 5–11 (bands 3–7) and a basic band (no. 8) of 28 kD molecule (FIG. 18, panel b). The affinity-purified IgE antibodies from Lol p Ib.1 and Lol p Ib.2 bound to all the isoforms of 28/30/32 kD molecules except isoform no. 5 (FIG. 18, panels d and e). In contrast, MAb FMC-A7 recognized the 32 kD isoforms (bands 1 and 2), two acidic isoforms (bands 3,4) and a basic band no. 7 of the 30 kD component (FIG. 18, panel c).

Figure 19:
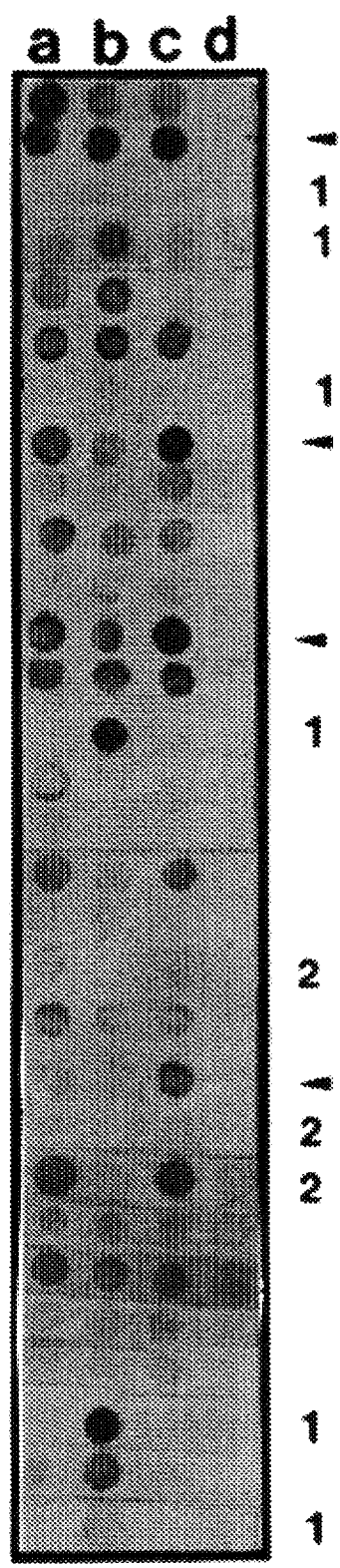
FIG. 19 shows dot blot screening of lambda gt 11 Lol p Ib.1 (clone 12R), Lol p Ia (clone 13R) and Lol p Ib.2 (clone 19R) on *E. coli* Y1090. Two microliters of phage stocks of clones 12R, 13R and 19R and a non-recombinant lambda gt 11 were spotted onto a lawn of *E. coli* Y1090 induced with a nitrocellulose filter saturated with 10 mM IPTG. The protein blots were then probed with individual serum from 30 grass allergic patients. a=Lol p Ib.1, b=Lol p Ia, c=Lol p Ib.2 and d=non-recombinant lambda gt 11. [<]=individuals having higher level of IgE bound to Lol p Ib.2 than Lol p Ia and Lol p Ib.1. [1]=individuals having IgE specific to Lol p Ia. [2]=individuals having IgE specific to Lol p Ib.1 and Lol p Ib.2.

The relative allergenicity of Lol p Ia, Lol p Ib.1 and Lol p Ib.2 were tested using 30 individual allergic sera. FIG. 19 shows that 27 of the patients (90%) have IgE antibodies reactive to Lol p Ia and 6 of them (20% (FIG. 19) have IgE antibodies specific to Lol p Ia (did not bind to either Lol p Ib isoform). Twenty-four patients (80%) have IgE antibodies recognizing both Lol p Ib.1 and Lol p Ib.2 recombinant isoforms. There were 3 patients (10%) who possessed IgE antibodies only recognizing the Lol p Ib isoforms (did not bind to Lol p Ia).

TABLE 3

Characteristics of Allergens on Two Dimensional Gels

| Allergen No. | MW (kD) | pI | Mab binding[a] | IgE binding[b] | Group |
|---|---|---|---|---|---|
| 1 | 34 | 5.5 | A1, 7E | AP13R TIgE | Ia |
| 2 | 34 | 5.9 | A1, 7E | AP13R TIgE | Ia |
| 3 | 34 | 6.45 | A1, 7E | AP13R TIgE | Ia |
| 4 | 34 | 7 | A1, 7E | AP13R TIgE | Ia |
| 5 | 32 | 6 | A1, 3A, 4A | AP12R, AP19R TIgE | Ib |
| 6 | 32 | 6.45 | A1, 3A, 4A | AP12R, AP19R TIgE | Ib |
| 7 | 30 | 6 | A1, 3A, 4A | AP12R, AP19R TIgE | Ib |
| 8 | 30 | 6.45 | A1, 3A, 4A | AP12R, AP19R TIgE | Ib |
| 9 | 30 | 7.2 | A1, 3A | AP12R, AP19R TIgE | Ib |
| 10 | 30 | 8.3 | A1, 3A | AP12R, AP19R TIgE | Ib |
| 11 | 30 | 10.6 | A1, 3A | AP12R, AP19R TIgE | Ib |
| 12 | 28 | 8.0 | A1, 3A | AP12R, AP19R TIgE | Ib |
| 13 | 60 | 7 |  | TIgE | IV |
| 14 | 60 | 7.3 |  | TIgE | IV |
| 15 | 60 | 9 |  | TIgE | IV |
| 16 | 14 | <5.65 |  | TIgE | II |
| 17 | 14 | <5.65 |  | TIgE | II |

[a] A1 — antibody FMC-A1; 3A — antibody LpIX3A; 4A — antibody LpIX4A; 7E-LpI-7E.
[b] AP12R — IgE affinity purified from recombinant Lol p Ib.1, fragment IH. AP13R — IgE purified from recombinant Lol p Ia clone 13R. AP19R — IgE affinity purified from recombinant Lol p Ib.2. TIgE — IgE from whole serum of allergic individuals.

Example 12

Synthesis and Analysis of Lol p Ib.1 Peptides Peptide Synthesis

The amino acid sequence of Lol p Ib.1 was deduced from the cDNA sequence of clone 12R.

The overlapping amino acid sequences of Lol p Ib.1 were constructed by using BT7400 manual peptide synthesizer software program (Biotech Instruments, Ltd., Luton, U.K.).

Thirty 12-met and four 13-mer peptides with four amino acid overlaps were synthesized on a Biotech instruments BT7400 manual multiple peptide synthesis block. The sequences of the peptides are shown in Table 4. Molecular weight (MW), daltons (D), isoelectric point (pI) and hydrophobicity were calculated using Apple's MacProMass 2 software program and are shown in Table 4. The peptides were synthesized on C-terminal Fmoc protected amino acid-resins (25 mmol:Auspep, Melbourne, Australia), held on a frit within a reaction well of the synthesis block. Fmoc-protected amino acids, N,N-Dimethylformamide (DMF), deprotecting solution (DP; 25% piperidine in DMF), dichloromethane (DCM), activating reagent (AR; BOP:HOBT 1:1) and activating solutions (AS; 1.5 equivalent diisopropylethylamine in DMF) were all purchased from Auspep, Melbourne, Australia.

The resin was washed and drained sequentially with 3×1 ml of DMF, in the reaction well. The resin was then treated with 1 ml of DP for ten minutes, to remove the Fmoc group from the first C-terminal amino acid, and then drained the well with vacuum. The well was washed and drained sequentially with 3×1 ml DMF followed by 2.1 ml DCM and then 2.1 ml DMF. Ten-fold excess of the selected amino acids (i.e. 250 mmol) was combined with 150 mg of the AR and dissolved in 1 ml of the AS. The dissolved mixture was added to the appropriate reaction wells and allowed to couple for five hours. The steps described above were sequentially repeated (i.e. deprotect→wash→couple→deprotect→etc.) to complete the assembly of the peptides.

TABLE 4

| Peptide No. (SEQ ID NO:) | Peptide Sequence N-terminus...C-terminus | Peptide MW* (D) | Peptide pI* | IgE Binding | Hydrophobicity |
|---|---|---|---|---|---|
| 1 (13) | ADAGYTPAAAAT | 1194 | 5.0 | — | hydrophobic |
| 2 (14) | AAATPATPAATPA | 1111 | 6.1 | — | hydrophobic |
| 3 (15) | AATPAAAGGKAT | 987 | 10.5 | — | hydrophobic |
| 4 (16) | GKATTDEQKLLE | 1333 | 5.4 | — | hydrophylic |
| 5 (17) | KLLEDVNAGFKA | 1306 | 8.0 | +(3.0) | hydrophylic |
| 6 (18) | GFKAAVAAAANA | 1062 | 10.5 | +(2.0) | hydrophobic |
| 7 (19) | AANAPPADKFKI | 1243 | 10.2 | +(5.0) | hydrophylic |
| 8 (20) | KFKIFEAAFSES | 1405 | 7.3 | — | hydrophobic |
| 9 (21) | FSESSKGLLATS | 1227 | 8.0 | — | hydrophylic |
| 10 (22) | LATSAAKAPGLI | 1113 | 10.5 | +(7.0) | hydrophylic |
| 11 (23) | PGLIPKLNTAYD | 1303 | 5.2 | — | hydrophylic |
| 12 (24) | TAYDVAYKAAEG | 1259 | 5.3 | — | hydrophobic |
| 13 (25) | AAEGATPEAKYD | 1223 | 4.5 | +(4.0) | hydrophylic |
| 14 (26) | AKYDAFVTALTE | 1329 | 4.2 | — | hydrophobic |
| 15 (27) | ALTEGLRVIAGA | 1171 | 8.2 | — | hydrophobic |
| 16 (28) | IAGALEVHAVKPA | 1277 | 8.0 | +(4.0) | hydrophobic |
| 17 (29) | AVKPATEEVPAA | 1183 | 4.4 | — | hydrophylic |
| 18 (30) | VPAAKIPTGELQI | 1338 | 8.0 | +(5.0) | hydrophylic |
| 19 (31) | GELQIVDKIDAA | 1272 | 4.4 | +(11.0) | hydrophylic |
| 20 (32) | IDAAFKIAATAA | 1163 | 7.0 | — | hydrophobic |
| 21 (33) | ATAANAAPTNDK | 1145 | 7.0 | +(12.0) | hydrophobic |
| 22 (34) | TNDKFTVFESAF | 1407 | 4.2 | –(2.0) | hydrophobic |
| 23 (35) | ESAHNKALNECT | 1327 | 4.4 | +(10.0) | hydrophylic |
| 24 (36) | NECTGGAYETYK | 1336 | 6.1 | +(2.8) | hydrophobic |
| 25 (37) | ETYKFIPSLEAA | 1370 | 4.4 | +(3.0) | hydrophobic |
| 26 (38) | LEAAVKQAYAAT | 1236 | 7.1 | — | hydrophyic |
| 27 (39) | YAATVAAPEVKY | 1283 | 7.1 | +(2.0) | hydrophobic |
| 28 (40) | EVKYAVFEAALT | 1342 | 4.4 | — | hydrophobic |
| 29 (41) | AALTKAITAMTQA | 1292 | 10.4 | +(2.5) | hydrophobic |
| 30 (42) | AMTQAQKAGKPA | 1202 | 10.9 | +(4.7) | hydrophylic |
| 31 (43) | GKPAAAAATAAA | 971 | 10.5 | — | hydrophobic |
| 32 (44) | TAAATVATAAAT | 1020 | 6.1 | — | hydrophobic |
| 33 (45) | AAATAAAGAATA | 918 | 8.1 | — | hydrophobic |
| 34 (46) | GAATAAAGGYKA | 1009 | 10.3 | +(12.0) | hydrophobic |

Cleavage and Deprotection of the Peptides

After removal of the Fmoc group from the completed peptide, the resins were washed and drained sequentially with 5×1 ml OCM. The resins were then air dried by vacuum for 10–15 minutes. Cleaving solution (SC; 95% trifluoroacetic acid, 4% phenol, 1% ethanedithiol), diethylether (DEE) and lyophilising solution (LS; 30% acetronitrile in water) were purchased from Adspep, Melbourne, Australia.

The resins were treated for 6 hours with 1 ml of CS. The cleaved peptides were then collected anl allowed to fully precipitate in 50 ml of cold DEE on ice for 30 minutes. The precipitated peptides were then isolated on qualitative filter paper 1 (Whatman, U.K.). The filter paper was washed with 50 ml of LS and the aqueous solution was freeze dried. The crude peptide appeared as an off-white fluffy powder. Crude peptides were subjected to analysis by HPLC and mass spectrometry, by the Auspep Laboratories to check sequence and peptide purity.

Peptide Dot Blot Immunoassays

The peptides were dissolved in water to give a 1.6 mM stock solution. Insoluble peptides were dissolved by sonication (Branson Sonifier 450, U.S.A.) for 1 minute.

The peptides were immobilized onto nitrocellulose (NC) filter by using a modified method published elsewhere (Sithigonglu (1991) *J. Immunol. Methods*, 141:23–32). Two μl of the peptide stock solutions were spotted on the NC filter (Schleicher & Schuell, W. Germany) about i cm apart. After the strips were dried and baked at 80° C. for one hour, they were fixed by exposure, in a tightly sealed plastic box, to vapor from 0.2% glutaraldehyde in PBS at room temperature (18° C.) for one hour. After washing thoroughly with distilled water, the NC filters were blocked with Blotto (10% non-fat dry milk in PBS) for two hours and washed in 1×Tween-PBS (0.1% Tween-20 in PBS) and 2×PBS, five minutes each.

The peptides were then screened for human IgE and mouse/rabbit IgG epitopes with individual sera (diluted 1:4 in PBS with 0.5% BSA), MAbs FMCA7 (Smart et al. (1983) Int. Arch. Allergy Clin. Immunol. 72: 243) and polyclonal rabbit anti-Lol p Ib antibody. The rabbit anti-sera was a gift from Dr. Jenny Roland, Alfred Hospital, Melbourne, Australia.

Figure 20:
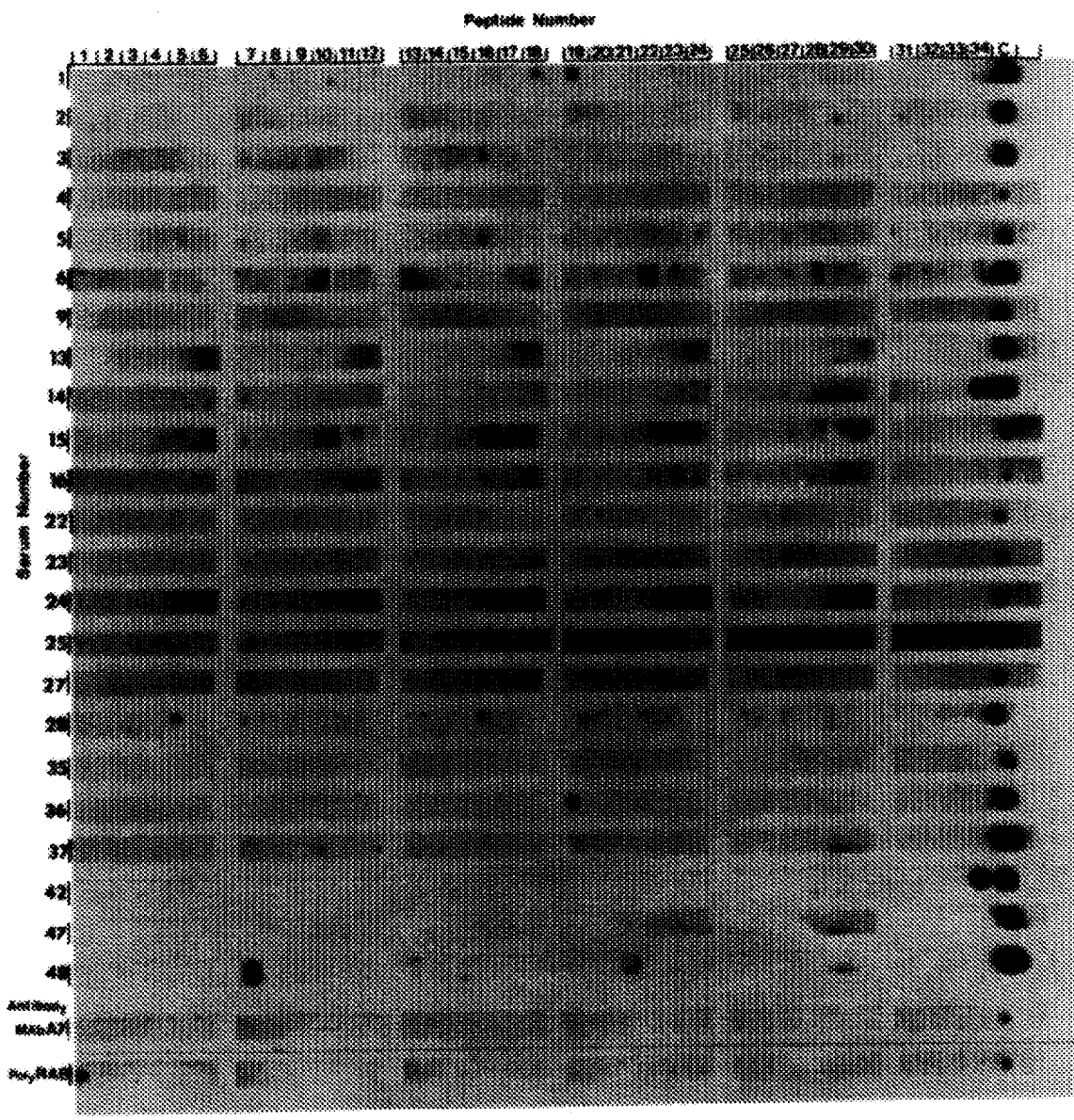
FIG. 20 shows a dot-blot-immunoassay of the 35 overlapping peptides from Lol p Ib.1 (clone 12R) immobilized on nitrocellulose (NC) filter and screened with individual sera showing human IgE-binding, Mabs FMC-A7 and polyclonal anti-Lol p IX1b rabbit antibody. C represents crude ryegrass pollen extract (1 mg/dot) used as a positive control.

Out of the 50 highly ryegrass pollen allergic subjects, 23 had IgE that bound to at least one peptide. Although the majority of the subjects showed mild to moderate IgE-reactivity, there were several showing high reactivity. The dot blot analysis for IgE binding is shown in FIG. 20.

Sera 1, 14, 36, 42 and 48 indicated substantial affinity towards a selection of specific peptides, which were classified as immunodominant linear allergenic B-cell epitopes of Lol p Ib.1.

The intensity of each dot blot was measured by densitometer (Pharmacia LKB UltraScan XL, Sweden). Values are given in arbitrary densitometric units and shown in FIG. 22. Densitometric values greater than two were considered as positive binding in comparison to the background. For every peptide, the sera and antibody values have been added (score/peptide) and divided by the number of positive sera to express the final value as an average (score/sera). Sera C1 and C2 were not grass allergic and were used as negative controls. C refers to crude ryegrass pollen extract (1 μg/dot) as positive control.

Peptide numbers 7, 16, 19, 21, 23, 30 and 34 indicated the highest human IgE-reactivity and were thus classified as major linear allergenic B-cell epitopes of Lol p Ib.1. Mab FMC-A7, and rabbit polyclonal anti-Lol p Ib antiserum were analyzed for IgG binding to the peptides. This data is shown in FIG. 20. The intensity of the dot blots, analyzed as described above, is presented in FIG. 22. The data was analyzed as described above. The MAbs and rabbit antiserum generally showed low binding to the peptides. Peptide numbers 1, 7, 19, 23, 24 and 28 indicated the highest mouse/rabbit IgG-reactivity.

Random Fragment Lambda gt 11 Library of Clone 12R

Figure 21:
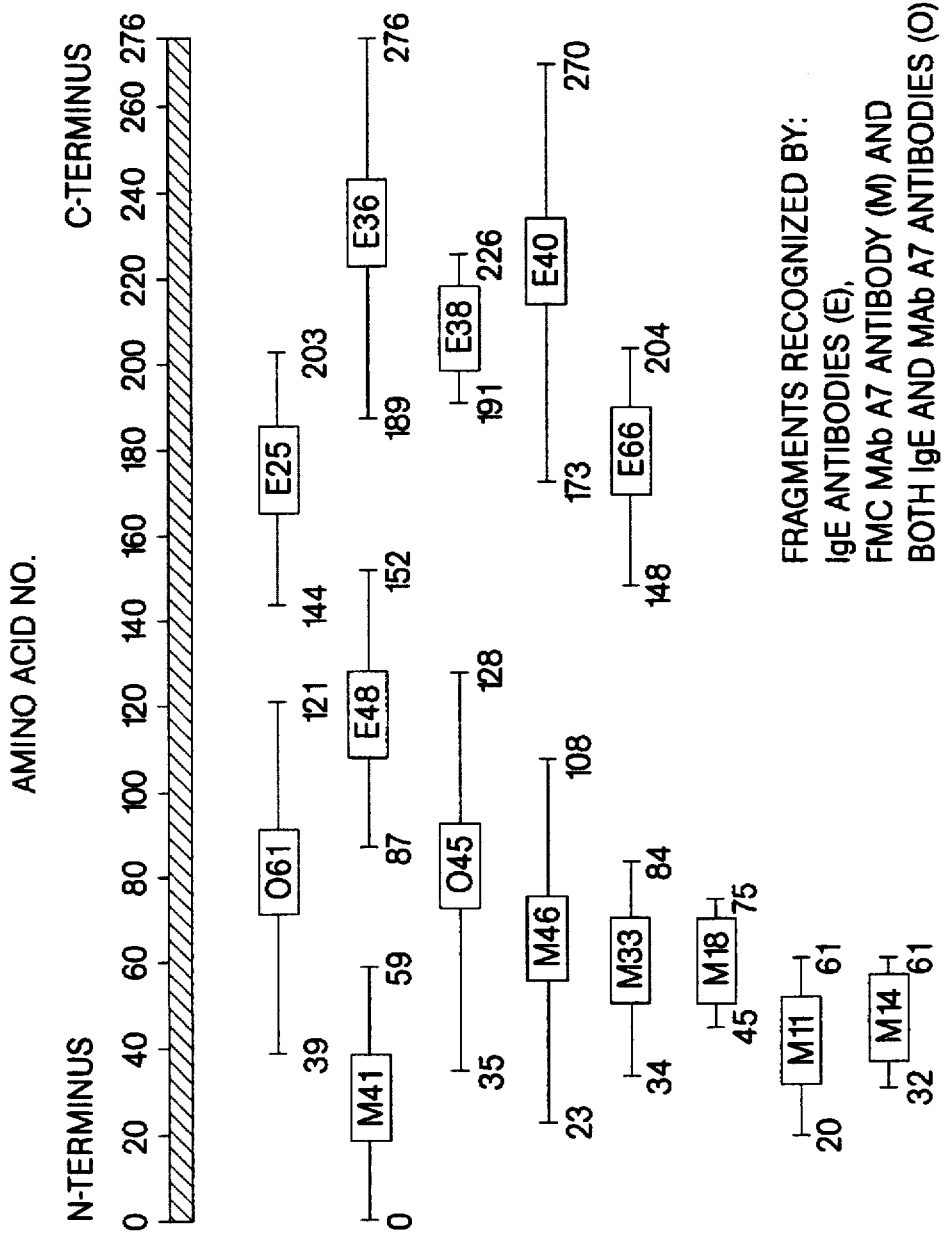
FIG. 21 shows a graphic representation of clone 12R and the fragments corresponding to human IgE and MAb A7 antibody specificities of the polypeptides encoded by the random DNA fragments of Lol p Ib.1. Fragment numbers precedes by "E" indicate fragments recognized by IgE antibodies. Fragment numbers preceded by "M" indicate fragments recognized by FMC Mab A7 antibody. Fragment numbers preceded by "O" indicate fragments recognized by both IgE antibodies and Mab A7 antibodies.

A random fragment library of Lol p Ib.1 was made as described in Example 10. The expressed Lol p Ib.1 fragments were probed for binding to FMC-A1 and IgE in the pooled sera of 18 allergic individuals. This data is presented in FIG. 21. Fragments E25, E36, E38, E40, O45, E48, O61 and E66 bound human IgE. Fragments m11, m14, m18, m33, m41, O45, m46 and O61 bound monoclonal antibody FMC-A7.

Example 13

Extraction of RNA From *Lolium perenne* Flowerhead And Polymorphism Analysis Of The Genes Encoding Lol p Ib.1 and Lol p Ib.2 By Polymerase Chain Reaction (PCR)

Fresh flowerheads were collected from *Lolium perenne* grass in Australia, frozen and shipped to the United States. 500 mg of flowerhead was ground by mortar and pestle on dry ice and suspended in 5 ml of 50 mM Tris pH 9.0 with 0.2M NaCl, 1 Mm EDTA, 0.1% SDS that had been treated overnight with 0.1% DEPC, as described in by Frankis and Mascarhenas (1980) Ann. 45: 595–599. After one extraction with phenol/chloroform/isoamyl alcohol (mixed 25:24:1), the material was sonicated in the phenol/chloroform/isoamyl alcohol for 60 seconds and re-extracted. The sonication was repeated at the third extraction, for 30 seconds. Two final extractions were performed without sonication. The RNA was precipitated from the aqueous phase with 0.1 volume 2M sodium acetate and 2 volumes ethanol. The pellets were recovered by centrifugation, resuspended in dH$_2$O and heated to 65° C. for 5 minutes. Two ml of 4M lithium chloride was added to the RNA preparation and precipitated overnight at 0° C. The RNA pellets were recovered by centrifugation, resuspended in 1 ml dH$_2$O, and again precipitated with 3M sodium acetate and ethanol on dry ice for one hour. The final pellet was washed with 70% ethanol, air dried and resuspended in 100 μl DEPC-treated H$_2$O and stored at −80° C.

First strand cDNA and double stranded cDNA were each synthesized from 7.5 μg flowerhead RNA using a commercially available kit (cDNA synthesis system plus kit, BRL, Gaithersburg, Md.). The second strand cDNA reaction mixture was phenol extracted, ethanol precipitated, and blunted with T4 DNA polymerase (Promega, Madison, Wis.). This double stranded cDNA was ligated to ethanol precipitated, self annealed, oligonucleotides AT and AL for use in a modified Anchored PCR reaction, according to the method of Rafner et al. (1990) *J. Biol. Chem.* 266: 1229–1236; Frohman et al. (1990) *Proc. Natl. Acad. Sci. USA* 85: 8998–9002; and Roux et al. (1990) *BioTech.* 8: 48–57. Oligonucleotide AT has the sequence 5'-GGGTCTAGAGGTACCGTCCGATCGATCATT-3' (Rafner et al. supra) (SEQ ID NO:47). Oligonucleotide AL has the sequence 5'-AATGATCGATGCT-3' (Rafner et al. supra) (SEQ ID NO:48).

The amino termini of clone 12R and clone 19R were amplified from the linkered cDNA (2 μl reaction). PCR were carried out using a commercially available kit (GeneAmp DNA Amplification kit, Perkin Elmer Cetus, Norwalk, Conn.) whereby 10 μl 10×buffer containing dNTPs was mixed with 100 pmol each of the oligonucleotide AP-2 (SEQ ID NO:49) and LP5-8 (SEQ ID NO:50) primers (ED:EDT in a 3:1M ratio), cDNA (2 μl of the linkered cDNA reaction mix), 0.5 μl Amplitaq DNA polymerase, and distilled water to 100 μl. The samples were amplified with a programmable thermal controller (MJ Research, Cambridge, Mass.). The temperature cycling program used was as follows: denature template DNA, 94° C., 1 min,; anneal oligonucleotides, 65° C., 1 min. 30 sec.; elongate, 72° C., 2 min.; repeat for 24 cycles; hold at 4° C.

LP5-8 has the sequence 5'-GCCTTGAAGCC(A/G) GCGTTGA-3'(SEQ ID NO:50) wherein position 12 is either an A or a G. LP5-8 corresponds to the non-coding strand sequence complementary to nucleotides 227 to 244 of Lol p Ib.1 (FIGS. 3b and 3c) and nucleotides 248 to 265 of Lol p Ib.2 (FIGS. 10a and 10b). AP-2 has the sequence 5'-GGGTCTAGAGGTACCGTCC-3'(SEQ ID NO:49). The primary reaction was carried out as described herein. Two percent (2 μl) of this initial amplification was then used in a secondary amplification with 100 pmol each AP-2 and LP5-9, an internally nested Lol p Ib.1 /Ib.2 oligonucleotide primer. LP5-9 has the sequence 5'-TTGGATCCTCGGTCGTCGCCTTCCCT-3' (SEQ ID NO:51) wherein the nucleotides 5'-TTGGATCC-3' (bases 1 through 8 of LP5-9) were added to create a Bam HI restriction site and nucleotides 9–26 correspond to non-coding strand sequence complementary to nucleotides 186 to 203 of Lol p Ib.1 (FIGS. 3b and 3c) and nucleotides 207 to 224 of Lol p Ib.2 (FIGS. 10a and 10b). The dominant amplification product was a DNA smear from about 100–250 base pairs on a ethidium bromide (EtBr)—stained 3% GTG agarose gel.

Amplified DNA was recovered by sequential chloroform, phenol, and chloroform extraction, followed by precipitation on dry ice with 0.5 volumes of 7.5M ammonium acetate and 1.5 volumes of isopropanol. After precipitation and washing with 70% ethanol, the DNA was simultaneously digested with Xba I and Bam HI in a 50 μl reaction, precipitated to reduce the volume to 20 μl and electrophoresed through a preparative 2% GTG NuSeive low melt gel (FMC, Rockport, Me.). The appropriate sized DNA was visualized by EtBr staining, excised, and ligated into appropriately digested pUC19 for sequencing by the dideoxy chain termination method of Sanger et al. (1977) *Proc. Natl. Acad. Sci. USA* 74: 5463–5476) using commercially available sequencing kits (Sequenase kit, Taquence kit, both from U.S. Biochemicals, Cleveland, Ohio).

All clones were derived from a single PCR reaction and amino acid differences only represent potential polymorphisms. These amino acid differences need to be confirmed in an independent PCR due to the inherent error rate in Taq polymerase (Saiki et al. (1988) *Science* 239:487–491).

Eleven clones were found to contain sequences homologous to clone 12R. Two clones were found to be homologous to clone 19R. Potential nucleotide polymorphisms in clone 12R resulting in amino acid differences in Lol p Ib.1 are shown in Table 6.

TABLE 6

| Amino Acid Position | Amino Acid Change |
|---|---|
| −8 | A→V |
| 8 | A→P |
| 15 | T→N |
| 35 | L→R |
| 36 | E→T |
| 44 | A→S |
| 50 | A→P |

A potential polymorphism in clone 19R resulting in an amino acid change in Lol p Ib.2 was found in one clone where the amino acid at position 30 was changed from T→S.

The cDNA encoding an internal portion of clone 12R was cloned from first strand cDNA using oligonucleotides LP5-5 (SEQ ID NO:52) and LP5-6 (SEQ ID NO:53) in a PCR reaction using the above described temperature cycling program. LP5-5 has the sequence 5'-GGGAATTCACCGACGAGCAGAAGCTG-3' (SEQ ID NO:52) wherein bases 1 through 8 (5'-GGGAATTC-3') of LP5-5 were added to create an Eco RI restriction site for cloning purposes and bases 9 to 26 corresponded to nucleotides 199 to 216 of clone 12R and nucleotides 220 to 237 of clone 19R. LP5-6 has the sequence 5'-GGGGATCCCTGGGTCATGGCGGTGAT-3' (SEQ ID NO:53) wherein bases 1 through 7 (5'-GGGGATC-3') (bases 1 through 7 of LP5-6) were added to create a Bam HI restriction site for cloning purposes and bases 8 to 26 were complementary to nucleotides 808 to 826 of clone 12R. The dominant amplified product was a DNA band of approximately 620 base pairs. The amplified DNA product was purified and precipitated as above, followed by digestion with Eco RI and Bam HI and electrophoresed through a preparative 2% low melt gel. The dominant DNA band was excised and ligated into appropriately digested pUC19 for sequencing. Several clones were obtained containing the clone 12R internal sequence.

All clones were derived from a single PCR reaction and amino acid differences only represent potential polymorphisms. These amino acid differences need to be confirmed in an independent PCR due to the inherent error rate in Taq polymerase (Saiki et al. (1988) *Science* 239:487–491.

Potential polymorphisms of the Lol p Ib.1 internal sequence are shown in Table 7.

TABLE 7

| Amino Acid Position | Amino Acid Change |
|---|---|
| 72 | L→F |
| 76 | S→P |
| 78 | A→T |
| 80 | A→R or G |
| 84 | I→V |
| 93 | V→I or R |
| 147 | L→H |
| 148 | Q→A |
| 149 | I→V |
| 169 | T→A |
| 170 | N→D |
| 179 | A→S |
| 185 | N→K |
| 207 | Q→A |
| 214 | A→P |
| 232 | I→M |

Those skilled in the art will appreciate that the invention described herein is susceptible to variations and modifications other than those specifically described. It is to be understood that the invention includes all of the steps, features, compositions and compounds referred to or indicated in this specification, individually or collectively, and any and all combinations of any two or more of said steps or features.

SEQUENCE LISTING ( 1 ) GENERAL INFORMATION:

( i i i ) NUMBER OF SEQUENCES: 53

( 2 ) INFORMATION FOR SEQ ID NO:1:

( i ) SEQUENCE CHARACTERISTICS:
        ( A ) LENGTH: 1229 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 40..942

( i x ) FEATURE:
        ( A ) NAME/KEY: mat_peptide
        ( B ) LOCATION: 115..942

( i x ) FEATURE:
        ( A ) NAME/KEY: sig_peptide
        ( B ) LOCATION: 40..114

( x i ) SEQUENCE DESCRIPTION: SEQ ID NO:1:

```
CGCTATCCCT  CCCTCGTACA  AACAAACGCA  AGAGCAGCA  ATG  GCC  GTC  CAG  AAG         54
                                               Met  Ala  Val  Gln  Lys
                                               -25

TAC  ACG  GTG  GCT  CTA  TTC  CTC  GCC  GTG  GCC  CTC  GTG  GCG  GGC  CCG  GCC    102
Tyr  Thr  Val  Ala  Leu  Phe  Leu  Ala  Val  Ala  Leu  Val  Ala  Gly  Pro  Ala
-20                       -15                      -10                       -5

GCC  TCC  TAC  GCC  GCT  GAC  GCC  GGC  TAC  ACC  CCC  GCA  GCC  GCG  GCC  ACC    150
Ala  Ser  Tyr  Ala  Ala  Asp  Ala  Gly  Tyr  Thr  Pro  Ala  Ala  Ala  Ala  Thr
                1                    5                           10
```

```
CCG GCT ACT CCT GCT GCC ACC CCG GCT GCG GCT GGA GGG AAG GCG ACG         198
Pro Ala Thr Pro Ala Ala Thr Pro Ala Ala Ala Gly Gly Lys Ala Thr
        15                      20                  25

ACC GAC GAG CAG AAG CTG CTG GAG GAC GTC AAC GCT GGC TTC AAG GCA         246
Thr Asp Glu Gln Lys Leu Leu Glu Asp Val Asn Ala Gly Phe Lys Ala
        30                      35                  40

GCC GTG GCC GCC GCT GCC AAC GCC CCT CCG GCG GAC AAG TTC AAG ATC         294
Ala Val Ala Ala Ala Ala Asn Ala Pro Pro Ala Asp Lys Phe Lys Ile
45                      50                  55                      60

TTC GAG GCC GCC TTC TCC GAG TCC TCC AAG GGC CTC CTC GCC ACC TCC         342
Phe Glu Ala Ala Phe Ser Glu Ser Ser Lys Gly Leu Leu Ala Thr Ser
                65                      70                  75

GCC GCC AAG GCA CCC GGC CTC ATC CCC AAG CTC GAC ACC GCC TAC GAC         390
Ala Ala Lys Ala Pro Gly Leu Ile Pro Lys Leu Asp Thr Ala Tyr Asp
            80                      85                  90

GTC GCC TAC AAG GCC GCC GAG GGC GCC ACC CCC GAG GCC AAG TAC GAC         438
Val Ala Tyr Lys Ala Ala Glu Gly Ala Thr Pro Glu Ala Lys Tyr Asp
        95                      100                 105

GCC TTC GTC ACT GCC CTC ACC GAA GCG CTC CGC GTC ATC GCC GGC GCC         486
Ala Phe Val Thr Ala Leu Thr Glu Ala Leu Arg Val Ile Ala Gly Ala
        110                     115                 120

CTC GAG GTC CAC GCC GTC AAG CCC GCC ACC GAG GAG GTC CCT GCT GCT         534
Leu Glu Val His Ala Val Lys Pro Ala Thr Glu Glu Val Pro Ala Ala
125                     130                 135                     140

AAG ATC CCC ACC GGT GAG CTG CAG ATC GTT GAC AAG ATC GAT GCT GCC         582
Lys Ile Pro Thr Gly Glu Leu Gln Ile Val Asp Lys Ile Asp Ala Ala
                145                     150                 155

TTC AAG ATC GCA GCC ACC GCC GCC AAC GCC GCC CCC ACC AAC GAT AAG         630
Phe Lys Ile Ala Ala Thr Ala Ala Asn Ala Ala Pro Thr Asn Asp Lys
            160                     165                 170

TTC ACC GTC TTC GAG AGT GCC TTC AAC AAG GCC CTC AAT GAG TGC ACG         678
Phe Thr Val Phe Glu Ser Ala Phe Asn Lys Ala Leu Asn Glu Cys Thr
        175                     180                 185

GGC GGC GCC TAT GAG ACC TAC AAG TTC ATC CCC TCC CTC GAG GCC GCG         726
Gly Gly Ala Tyr Glu Thr Tyr Lys Phe Ile Pro Ser Leu Glu Ala Ala
    190                     195                 200

GTC AAG CAG GCC TAC GCC GCC ACC GTC GCC GCC GCG CCC GAG GTC AAG         774
Val Lys Gln Ala Tyr Ala Ala Thr Val Ala Ala Ala Pro Glu Val Lys
205                     210                 215                 220

TAC GCC GTC TTT GAG GCC GCG CTG ACC AAG GCC ATC ACC GCC ATG ACC         822
Tyr Ala Val Phe Glu Ala Ala Leu Thr Lys Ala Ile Thr Ala Met Thr
                225                     230                 235

CAG GCA CAG AAG GCC GGC AAA CCC GCT GCC GCC GCT GCC ACA GGC GCC         870
Gln Ala Gln Lys Ala Gly Lys Pro Ala Ala Ala Ala Ala Thr Gly Ala
            240                     245                 250

GCA ACC GTT GCC ACC GGC GCC GCA ACC GCC GCC GCC GGT GCT GCC ACC         918
Ala Thr Val Ala Thr Gly Ala Ala Thr Ala Ala Ala Gly Ala Ala Thr
        255                     260                 265

GCC GCT GCT GGT GGC TAC AAA GCC TGATCAGCTT GCTAATATAC TACTGAACGT       972
Ala Ala Ala Gly Gly Tyr Lys Ala
        270             275

ATGTATGTGC ATGATCCGGG CGGCGAGTGG TTTTGTTGAT AATTAATCTT CGTTTTCGTT      1032

TCATGCAGCC GCGATCGAGA GGGCTTGCAT GCTTGTAATA ATTCAATATT TTTCATTTCT      1092

TTTTGAATCT GTAAATCCCC ATGACAAGTA GTGGGATCAA GTCGGCATGT ATCACCGTTG      1152

ATGCGAGTTT AACGATGGGG AGTTTATCAA AGAATTTATT ATTAAAAAAA AAAAAAAAA       1212

AAAAAAAAA AAAAAA                                                       1229
```

( 2 ) INFORMATION FOR SEQ ID NO:2:

( i ) SEQUENCE CHARACTERISTICS:
        ( A ) LENGTH: 301 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met   Ala   Val   Gln   Lys   Tyr   Thr   Val   Ala   Leu   Phe   Leu   Ala   Val   Ala   Leu
-25                     -20                     -15                                       -10

Val   Ala   Gly   Pro   Ala   Ala   Ser   Tyr   Ala   Ala   Asp   Ala   Gly   Tyr   Thr   Pro
                  -5                                      1                         5

Ala   Ala   Ala   Ala   Thr   Pro   Ala   Thr   Pro   Ala   Ala   Thr   Pro   Ala   Ala   Ala
                  10                      15                        20

Gly   Gly   Lys   Ala   Thr   Thr   Asp   Glu   Gln   Lys   Leu   Leu   Glu   Asp   Val   Asn
      25                            30                      35

Ala   Gly   Phe   Lys   Ala   Ala   Val   Ala   Ala   Ala   Ala   Asn   Ala   Pro   Pro   Ala
40                            45                      50                              55

Asp   Lys   Phe   Lys   Ile   Phe   Glu   Ala   Ala   Phe   Ser   Glu   Ser   Ser   Lys   Gly
                        60                      65                              70

Leu   Leu   Ala   Thr   Ser   Ala   Ala   Lys   Ala   Pro   Gly   Leu   Ile   Pro   Lys   Leu
                  75                      80                              85

Asp   Thr   Ala   Tyr   Asp   Val   Ala   Tyr   Lys   Ala   Ala   Glu   Gly   Ala   Thr   Pro
                  90                      95                        100

Glu   Ala   Lys   Tyr   Asp   Ala   Phe   Val   Thr   Ala   Leu   Thr   Glu   Ala   Leu   Arg
      105                           110                     115

Val   Ile   Ala   Gly   Ala   Leu   Glu   Val   His   Ala   Val   Lys   Pro   Ala   Thr   Glu
120                           125                     130                           135

Glu   Val   Pro   Ala   Ala   Lys   Ile   Pro   Thr   Gly   Glu   Leu   Gln   Ile   Val   Asp
                  140                     145                           150

Lys   Ile   Asp   Ala   Ala   Phe   Lys   Ile   Ala   Ala   Thr   Ala   Ala   Asn   Ala   Ala
                  155                     160                     165

Pro   Thr   Asn   Asp   Lys   Phe   Thr   Val   Phe   Glu   Ser   Ala   Phe   Asn   Lys   Ala
            170                     175                     180

Leu   Asn   Glu   Cys   Thr   Gly   Gly   Ala   Tyr   Glu   Thr   Tyr   Lys   Phe   Ile   Pro
      185                     190                     195

Ser   Leu   Glu   Ala   Ala   Val   Lys   Gln   Ala   Tyr   Ala   Ala   Thr   Val   Ala   Ala
200                           205                     210                           215

Ala   Pro   Glu   Val   Lys   Tyr   Ala   Val   Phe   Glu   Ala   Ala   Leu   Thr   Lys   Ala
                  220                     225                           230

Ile   Thr   Ala   Met   Thr   Gln   Ala   Gln   Lys   Ala   Gly   Lys   Pro   Ala   Ala   Ala
            235                     240                     245

Ala   Ala   Thr   Gly   Ala   Ala   Thr   Val   Ala   Thr   Gly   Ala   Ala   Thr   Ala   Ala
            250                     255                     260

Ala   Gly   Ala   Ala   Thr   Ala   Ala   Ala   Gly   Gly   Tyr   Lys   Ala
            265                     270                     275
```

( 2 ) INFORMATION FOR SEQ ID NO:3:

( i ) SEQUENCE CHARACTERISTICS:
        ( A ) LENGTH: 1295 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:

( A ) NAME/KEY: CDS
( B ) LOCATION: 25..1041

( i x ) FEATURE:
( A ) NAME/KEY: mat_peptide
( B ) LOCATION: 100..1041

( i x ) FEATURE:
( A ) NAME/KEY: sig_peptide
( B ) LOCATION: 25..99

( x i ) SEQUENCE DESCRIPTION: SEQ ID NO:3:

| | | | | | | | | | | | | | | | | |
|---|---|---|---|---|---|---|---|---|---|---|---|---|---|---|---|---|
| GAATTCCCCA | ACGCAAGAGC | AGCA | ATG | GCG | GTG | CAG | AAG | CAC | ACG | GTG | GCG | | | | | 51 |
| | | | Met | Ala | Val | Gln | Lys | His | Thr | Val | Ala | | | | | |
| | | | -25 | | | | | | | -20 | | | | | | |
| CTT | TTC | CTC | GCC | GTG | GCC | CTG | GTG | GCG | GGC | CCG | GCC | GCC | TCC | TAC | GCT | 99 |
| Leu | Phe | Leu | Ala | Val | Ala | Leu | Val | Ala | Gly | Pro | Ala | Ala | Ser | Tyr | Ala | |
| | | -15 | | | | -10 | | | | | -5 | | | | | |
| GCG | GAT | GCT | GGC | TAT | GCC | CCG | GCC | ACC | CCG | GCT | ACT | CCC | GCG | GCC | CCG | 147 |
| Ala | Asp | Ala | Gly | Tyr | Ala | Pro | Ala | Thr | Pro | Ala | Thr | Pro | Ala | Ala | Pro | |
| 1 | | | | 5 | | | | | 10 | | | | | 15 | | |
| GCT | ACT | GCC | GCC | ACC | CCC | GCC | ACC | CCG | GCA | ACC | CCG | GCT | ACT | CCC | GCA | 195 |
| Ala | Thr | Ala | Ala | Thr | Pro | Ala | Thr | Pro | Ala | Thr | Pro | Ala | Thr | Pro | Ala | |
| | | | 20 | | | | 25 | | | | | 30 | | | | |
| GCG | GTG | CCA | TCA | GGG | AAG | GCG | ACG | ACC | GAG | GAG | CAG | AAG | CTG | ATC | GAG | 243 |
| Ala | Val | Pro | Ser | Gly | Lys | Ala | Thr | Thr | Glu | Glu | Gln | Lys | Leu | Ile | Glu | |
| | | 35 | | | | | 40 | | | | | 45 | | | | |
| AAG | ATC | AAC | GCC | GGC | TTC | AAG | GCG | GCC | GTG | GCA | GCC | GCC | GCC | GTC | GTC | 291 |
| Lys | Ile | Asn | Ala | Gly | Phe | Lys | Ala | Ala | Val | Ala | Ala | Ala | Ala | Val | Val | |
| | 50 | | | | | 55 | | | | | 60 | | | | | |
| CCA | CCA | GCT | GAC | AAG | TAC | AAG | ACG | TTC | GTC | GAA | ACC | TTC | GGC | ACG | GCC | 339 |
| Pro | Pro | Ala | Asp | Lys | Tyr | Lys | Thr | Phe | Val | Glu | Thr | Phe | Gly | Thr | Ala | |
| 65 | | | | | 70 | | | | | 75 | | | | | 80 | |
| ACC | AAC | AAG | GCC | TTC | GTT | GAG | GGC | CTC | GCG | TCC | GGC | TAC | GCC | GAT | CAA | 387 |
| Thr | Asn | Lys | Ala | Phe | Val | Glu | Gly | Leu | Ala | Ser | Gly | Tyr | Ala | Asp | Gln | |
| | | | | 85 | | | | | 90 | | | | | 95 | | |
| AGC | AAG | AAC | CAG | CTC | ACC | TCC | AAG | CTC | GAC | GCC | GCC | TTA | AAG | CTC | GCT | 435 |
| Ser | Lys | Asn | Gln | Leu | Thr | Ser | Lys | Leu | Asp | Ala | Ala | Leu | Lys | Leu | Ala | |
| | | | 100 | | | | | 105 | | | | | 110 | | | |
| TAC | GAG | GCT | GCC | CAG | GGC | GCC | ACT | CCC | GAG | GCC | AAG | TAC | GAT | GCC | TAC | 483 |
| Tyr | Glu | Ala | Ala | Gln | Gly | Ala | Thr | Pro | Glu | Ala | Lys | Tyr | Asp | Ala | Tyr | |
| | | 115 | | | | | 120 | | | | | 125 | | | | |
| GTC | GCC | ACC | CTC | ACC | GAG | GCG | CTC | CGC | GTC | ATC | GCC | GGC | ACC | CTC | GAG | 531 |
| Val | Ala | Thr | Leu | Thr | Glu | Ala | Leu | Arg | Val | Ile | Ala | Gly | Thr | Leu | Glu | |
| | 130 | | | | | 135 | | | | | 140 | | | | | |
| GTC | CAC | GCC | GTA | AAG | CCC | GCC | GCC | GAG | GAG | GTC | AAG | GTC | GGC | GCC | ATC | 579 |
| Val | His | Ala | Val | Lys | Pro | Ala | Ala | Glu | Glu | Val | Lys | Val | Gly | Ala | Ile | |
| 145 | | | | | 150 | | | | | 155 | | | | | 160 | |
| CCC | GCC | GCC | GAG | GTG | CAG | CTC | ATC | GAC | AAG | GTC | GAC | GCC | GCG | TAC | AGG | 627 |
| Pro | Ala | Ala | Glu | Val | Gln | Leu | Ile | Asp | Lys | Val | Asp | Ala | Ala | Tyr | Arg | |
| | | | | 165 | | | | | 170 | | | | | 175 | | |
| ACC | GCC | GCC | ACT | GCC | GCC | AAC | GCC | GCC | CCC | GCC | AAC | GAC | AAG | TTC | ACC | 675 |
| Thr | Ala | Ala | Thr | Ala | Ala | Asn | Ala | Ala | Pro | Ala | Asn | Asp | Lys | Phe | Thr | |
| | | | 180 | | | | | 185 | | | | | 190 | | | |
| GTC | TTC | GAG | AAC | ACC | TTT | AAC | AAT | GCC | ATC | AAG | GTG | AGC | CTG | GGC | GCC | 723 |
| Val | Phe | Glu | Asn | Thr | Phe | Asn | Asn | Ala | Ile | Lys | Val | Ser | Leu | Gly | Ala | |
| | | | 195 | | | | 200 | | | | | 205 | | | | |
| GCC | TAC | GAC | AGC | TAC | AAG | TTC | ATC | CCC | ACC | CTT | GTG | GCC | GCC | GTC | AAG | 771 |
| Ala | Tyr | Asp | Ser | Tyr | Lys | Phe | Ile | Pro | Thr | Leu | Val | Ala | Ala | Val | Lys | |
| | | 210 | | | | | 215 | | | | | 220 | | | | |
| CAG | GCC | TAC | GCC | GCC | AAG | CAG | GCC | ACC | GCG | CCG | GAG | GTC | AAG | TAC | ACT | 819 |
| Gln | Ala | Tyr | Ala | Ala | Lys | Gln | Ala | Thr | Ala | Pro | Glu | Val | Lys | Tyr | Thr | |
| 225 | | | | | 230 | | | | | 235 | | | | | 240 | |

```
GTC TCT GAG ACC GCG CTG AAA AAG GCC GTC ACT GCA ATG TCA GAG GCC        867
Val Ser Glu Thr Ala Leu Lys Lys Ala Val Thr Ala Met Ser Glu Ala
            245                 250                 255

GAG AAG GAG GCC ACG CCC GCC GCG GCT GCC ACC GCC ACC CCA ACA CCC        915
Glu Lys Glu Ala Thr Pro Ala Ala Ala Ala Thr Ala Thr Pro Thr Pro
            260                 265                 270

GCG GCT GCC ACC GCC ACC GCA ACC CCC GCC GCT GCC TAC GCC ACC GCT        963
Ala Ala Ala Thr Ala Thr Ala Thr Pro Ala Ala Ala Tyr Ala Thr Ala
            275                 280                 285

ACC CCC GCC GCT GCC ACC GCC ACC GCA ACC CCC GCC GCT GCC ACC GCA       1011
Thr Pro Ala Ala Ala Thr Ala Thr Ala Thr Pro Ala Ala Ala Thr Ala
            290                 295                 300

ACC CCC GCC GCT GCT GGT GGC TAC AAA GTC TGATCAACTC TAACGGTATA          1061
Thr Pro Ala Ala Ala Gly Gly Tyr Lys Val
305                 310

TATCCATCAT GCACATATAC TAACTCGTAT CTATGTGCAT GGCATGGCCG TGGGGTCGAG      1121

CGATTTAGCT GATAATTCAT TCTTGGTTTT CGTTCATGC ATCCGCGCGC CATCAAGCGC       1181

GTGCATGGTC AATTGTTTAT GTAATATTTG TTTTTCGATG TAAAACTAGG CCTGCGTGCC      1241

ACGCTACTCG ACTAATTAAT GAACCGTTTT CACCTTTAAA AAAAAAGGA ATTC             1295
```

( 2 ) INFORMATION FOR SEQ ID NO:4:

( i ) SEQUENCE CHARACTERISTICS:
        ( A ) LENGTH: 339 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Ala Val Gln Lys His Thr Val Ala Leu Phe Leu Ala Val Ala Leu
-25                 -20                 -15                 -10

Val Ala Gly Pro Ala Ala Ser Tyr Ala Ala Asp Ala Gly Tyr Ala Pro
                -5                   1                   5

Ala Thr Pro Ala Thr Pro Ala Ala Pro Ala Thr Ala Ala Thr Pro Ala
             10                  15                  20

Thr Pro Ala Thr Pro Ala Thr Pro Ala Ala Val Pro Ser Gly Lys Ala
         25                  30                  35

Thr Thr Glu Glu Gln Lys Leu Ile Glu Lys Ile Asn Ala Gly Phe Lys
 40                  45                  50                  55

Ala Ala Val Ala Ala Ala Ala Val Val Pro Pro Ala Asp Lys Tyr Lys
                 60                  65                  70

Thr Phe Val Glu Thr Phe Gly Thr Ala Thr Asn Lys Ala Phe Val Glu
             75                  80                  85

Gly Leu Ala Ser Gly Tyr Ala Asp Gln Ser Lys Asn Gln Leu Thr Ser
         90                  95                 100

Lys Leu Asp Ala Ala Leu Lys Leu Ala Tyr Glu Ala Ala Gln Gly Ala
105                 110                 115

Thr Pro Glu Ala Lys Tyr Asp Ala Tyr Val Ala Thr Leu Thr Glu Ala
120                 125                 130                 135

Leu Arg Val Ile Ala Gly Thr Leu Glu Val His Ala Val Lys Pro Ala
                140                 145                 150

Ala Glu Glu Val Lys Val Gly Ala Ile Pro Ala Ala Glu Val Gln Leu
                155                 160                 165

Ile Asp Lys Val Asp Ala Ala Tyr Arg Thr Ala Ala Thr Ala Ala Asn
                170                 175                 180
```

-continued

```
Ala  Ala  Pro  Ala  Asn  Asp  Lys  Phe  Thr  Val  Phe  Glu  Asn  Thr  Phe  Asn
     185                 190                      195

Asn  Ala  Ile  Lys  Val  Ser  Leu  Gly  Ala  Ala  Tyr  Asp  Ser  Tyr  Lys  Phe
200                      205                 210                      215

Ile  Pro  Thr  Leu  Val  Ala  Ala  Val  Lys  Gln  Ala  Tyr  Ala  Ala  Lys  Gln
               220                 225                           230

Ala  Thr  Ala  Pro  Glu  Val  Lys  Tyr  Thr  Val  Ser  Glu  Thr  Ala  Leu  Lys
               235                 240                      245

Lys  Ala  Val  Thr  Ala  Met  Ser  Glu  Ala  Glu  Lys  Glu  Ala  Thr  Pro  Ala
          250                 255                           260

Ala  Ala  Ala  Thr  Ala  Thr  Pro  Thr  Pro  Ala  Ala  Ala  Thr  Ala  Thr  Ala
     265                 270                      275

Thr  Pro  Ala  Ala  Ala  Tyr  Ala  Thr  Ala  Thr  Pro  Ala  Ala  Ala  Thr  Ala
280                      285                 290                      295

Thr  Ala  Thr  Pro  Ala  Ala  Thr  Ala  Thr  Pro  Ala  Ala  Ala  Gly  Gly
               300                 305                      310

Tyr  Lys  Val
```

( 2 ) INFORMATION FOR SEQ ID NO:5:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

```
Ile  Ala  Lys  Val  Xaa  Pro  Gly  Xaa  Xaa  Ile  Thr  Ala  Glu  Tyr  Gly  Asp
1                   5                   10                           15

Lys  Trp  Leu  Asp  Ala  Lys  Ser  Thr  Trp  Tyr  Gly  Lys  Pro  Thr
               20                  25                       30
```

( 2 ) INFORMATION FOR SEQ ID NO:6:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
Ala  Asp  Ala  Gly  Tyr  Thr  Pro  Ala  Ala  Xaa  Xaa  Thr  Pro  Ala  Thr  Ala
1                   5                           10                      15

Pro  Xaa  Thr
```

( 2 ) INFORMATION FOR SEQ ID NO:7:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
Ala  Asp  Ala  Gly  Tyr  Thr  Pro  Ala  Ala  Ala  Thr  Pro  Ala  Thr  Pro
1                   5                           10                      15

Ala  Ala  Thr  Pro  Ala  Ala  Ala  Gly  Gly  Lys  Ala  Thr  Thr  Asp  Glu  Gln
               20                  25                       30

Lys  Leu
```

( 2 ) INFORMATION FOR SEQ ID NO:8:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

```
Ala Ala Pro Val Glu Phe Thr Val Glu Lys Gly Ser Asp Glu Lys Asn
 1               5                  10                  15

Leu Ala Leu Ser Ile Lys Tyr Asn Lys Glu Gly Asp Ser Met Ala
             20                  25                  30
```

( 2 ) INFORMATION FOR SEQ ID NO:9:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

```
Thr Lys Val Asp Leu Thr Val Glu Lys Gly Ser Asp Ala Lys Thr Leu
 1               5                  10                  15

Val Leu Asn Ile Lys Tyr Thr Arg Pro Gly Asp Thr Leu Ala
             20                  25                  30
```

( 2 ) INFORMATION FOR SEQ ID NO:10:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

```
Ala Asp Leu Gly Tyr Ala Pro Ala Thr Pro Ala Ala Pro Gly Ala Gly
 1               5                  10                  15

Tyr Thr Pro Ala Thr Pro Ala Ala Pro
             20                  25
```

( 2 ) INFORMATION FOR SEQ ID NO:11:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

```
Gly Tyr Thr Pro Ala Thr Pro Ala Ala Ala Gly Gly Lys Ala Thr Thr
 1               5                  10                  15

Glu Glu Gln Lys Leu
             20
```

( 2 ) INFORMATION FOR SEQ ID NO:12:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

```
Ala Asp Val Gly Tyr Gly Ala Pro Ala Thr Leu Ala Thr Pro Ala Thr
1               5                   10                  15
Pro Ala Ala Pro Ala Ala Gly Tyr Thr Pro Ala Ala Pro Ala Gly Ala
                20                  25                  30
Ala Pro
```

( 2 ) INFORMATION FOR SEQ ID NO:13:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

```
Ala Asp Ala Gly Tyr Thr Pro Ala Ala Ala Ala Thr
1               5                   10
```

( 2 ) INFORMATION FOR SEQ ID NO:14:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:14:

```
Ala Ala Ala Thr Pro Ala Thr Pro Ala Ala Thr Pro Ala
1               5                   10
```

( 2 ) INFORMATION FOR SEQ ID NO:15:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

```
Ala Ala Thr Pro Ala Ala Ala Gly Gly Lys Ala Thr
1               5                   10
```

( 2 ) INFORMATION FOR SEQ ID NO:16:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

```
Gly Lys Ala Thr Thr Asp Glu Gln Lys Leu Leu Glu
1               5                   10
```

( 2 ) INFORMATION FOR SEQ ID NO:17:

( i ) SEQUENCE CHARACTERISTICS:
        ( A ) LENGTH: 12 amino acids
        ( B ) TYPE: amino acid
        ( D ) TOPOLOGY: linear (i i) MOLECULE TYPE: peptide (x i) SEQUENCE DESCRIPTION: SEQ ID NO:17:

Lys Leu Leu Glu Asp Val Asn Ala Gly Phe Lys Ala
1               5                   10

(2) INFORMATION FOR SEQ ID NO:18:

(i) SEQUENCE CHARACTERISTICS:
        (A) LENGTH: 12 amino acids
        (B) TYPE: amino acid
        (D) TOPOLOGY: linear (i i) MOLECULE TYPE: peptide (x i) SEQUENCE DESCRIPTION: SEQ ID NO:18:

Gly Phe Lys Ala Ala Val Ala Ala Ala Ala Asn Ala
1               5                   10

(2) INFORMATION FOR SEQ ID NO:19:

(i) SEQUENCE CHARACTERISTICS:
        (A) LENGTH: 12 amino acids
        (B) TYPE: amino acid
        (D) TOPOLOGY: linear (i i) MOLECULE TYPE: peptide (x i) SEQUENCE DESCRIPTION: SEQ ID NO:19:

Ala Ala Asn Ala Pro Pro Ala Asp Lys Phe Lys Ile
1               5                   10

(2) INFORMATION FOR SEQ ID NO:20:

(i) SEQUENCE CHARACTERISTICS:
        (A) LENGTH: 12 amino acids
        (B) TYPE: amino acid
        (D) TOPOLOGY: linear (i i) MOLECULE TYPE: peptide (x i) SEQUENCE DESCRIPTION: SEQ ID NO:20:

Lys Phe Lys Ile Phe Glu Ala Ala Phe Ser Glu Ser
1               5                   10

(2) INFORMATION FOR SEQ ID NO:21:

(i) SEQUENCE CHARACTERISTICS:
        (A) LENGTH: 12 amino acids
        (B) TYPE: amino acid
        (D) TOPOLOGY: linear (i i) MOLECULE TYPE: peptide (x i) SEQUENCE DESCRIPTION: SEQ ID NO:21:

Phe Ser Glu Ser Ser Lys Gly Leu Leu Ala Thr Ser
1               5                   10

(2) INFORMATION FOR SEQ ID NO:22:

(i) SEQUENCE CHARACTERISTICS:
        (A) LENGTH: 12 amino acids
        (B) TYPE: amino acid
        (D) TOPOLOGY: linear (i i) MOLECULE TYPE: peptide (x i) SEQUENCE DESCRIPTION: SEQ ID NO:22:

```
   Leu Ala Thr Ser Ala Ala Lys Ala Pro Gly Leu Ile
   1               5                   10
```

( 2 ) INFORMATION FOR SEQ ID NO:23:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:23:

```
   Pro Gly Leu Ile Pro Lys Leu Asn Thr Ala Tyr Asp
   1               5                   10
```

( 2 ) INFORMATION FOR SEQ ID NO:24:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:24:

```
   Thr Ala Tyr Asp Val Ala Tyr Lys Ala Ala Glu Gly
   1               5                   10
```

( 2 ) INFORMATION FOR SEQ ID NO:25:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:25:

```
   Ala Ala Glu Gly Ala Thr Pro Glu Ala Lys Tyr Asp
   1               5                   10
```

( 2 ) INFORMATION FOR SEQ ID NO:26:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:26:

```
   Ala Lys Tyr Asp Ala Phe Val Thr Ala Leu Thr Glu
   1               5                   10
```

( 2 ) INFORMATION FOR SEQ ID NO:27:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:27:

```
   Ala Leu Thr Glu Gly Leu Arg Val Ile Ala Gly Ala
   1               5                   10
```

( 2 ) INFORMATION FOR SEQ ID NO:28:

( i ) SEQUENCE CHARACTERISTICS:
   ( A ) LENGTH: 13 amino acids
   ( B ) TYPE: amino acid
   ( D ) TOPOLOGY: linear ( i i ) MOLECULE TYPE: peptide ( x i ) SEQUENCE DESCRIPTION: SEQ ID NO:28:

Ile Ala Gly Ala Leu Glu Val His Ala Val Lys Pro Ala
1               5                   10

( 2 ) INFORMATION FOR SEQ ID NO:29:

( i ) SEQUENCE CHARACTERISTICS:
      ( A ) LENGTH: 12 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:29:

Ala Val Lys Pro Ala Thr Glu Glu Val Pro Ala Ala
1               5                   10

( 2 ) INFORMATION FOR SEQ ID NO:30:

( i ) SEQUENCE CHARACTERISTICS:
      ( A ) LENGTH: 13 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:30:

Val Pro Ala Ala Lys Ile Pro Thr Gly Glu Leu Gln Ile
1               5                   10

( 2 ) INFORMATION FOR SEQ ID NO:31:

( i ) SEQUENCE CHARACTERISTICS:
      ( A ) LENGTH: 12 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:31:

Gly Glu Leu Gln Ile Val Asp Lys Ile Asp Ala Ala
1               5                   10

( 2 ) INFORMATION FOR SEQ ID NO:32:

( i ) SEQUENCE CHARACTERISTICS:
      ( A ) LENGTH: 12 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:32:

Ile Asp Ala Ala Phe Lys Ile Ala Ala Thr Ala Ala
1               5                   10

( 2 ) INFORMATION FOR SEQ ID NO:33:

( i ) SEQUENCE CHARACTERISTICS:
      ( A ) LENGTH: 12 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:33:

Ala Thr Ala Ala Asn Ala Ala Pro Thr Asn Asp Lys
1               5                   10

( 2 ) INFORMATION FOR SEQ ID NO:34:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:34:

Thr Asn Asp Lys Phe Thr Val Phe Glu Ser Ala Phe
1               5                   10

( 2 ) INFORMATION FOR SEQ ID NO:35:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:35:

Glu Ser Ala Phe Asn Lys Ala Leu Asn Glu Cys Thr
1               5                   10

( 2 ) INFORMATION FOR SEQ ID NO:36:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:36:

Asn Glu Cys Thr Gly Gly Ala Tyr Glu Thr Tyr Lys
1               5                   10

( 2 ) INFORMATION FOR SEQ ID NO:37:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:37:

Glu Thr Tyr Lys Phe Ile Pro Ser Leu Glu Ala Ala
1               5                   10

( 2 ) INFORMATION FOR SEQ ID NO:38:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:38:

```
    Leu Glu Ala Ala Val Lys Gln Ala Tyr Ala Ala Thr
    1               5                   10
```

( 2 ) INFORMATION FOR SEQ ID NO:39:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:39:

```
    Tyr Ala Ala Thr Val Ala Ala Pro Glu Val Lys Tyr
    1               5                   10
```

( 2 ) INFORMATION FOR SEQ ID NO:40:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:40:

```
    Glu Val Lys Tyr Ala Val Phe Glu Ala Ala Leu Thr
    1               5                   10
```

( 2 ) INFORMATION FOR SEQ ID NO:41:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:41:

```
    Ala Ala Leu Thr Lys Ala Ile Thr Ala Met Thr Gln Ala
    1               5                   10
```

( 2 ) INFORMATION FOR SEQ ID NO:42:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:42:

```
    Ala Met Thr Gln Ala Gln Lys Ala Gly Lys Pro Ala
    1               5                   10
```

( 2 ) INFORMATION FOR SEQ ID NO:43:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:43:

```
    Gly Lys Pro Ala Ala Ala Ala Ala Thr Ala Ala Ala
    1               5                   10
```

( 2 ) INFORMATION FOR SEQ ID NO:44:

( i ) SEQUENCE CHARACTERISTICS:
  ( A ) LENGTH: 12 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:44:

Thr Ala Ala Ala Thr Val Ala Thr Ala Ala Ala Thr
1               5                   10

( 2 ) INFORMATION FOR SEQ ID NO:45:

( i ) SEQUENCE CHARACTERISTICS:
  ( A ) LENGTH: 12 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:45:

Ala Ala Ala Thr Ala Ala Ala Gly Ala Ala Thr Ala
1               5                   10

( 2 ) INFORMATION FOR SEQ ID NO:46:

( i ) SEQUENCE CHARACTERISTICS:
  ( A ) LENGTH: 12 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:46:

Gly Ala Ala Thr Ala Ala Ala Gly Gly Tyr Lys Ala
1               5                   10

( 2 ) INFORMATION FOR SEQ ID NO:47:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:47:

GGGTCTAGAG GTACCGTCCG ATCGATCATT     30

( 2 ) INFORMATION FOR SEQ ID NO:48:

( i ) SEQUENCE CHARACTERISTICS:
  ( A ) LENGTH: 13 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:48:

AATGATCGAT GCT     13

( 2 ) INFORMATION FOR SEQ ID NO:49:

( i ) SEQUENCE CHARACTERISTICS:
  ( A ) LENGTH: 19 base pairs
  ( B ) TYPE: nucleic acid
  ( C ) STRANDEDNESS: single ( D ) TOPOLOGY: linear ( i i ) MOLECULE TYPE: cDNA ( x i ) SEQUENCE DESCRIPTION: SEQ ID NO:49:

GGGTCTAGAG GTACCGTCC  19

( 2 ) INFORMATION FOR SEQ ID NO:50:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:50:

GCCTTGAAGC CRGCGTTGA  19

( 2 ) INFORMATION FOR SEQ ID NO:51:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:51:

TTGGATCCTC GGTCGTCGCC TTCCCT  26

( 2 ) INFORMATION FOR SEQ ID NO:52:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:52:

GGGAATTCAC CGACGAGCAG AAGCTG  26

( 2 ) INFORMATION FOR SEQ ID NO:53:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:53:

GGGGATCCCT GGGTCATGGC GGTGAT  26

We claim:

1. An isolated nucleic acid having a nucleotide sequence encoding amino acids −25 through 314 of SEQ ID NO:4.

2. An expression vector comprising the nucleic acid of claim 1.

3. A host cell transformed with the expression vector of claim 2.

4. An isolated nucleic acid having a nucleotide sequence encoding amino acids 1 through 314 of SEQ ID NO:4.

5. An expression vector comprising the nucleic acid of claim 4.

6. A host cell transformed with the expression vector of claim 5.

7. A method of producing Lol p Ib.2 ryegrass pollen allergen comprising, culturing a host cell transformed with an expression vector which encodes amino acids −25 through 314 of SEQ ID NO:4 in an appropriate medium to produce a mixture of cells and medium containing said Lol p Ib.2 ryegrass pollen allergen; and optionally purifying said mixture to produce purified Lol p Ib.2 ryegrass pollen allergen.

8. A method of producing Lol p Ib.2 ryegrass pollen allergen comprising, culturing a host cell transformed with an expression vector which encodes amino acids 1 through 314 of SEQ ID NO:4 in an appropriate medium to produce a mixture of cells and medium containing said Lol p Ib.2 ryegrass pollen allergen; and optionally purifying said mixture to produce purified Lol p Ib.2 ryegrass pollen allergen.

9. The complement of the nucleic acid sequence of claim 1.

10. The complement of the nucleic acid sequence of claim 4.

11. An isolated nucleic acid sequence encoding a protein allergen capable of stimulating T cells specific for Lol p Ib.2, wherein said Lol p Ib.2 has the sequence as shown in SEQ ID NO.4.

* * * * *